(12) United States Patent
Muraca

(10) Patent No.: US 8,088,589 B2
(45) Date of Patent: Jan. 3, 2012

(54) GENE AND PROTEIN EXPRESSION PROFILES ASSOCIATED WITH THE THERAPEUTIC EFFICACY OF EGFR-TK INHIBITORS

(75) Inventor: Patrick J. Muraca, Pittsfield, MA (US)

(73) Assignee: Nuclea Biomarkers, LLC, Pittsfield, MA (US)

( * ) Notice: Subject to any disclaimer, the term of this patent is extended or adjusted under 35 U.S.C. 154(b) by 4 days.

(21) Appl. No.: 12/480,076

(22) Filed: Jun. 8, 2009

(65) Prior Publication Data
US 2009/0263819 A1    Oct. 22, 2009

Related U.S. Application Data

(63) Continuation of application No. 12/072,651, filed on Feb. 27, 2008, now abandoned.

(60) Provisional application No. 60/903,694, filed on Feb. 27, 2007.

(51) Int. Cl.
*G01N 33/53* (2006.01)
*G01N 33/574* (2006.01)
*C07K 14/00* (2006.01)

(52) U.S. Cl. ........ 435/7.1; 435/7.21; 435/7.23; 530/350

(58) Field of Classification Search .................. None
See application file for complete search history.

(56) References Cited

U.S. PATENT DOCUMENTS

| 7,384,940 B2 | 6/2008 | Agus |
| 2007/0202496 A1* | 8/2007 | Beretta .......................... 435/5 |

OTHER PUBLICATIONS

Greenbaum et al. (Genome Biology, 2003, vol. 4, Issue 9, pp. 117.1-117.8).*
Hell et al. (Laboratory Investigation, 1995, 73: 492-496).*
Fu et al. (EMBO J., 1996, 15:43982-4401).*
Yilmaz et al., Tuberkuloz ve Toraks Dergisi (2005); 53(4):323-329.
Minami et al., Lung Cancer (2002); 38:51-57.
Miyakawa et al., Endocrine J. (2003); 50(1): 77-83.
Balko et al., BMC Genomics (2006); 7(1):289f.
Han et al., Int. J. Cancer (2005); 113(1):109-115.
Cappuzzo et al., J. Natl. Cancer Inst. (2004); 96(15):1133-1141.
Dong et al., Cancer Res. (2000); 60:3880-3883.
Russo et al., Int J Cancer (1995); 64:216-221.
Yamsaki et al, Cancer Res. (2007); 67(12): 5779-5788.
Hsieh et al., British J cancer (2007); 97:453-457.
Montesano et al., intl J Cancer (1996); 69(3):225-235.
Burmer et al., Envir. Health Perspect. (1991); 93:27-31.
Busken et al., Digest. Disease Week Abstracts (2003); Abstract No. 850.
Kibel et al., J Urol (2000); 164(1):192-196.
Schmid et al., J Compar Neurology (2001); 430(2): 160-171.
Conner et al., Mol Brain Res (1996); 42:1-17.
Zembutsu et al., intl J Oncol (2003); 32: 29-39.

* cited by examiner

*Primary Examiner* — Peter J Reddig
(74) *Attorney, Agent, or Firm* — DT Ward, P.C.

(57) ABSTRACT

The present invention provides protein and gene expression profiles indicative of whether a patient afflicted with non-small cell lung cancer is likely to be responsive to treatment with a therapeutic compound that is a EGFR-TK inhibitor. By identifying such responsiveness, a treatment provider may determine in advance those patients who would benefit from such treatment, as well as identify alternative therapies for non-responders. The present invention further provide methods of using the gene and protein expression profiles, and assays for identifying the presence of a gene or protein expression profile in a patient sample.

1 Claim, No Drawings

SEQUENCE LISTING

```
<160> NUMBER OF SEQ ID NOS: 32

<210> SEQ ID NO 1
<211> LENGTH: 5332
<212> TYPE: DNA
<213> ORGANISM: Homo sapiens

<400> SEQUENCE: 1
gctgaacttt aggagccagt ctaaggccta ggcgcagacg cactgagcct aagcagccgg      60
tgatggcggc agcggctgtg gtggctgcgg cgggtccggg cccatgaggc gacgaaggag     120
gcgggacggc ttttacccag ccccggactt ccgagacagg gaagctgagg acatggcagg     180
agtgtttgac atagacctgg accagccaga ggacgcgggc tctgaggatg agctggagga     240 gggggtcag ttaaatgaaa gcatggacca tgggggagtt ggaccatatg aacttggcat     300
ggaacattgt gagaaatttg aaatctcaga aactagtgtg aacagagggc cagaaaaaat     360
cagaccagaa tgtttgagc tacttcgggt acttggtaaa gggggctatg gaaaggtttt     420
tcaagtacga aaagtaacag gagcaaatac tgggaaaata tttgccatga aggtgcttaa     480
aaaggcaatg atagtaagaa atgctaaaga tacagctcat acaaaagcag aacggaatat     540
tctggaggaa gtaaagcatc ccttcatcgt ggatttaatt tatgcctttc agactggtgg     600
aaaactctac ctcatccttg agtatctcag tggaggagaa ctatttatgc agttagaaag     660
agagggaata tttatggaag acactgcctg cttttacttg gcagaaatct ccatggcttt     720
ggggcattta catcaaaagg ggatcatcta cagagacctg aagccggaga atatcatgct     780
taatcaccaa ggtcatgtga aactaacaga ctttggacta tgcaaagaat ctattcatga     840
tggaacagtc acacacacat tttgtggaac aatagaatac atggcccctg aaatcttgat     900
gagaagtggc cacaatcgtg ctgtggattg gtggagtttg ggagcattaa tgtatgacat     960
gctgactgga gcaccccat tcactgggga gaatagaaag aaaacaattg acaaaatcct    1020
caaatgtaaa ctcaatttgc ctccctacct cacacaagaa gccagagatc tgcttaaaaa    1080
gctgctgaaa agaaatgctg cttctcgtct gggagctggt cctggggacg ctggagaagt    1140
tcaagctcat ccattcttta gacacattaa ctgggaagaa cttctggctc gaaaggtgga    1200
```

-continued

| | |
|---|---|
| gccccccttt aaacctctgt tgcaatctga agaggatgta agtcagtttg attccaagtt | 1260 |
| tacacgtcag acacctgtcg acagcccaga tgactcaact ctcagtgaaa gtgccaatca | 1320 |
| ggtctttctg ggttttacat atgtggctcc atctgtactt gaaagtgtga agaaaagtt | 1380 |
| ttcctttgaa ccaaaaatcc gatcacctcg aagatttatt ggcagccac gaacacctgt | 1440 |
| cagcccagtc aaattttctc ctggggattt ctggggaaga ggtgcttcgg ccagcacagc | 1500 |
| aaatcctcag acacctgtgg aatacccaat ggaaacaagt ggcatagagc agatggatgt | 1560 |
| gacaatgagt ggggaagcat cggcaccact tccaatacga cagccgaact ctgggccata | 1620 |
| caaaaaacaa gcttttccca tgatctccaa acggccagag cacctgcgta tgaatctatg | 1680 |
| acagagcaat gcttttaatg aatttaaggc aaaaaggtg gagagggaga tgtgtgagca | 1740 |
| tcctgcaagg tgaaacgact caaaatgaca gtttcagaga gtcaatgtca ttacatagaa | 1800 |
| cacttcagac acaggaaaaa taaacgtgga ttttaaaaaa tcaatcaatg gtgcaaaaaa | 1860 |
| aaacttaaag caaaatagta ttgctgaact cttaggcaca tcaattaatt gattcctcgc | 1920 |
| gacatcttct caaccttatc aaggattttc atgttgatga ctcgaaactg acagtattaa | 1980 |
| gggtaggatg ttgcttctga atcactgttg agttctgatt gtgttgaaga agggttatcc | 2040 |
| tttcattagg caaagtacaa aattgcctat aatacttgca actaaggaca aattagcatg | 2100 |
| caagcttggt caaacttttt ccagcaaaat ggaagcaaag acaaagaaa cttaccaatt | 2160 |
| gatgttttac gtgcaaacaa cctgaatctt ttttttatat aaatatatat ttttcaaata | 2220 |
| gattttgat tcagctcatt atgaaaaaca tcccaaactt taaaatgcga aattattggt | 2280 |
| tggtgtgaag aaagccagac aacttctgtt tcttctcttg gtgaaataat aaaatgcaaa | 2340 |
| tgaatcattg ttaaccacag ctgtggctcg tttgagggat tggggtggac ctggggttta | 2400 |
| ttttcagtaa cccagctgca atacctgtct gtaatatgag aaaaaaaaa tgaatctatt | 2460 |
| taatcatttc tacttgcagt actgctatgt gctaagctta actggaagcc ttggaatggg | 2520 |
| cataagttgt atgtcctaca tttcatcatt gtcccgggcc tgcattgcac tggaaaaaaa | 2580 |
| aatcgccacc tgttcttaca ccagtatttg gttcaagaca ccaaatgtct tcagcccatg | 2640 |
| gctgaagaac aacagaagag agtcaggata aaaatacat actgtggtcg gcaaggtgag | 2700 |
| ggagataggg atatccaggg gaagagggtg ttgctgtggc ccactctctg tctaatctct | 2760 |
| ttacagcaaa ttggtaagat tttcagttt acttctttct actgtttctg ctgtctacct | 2820 |
| tccttatatt ttttttcctca acagttttaa aaagaaaaaa aggtctattt tttttctcc | 2880 |
| tatacttggg ctacattttt tgattgtaaa aatatttgat ggccttttga tgaatgtctt | 2940 |
| ccacagtaaa gaaaacttag tggcttaatt taggaaacat gttaacagga cactatgttt | 3000 |
| ttgaaattgt aacaaaatct acataaatga tttacaggtt aaaagaataa aaataaaggt | 3060 |
| aactttacct ttcttaaata tttcctgcct taaagagagc atttccatga ctttagctgg | 3120 |
| tgaaggggtt taatatctgc agagctttat aaaaatatat ttcagtgcat actggtataa | 3180 |
| tagatgatca tgcagttgca gttgagttgt atcaccttt ttgtttgtct tttataatgt | 3240 |
| cttcagtctg agtgtgcaaa gtcaatttgt aatattttgc aaccctagga tttttttaaa | 3300 |
| tagatgctgc ttgctatgtt ttcaaacctt tttgagccat aggatccaag ccataaaatt | 3360 |
| ctttatgcat gttgaattca gtcagaaaag agcaaggctt tgcttttga aattgcaact | 3420 |
| caaatgagat gggatgaaat cctatgacag taagcaaaaa cagaaccatg aaaaatgatt | 3480 |
| ggacatacac ctttcaatt gtggcaataa ttgaaagaat cgataaaagt tcatctttgg | 3540 |
| acagaaagcc tttaaaaaaa aaatcactcc ctcttccccc tcctccctta ttgcagcagc | 3600 |

```
ctactgagaa ctttgactgt tgctggtaaa ttagaagcta caataataat taagggcaga    3660
aattatactt aaaaagtgca gatccttgtt ctttgacaat ttgtgatgtc tgaaaaaaca    3720
gaacccgaaa agctatggtg atatgtacag gcattatttc agactgtaaa tggcttgtga    3780
tactcttgat acttgttttc aaatatgttt actaactgta gtgttgactg cctgaccaaa    3840
ttccagtgaa acttatacac caaaatattc ttcctaggtc ctatttgcta gtaacatgag    3900
cactgtgatt ggctggctat aaccacccca gttaaaccat tttcataatt agtagtgcca    3960
gcaatagtgg caaacactgc aacttttctg cataaaaagc attaattgca cagctaccat    4020
ccacacaaat acatagtttt tctgacttca catttattaa gtgaaattta tttcccatgc    4080
tgtggaaagt ttattgagaa cttgtttcat aaatggatat ccctactatg actgtgaaaa    4140
catgtcaagt gtcacattag tgtcacagac agaaagcaca cacctatgca atatggctta    4200
tctatattta tttgtaaaaa tccaagcata gtttaaaata tgatgtcgat attactagtc    4260 ttgagttttct aagagggttc tttatgttat accaggtaag tgtataaaag agattaagtg    4320 ctttttttttc atcacttgat tattttcttt aaaatcagct attacaggat attttttttat    4380 tttatacatg ctgttttttta attaaaatat aatcactgaa gtttactaat ttgattttat    4440
aaggtttgta gcattacaga ataactaaac tgggatttat aaaccagctg tgattaacaa    4500
tgtaaagtat taattattga actttgaacc agatttttag gaaaattatg ttcttttttcc    4560 ccctttatgg tcttaactaa tttgaatcct tcaagaagga ttttttccata ctattttttta    4620 agatagaaga taatttgtgg gcaggggtgg aggatgcatg tatgatactc cataaaattca    4680 acattcttta ctataggtaa tgaatgatta taaacaagat gcatcttaga tagtattaat    4740
atactgagcc ttggattata tatttaatat aggacctatt ttgaatattc agttaatcat    4800
atggttccta gcttacaagg gctagatcta agattattcc catgagaaat gttgaattta    4860
tgaagaatag attttaaggc tttgaaaatg gttaatttct caaaaacatc aatgtccaaa    4920
catctacctt ttttcatagg agtagacact agcaagctgg acaaactatc acaaaagtat    4980
ttgtcacaca taacctgtgg tctgttgctg attaatacag tactttttct tgtgtgattc    5040
ttaacattat agcacaagta ttatctcagt ggattatccg gaataacatc tgaaagatgg    5100
gttcatctat gtttgtgttt gctctttaaa ctattgtttc tcctatccca agttcgcttt    5160
gcatctatca gtaaataaaa ttcttcagct gccttattag gagtgctatg agggtaacac    5220
ctgttctgct tttcatcttg tatttagttg actgtattat ttgatttcgg attgaatgaa    5280
tgtaaataga aattaaatgc aaatttgaat gaacataaaa aaaaaaaaaa aa            5332

<210> SEQ ID NO 2
<211> LENGTH: 829
<212> TYPE: DNA
<213> ORGANISM: Homo sapiens

<400> SEQUENCE: 2
cctcttttcc gtggcgcctc ggaggcgttc agctgcttca agatgaagct gaacatctcc      60
ttcccagcca ctggctgcca gaaactcatt gaagtggacg atgaacgcaa acttcgtact     120
ttctatgaga gcgtatggc cacagaagtt gctgctgacg ctctgggtga agaatggaag     180
ggttatgtgg tccgaatcag tggtgggaac gacaaacaag gtttccccat gaagcagggt     240
gtcttgaccc atggccgtgt ccgcctgcta ctgagtaagg ggcattcctg ttacagacca     300
aggagaactg gagaaagaaa gagaaaatca gttcgtggtt gcattgtgga tgcaaatctg     360
agcgttctca acttggttat tgtaaaaaaa ggagagaagg atattcctgg actgactgat     420
```

```
actacagtgc ctcgccgcct gggccccaaa agagctagca gaatccgcaa acttttcaat      480
ctctctaaag aagatgatgt ccgccagtat gttgtaagaa agcccttaaa taaagaaggt      540
aagaaaccta ggaccaaagc acccaagatt cagcgtcttg ttactccacg tgtcctgcag      600
cacaaacggc ggcgtattgc tctgaagaag cagcgtacca agaaaaataa agaagaggct      660
gcagaatatg ctaaactttt ggccaagaga atgaaggagg ctaaggagaa gcgccaggaa      720
caaattgcga agagacgcag actttcctct ctgcgagctt ctacttctaa gtctgaatcc      780
agtcagaaat aagatttttt gagtaacaaa taaataagat cagactctg                  829

<210> SEQ ID NO 3
<211> LENGTH: 3008
<212> TYPE: DNA
<213> ORGANISM: Homo sapiens

<400> SEQUENCE: 3
taattatggg tctgtaacca ccctggactg ggtgctcctc actgacggac ttgtctgaac       60
ctctctttgt ctccagcgcc cagcactggg cctggcaaaa cctgagacgc ccggtacatg      120
ttggccaaat gaatgaacca gattcagacc ggcaggggcg ctgtggttta ggagggggcct     180 ggggtttctc ccaggaggtt tttgggcttg cgctggaggg ctctggactc ccgtttgcgc      240
cagtggcctg catcctggtc ctgtcttcct catgtttgaa tttctttgct ttcctagtct      300
ggggagcagg gaggagccct gtgccctgtc ccaggatcca tgggtaggaa caccatggac      360
agggagagca acggggcca tctgtcacca ggggcttagg gaaggccgag ccagcctggg       420
tcaaagaagt caaaggggct gcctggagga ggcagcctgt cagctggtgc atcagaggct      480
gtggccaggc cagctgggct cggggagcgc cagcctgaga ggagcgcgtg agcgtcgcgg      540
gagcctcggg caccatgagc gacgtggcta ttgtgaagga gggttggctg cacaaacgag      600
gggagtacat caagacctgg cggccacgct acttcctcct caagaatgat ggcaccttca      660
ttggctacaa ggagcggccg caggatgtgg accaacgtga ggctcccctc aacaacttct      720
ctgtggcgca gtgccagctg atgaagacgg agcggccccg gcccaacacc ttcatcatcc      780
gctgcctgca gtggaccact gtcatcgaac gcaccttcca tgtggagact cctgaggagc      840
gggaggagtg gacaaccgcc atccagactg tggctgacgg cctcaagaag caggaggagg      900
aggagatgga cttccggtcg ggctcaccca gtgacaactc aggggctgaa gagatgggagg      960 tgtccctggc caagcccaag caccgcgtga ccatgaacga gtttgagtac ctgaagctgc     1020
tgggcaaggg cacctttggc aaggtgatcc tggtgaagga aaggccaca ggccgctact      1080 acgccatgaa gatcctcaag aaggaagtca tcgtggccaa ggacgaggtg gcccacacac     1140 tcaccgaaa ccgcgtcctg cagaactcca ggcacccctt cctcacagcc tgaagtact      1200 ctttccagac ccacgaccgc ctctgctttg tcatggagta cgccaacggg ggcgagctgt     1260
tcttccacct gtcccgggag cgtgtgttct ccgaggaccg gccccgcttc tatgcgcctg     1320
agattgtgtc agccctggac tacctgcact cggagaagaa cgtggtgtac cgggacctca     1380
agctggagaa cctcatgctg gacaaggacg ggcacattaa gatcacagac ttcgggctgt     1440
gcaaggaggg gatcaaggac ggtgccacca tgaagacctt tgcggcaca cctgagtacc      1500 tggcccccga ggtgctggag acaatgact acgccgtgc agtggactgg tggggctgg       1560 gcgtggtcat gtacgagatg atgtgcggtc gcctgccctt ctacaaccag gaccatgaga     1620 agcttttga gctcatcctc atggaggaga tccgcttccc gcgcacgctt ggtcccgagg     1680
ccaagtcctt gctttcaggg ctgctcaaga aggaccccca gcagaggctt ggcggggget     1740
```

-continued

```
ccgaggacgc caaggagatc atgcagcatc gcttctttgc cggtatcgtg tggcagcacg   1800
tgtacgagaa gaagctcagc ccacccttca agccccaggt cacgtcggag actgacacca   1860
ggtattttga tgaggagttc acggcccaga tgatcaccat cacaccacct gaccaagatg   1920
acagcatgga gtgtgtggac agcgagcgca ggccccactt cccccagttc tcctactcgg   1980
ccagcggcac ggcctgaggc ggcggtggac tgcgctggac gatagcttgg agggatggag   2040
aggcggcctc gtgccatgat ctgtatttaa tggtttttat ttctcgggtg catttgagag   2100
aagccacgct gtcctctcga gcccagatgg aaagacgttt ttgtgctgtg ggcagcaccc   2160
tcccccgcag cggggtaggg aagaaaacta tcctgcgggt tttaattat ttcatccagt    2220
ttgttctccg ggtgtggcct cagccctcag aacaatccga ttcacgtagg gaaatgttaa   2280
ggacttctgc agctatgcgc aatgtggcat tgggggccg gcaggtcct gcccatgtgt     2340
cccctcactc tgtcagccag ccgccctggg ctgtctgtca ccagctatct gtcatctctc   2400
tggggccctg ggcctcagtt caacctggtg gcaccagatg caacctcact atggtatgct   2460
ggccagcacc ctctcctggg ggtggcaggc acacagcagc cccccagcac taaggccgtg   2520
tctctgagga cgtcatcgga ggctgggccc ctgggatggg accagggatg ggggatgggc   2580
cagggtttac ccagtgggac agaggagcaa ggtttaaatt tgttattgtg tattatgttg   2640
ttcaaatgca ttttgggggt ttttaatctt tgtgacagga aagccctccc ccttcccctt   2700
ctgtgtcaca gttcttggtg actgtcccac cgggagcctc cccctcagat gatctctcca   2760
cggtagcact tgaccttttc gacgcttaac ctttccgctg tcgccccagg ccctccctga   2820
ctccctgtgg gggtggccat ccctgggccc ctccacgcct cctggccaga cgctgccgct   2880
gccgctgcac cacggcgttt ttttacaaca ttcaacttta gtattttac tattataata    2940
taatatggaa ccttccctcc aaattcttca ataaagttg cttttcaaaa aaaaaaaaa     3000
aaaaaaaa                                                            3008
```

<210> SEQ ID NO 4
<211> LENGTH: 8680
<212> TYPE: DNA
<213> ORGANISM: Homo sapiens

<400> SEQUENCE: 4

```
acggggcctg aagcggcggt accggtgctg gcggcggcag ctgaggcctt ggccgaagcc     60
gcgcgaacct cagggcaaga tgcttggaac cggacctgcc gccgccacca ccgctgccac    120
cacatctagc aatgtgagcg tcctgcagca gtttgccagt ggcctaaaga gccggaatga    180
ggaaaccagg gccaaagccg ccaaggagct ccagcactat gtcaccatgg aactccgaga    240
gatgagtcaa gaggagtcta ctcgcttcta tgaccaactg aaccatcaca tttttgaatt    300
ggtttccagc tcagatgcca atgagaggaa aggtggcatc ttggccatag ctagcctcat    360
aggagtggaa ggtgggaatg ccacccgaat tggcagattt gccaactatc ttcggaacct    420
cctcccctcc aatgacccag ttgtcatgga atggcatcc aaggccattg gcgtcttgc     480
catggcaggg gacactttta ccgctgagta cgtggaattt gaggtgaagc gagccctgga    540
atggctgggt gctgaccgca atgagggccg gagacatgca gctgtcctgg ttctccgtga    600
gctggccatc agcgtcccta ccttcttctt ccagcaagtg caaccttct ttgacaacat     660
ttttgtggcc gtgtgggacc ccaaacaggc catccgtgag ggagctgtag ccgcccttcg    720
tgcctgtctg attctcacaa cccagcgtga gccgaaggag atgcagaagc tcagtggta    780
caggcacaca tttgaagaag cagagaaggg atttgatgag accttggcca aagagaaggg   840
```

```
catgaatcgg gatgatcgga tccatggagc cttgttgatc cttaacgagc tggtccgaat    900
cagcagcatg gagggagagc gtctgagaga agaaatggaa gaaatcacac agcagcagct    960
ggtacacgac aagtactgca aagatctcat gggcttcgga acaaaacctc gtcacattac   1020
cccctccacc agtttccagg ctgtacagcc ccagcagtca aatgccttgg tggggctgct   1080
ggggtacagc tctcaccaag gcctcatggg atttgggacc tcccccagtc cagctaagtc   1140
caccctggtg gagagccggt gttgcagaga cttgatggag gagaaatttg atcaggtgtg   1200
ccagtgggtg ctgaaatgca ggaatagcaa gaactcgctg atccaaatga caatccttaa   1260
tttgttgccc cgcttggctg cattccgacc ttctgccttc acagataccc agtatctcca   1320
agataccatg aaccatgtcc taagctgtgt caagaaggag aaggaacgta cagcggcctt   1380
ccaagccctg gggctacttt ctgtggctgt gaggtctgag tttaaggtct atttgcctcg   1440
cgtgctggac atcatccgag cggccctgcc cccaaaggac ttcgcccata gaggcagaa    1500
ggcaatgcag gtggatgcca cagtcttcac ttgcatcagc atgctggctc gagcaatggg   1560
gccaggcatc cagcaggata tcaaggagct gctggagccc atgctggcag tgggactaag   1620
ccctgccctc actgcagtgc tctacgacct gagccgtcag attccacagc taaagaagga   1680
cattcaagat gggctactga aaatgctgtc cctggtcctt atgcacaaac cccttcgcca   1740
cccaggcatg cccaagggcc tggcccatca gctggcctct cctggcctca cgaccctccc   1800
tgaggccagc gatgtgggca gcatcactct tgccctccga acgcttggca gctttgaatt   1860
tgaaggccac tctctgaccc aatttgttcg ccactgtgcg gatcattttcc tgaacagtga   1920
gcacaaggag atccgcatgg aggctgcccg cacctgctcc cgcctgctca cccctccat    1980
ccacctcatc agtggccatg ctcatgtggt tagccagacc gcagtgcaag tggtggcaga   2040
tgtgcttagc aaaactgctcg tagttgggat aacagatcct gaccctgaca ttcgctactg   2100
tgtcttggcg tccctggacg agcgcttttga tgcacacctg gcccaggcgg agaacttgca   2160
ggccttgttt gtggctctga atgaccaggt gttttgagatc cgggagctgg ccatctgcac   2220
tgtgggccga ctcagtagca tgaacccttgc cttttgtcatg cctttcctgc gcaagatgct   2280
catccagatt ttgacagagt tggagcacag tgggattgga agaatcaaag agcagagtgc   2340
ccgcatgctg gggcacctgg tctccaatgc cccccgactc atccgcccct acatggagcc   2400
tattctgaag gcattaattt tgaaactgaa agatccagac cctgatccaa acccaggtgt   2460
gatcaataat gtcctggcaa caataggaga attggcacag gttagtggcc tggaaatgag   2520
gaaatgggtt gatgaacttt ttattatcat catggacatg ctccaggatt cctctttgtt   2580
ggccaaaagg caggtggctc tgtggaccct gggacagttg gtggccagca ctggctatgt   2640
agtagagccc tacaggaagt accctacttt gcttgaggtg ctactgaatt ttctgaagac   2700
tgagcagaac cagggtacac gcagagaggc catccgtgtg ttagggcttt tagggctttt   2760
ggatccttac aagcacaaag tgaacattgg catgatagac cagtcccggg atgcctctgc   2820
tgtcagcctg tcagaatcca agtcaagtca ggattcctct gactatagca ctagtgaaat   2880
gctggtcaac atgggaaact gcctctggga tgagttctac ccagctgtgt ccatggtggc   2940
cctgatgcgg atcttccgag accagtcact ctctcatcat cacaccatgg ttgtccaggc   3000
catcaccttc atcttcaagt ccctgggact caaatgtgtg cagttcctgc ccaggtcat    3060
gcccacgttc cttaacgtca ttcgagtctg tgatggggcc atccgggaat ttttgttcca   3120
gcagctggga atgttggtgt cctttgtgaa gagccacatc agaccttata tggatgaaat   3180
agtcaccctc atgagagaat tctgggtcat gaacacctca attcagagca cgatcattct   3240
```

```
tctcattgag caaattgtgg tagctcttgg gggtgaattt aagctctacc tgccccagct     3300
gatcccacac atgctgcgtg tcttcatgca tgacaacagc ccaggccgca ttgtctctat     3360
caagttactg gctgcaatcc agctgtttgg cgccaacctg gatgactacc tgcatttact     3420
gctgcctcct attgttaagt tgtttgatgc ccctgaagct ccactgccat ctcgaaaggc     3480
agcgctagag actgtggacc gcctgacgga gtccctggat ttcactgact atgcctcccg     3540
gatcattcac cctattgttc gaacactgga ccagagccca gaactgcgct ccacagccat     3600
ggacacgctg tcttcacttg ttttcagct ggggaagaag taccaaattt tcattccaat     3660
ggtgaataaa gttctggtgc gacaccgaat caatcatcag cgctatgatg tgctcatctg     3720
cagaattgtc aagggataca cacttgctga tgaagaggag gatcctttga tttaccagca     3780
tcggatgctt aggagtggcc aaggggatgc attggctagt ggaccagtgg aaacaggacc     3840
catgaagaaa ctgcacgtca gcaccatcaa cctccaaaag gcctggggcg ctgccaggag     3900
ggtctccaaa gatgactggc tggaatggct gagacggctg agcctggagc tgctgaagga     3960
ctcatcatcg ccctccctgc gctcctgctg ggccctggca caggcctaca acccgatggc     4020
cagggatctc ttcaatgctg catttgtgtc ctgctggtct gaactgaatg aagatcaaca     4080
ggatgagctc atcagaagca tcgagttggc cctcacctca caagacatcg ctgaagtcac     4140
acagaccctc ttaaacttgg ctgaattcat ggaacacagt gacaagggcc ccctgccact     4200
gagagatgac aatggcattg ttctgctggg tgagagagct gccaagtgcc gagcatatgc     4260
caaagcacta cactacaaag aactggagtt ccagaaaggc cccaccctg ccattctaga     4320 atctctcatc agcattaata ataagctaca gcagccggag gcagcggccg gagtgttaga     4380
atatgccatg aaacactttg gagagctgga gatccaggct acctggtatg agaaactgca     4440
cgagtgggag gatgcccttg tggcctatga caagaaaatg gacaccaaca aggacgaccc     4500
agagctgatg ctgggccgca tgcgctgcct cgaggccttg ggggaatggg gtcaactcca     4560
ccagcagtgc tgtgaaaagt ggaccctggt taatgatgag acccaagcca agatggcccg     4620
gatggctgct gcagctgcat ggggtttagg tcagtgggac agcatggaag aatacacctg     4680
tatgatccct cgggacaccc atgatggggc attttataga gctgtgctgg cactgcatca     4740
ggacctcttc tccttggcac aacagtgcat tgacaaggcc agggacctgc tggatgctga     4800
attaactgcg atggcaggag agagttacag tcgggcatat ggggcatgg ttttcttgcca     4860 catgctgtcc gagctggagg aggttatcca gtacaaactt gtccccgagc gacgagagat     4920
catccgccag atctggtggg agagactgca gggctgccag cgtatcgtag aggactggca     4980
gaaaatcctt atggtgcggt cccttgtggt cagccctcat gaagacatga gaacctggct     5040
caagtatgca gcctgtgcg gcaagagtgg caggctggcc cttgctcata aactttagt     5100 gttgctcctg ggagttgatc cgtctcggca acttgaccat cctctgccaa cagttcaccc     5160
tcaggtgacc tatgcctaca tgaaaaacat gtggaagagt gcccgcaaga tcgatgcctt     5220
ccagcacatg cagcattttg tccagaccat gcagcaacag gcccagcatg ccatcgctac     5280
tgaggaccag cagcataagc aggaactgca caagctcatg gcccgatgct tcctgaaact     5340
tggagagtgg cagctgaatc tacagggcat caatgagagc acaatcccca agtgctgca     5400 gtactacagc gccgccacag agcacgaccg cagctggtac aaggcctggc atgcgtgggc     5460
agtgatgaac ttcgaagctg tgctacacta caaacatcag aaccaagccc gcgatgagaa     5520
gaagaaactg cgtcatgcca gcggggccaa catcaccaac gccaccactg ccgccaccac     5580
ggccgccact gccaccacca ctgccagcac cgagggcagc aacagtgaga gcgaggccga     5640
```

```
gagcaccgag aacagcccca ccccatcgcc gctgcagaag aaggtcactg aggatctgtc    5700
caaaaccctc ctgatgtaca cggtgcctgc cgtccaggcg ttcttccgtt ccatctcctt    5760
gtcacgaggc aacaacctcc aggatacact cagagttctc accttatggt ttgattatgg    5820
tcactggcca gatgtcaatg aggccttagt ggaggggtg aaagccatcc agattgatac     5880
ctggctacag gttatacctc agctcattgc aagaattgat acgcccagac ccttggtggg    5940
acgtctcatt caccagcttc tcacagacat tggtcggtac caccccagg ccctcatcta     6000 cccactgaca gtggcttcta agtctaccac gacagcccgg cacaatgcag ccaacaagat    6060
tctgaagaac atgtgtgagc acagcaacac cctggtccag caggccatga tggtgagcga    6120
ggagctgatc cgagtggcca tcctctggca tgagatgtgg catgaaggcc tggaagaggc    6180
atctcgtttg tactttgggg aaaggaacgt gaaaggcatg tttgaggtgc tggagccctt    6240
gcatgctatg atggaacggg gccccagac tctgaaggaa acatccttta atcaggccta     6300
tggtcgagat ttaatggagg cccaagagtg gtgcaggaag tacatgaaat cagggaatgt    6360
caaggacctc acccaagcct gggacctcta ttatcatgtg ttccgacgaa tctcaaagca    6420
gctgcctcag ctcacatcct tagagctgca atatgtttcc ccaaaacttc tgatgtgccg    6480
ggaccttgaa ttggctgtgc caggaacata tgaccccaac cagccaatca ttcgcattca    6540
gtccatagca ccgtctttgc aagtcatcac atccaagcag aggcccccgga aattgacact    6600 tatgggcagc aacggacatg agtttgtttt ccttctaaaa ggccatgaag atctgcgcca    6660
ggatgagcgt gtgatgcagc tcttcggcct ggttaacacc cttctggcca atgacccaac    6720
atctcttcgg aaaaacctca gcatccagag atacgctgtc atccctttat cgaccaactc    6780
gggcctcatt ggctgggttc cccactgtga cacactgcac gccctcatcc gggactacag    6840
ggagaagaag aagatccttc tcaacatcga gcatcgcatc atgttgcgga tggctccgga    6900
ctatgaccac ttgactctga tgcagaaggt ggaggtgttt agcatgccg tcaataatac      6960 agctggggac gacctggcca agctgctgtg gctgaaaagc cccagctccg aggtgtggtt    7020
tgaccgaaga accaattata cccgttcttt agcggtcatg tcaatggttg ggtatatttt    7080
aggcctggga gatagacacc catccaacct gatgctggac cgtctgagtg gaagatcct     7140 gcacattgac tttggggact gctttgaggt tgctatgacc cgagagaagt tccagagaa     7200 gattccattt agactaacaa gaatgttgac caatgctatg gaggttacag gcctggatgg    7260
caactacaga atcacatgcc acacagtgat ggaggtgctg cgagagcaca aggacagtgt    7320
catggccgtg ctgaagcct tgtctatga cccttgctg aactggaggc tgatggacac      7380
aaataccaaa ggcaacaagc gatcccgaac gaggacggat tcctactctg ctggccagtc    7440
agtcgaaatt ttggacggtg tggaacttgg agagccagcc cataagaaaa cggggaccac    7500
agtgccagaa tctattcatt cttttcattgg agacggtttg gtgaaaccag aggccctaaa    7560
taagaaagct atccagatta ttaacagggt tcgagataag ctcactggtc gggacttctc    7620
tcatgatgac actttggatg ttccaacgca agttgagctg ctcatcaaac aagcgacatc    7680
ccatgaaaac ctctgccagt gctatattgg ctggtgccct ttctggtaac tggaggccca    7740
gatgtgccca tcacgttttt tctgaggctt ttgtacttta gtaaatgctt ccactaaact    7800
gaaaccatgg tgagaaagtt tgactttgtt aaatattttg aaatgtaaat gaaaagaact    7860
actgtatatt aaaagttggt ttgaaccaac tttctagctg ctgttgaaga atatatttgtc   7920 agaaacacaa ggcttgattt ggttcccagg acagtgaaac aatagtaata ccacgtaaat    7980
caagccattc attttgggga acagaagatc cataactttta gaaatacggg ttttgactta    8040
```

| | | | | |
|---|---|---|---|---|
| actcacaaga | gaactcatca | taagtacttg | ctgatggaag | aatgacctag | ttgctcctct | 8100 |
| caacatgggt | acagcaaact | cagcacagcc | aagaagcctc | aggtcgtgga | gaacatggat | 8160 |
| taggatccta | gactgtaaag | acacagaaga | tgctgacctc | accctgcca | cctatcccaa | 8220 |
| gacctcactg | gtctgtggac | agcagcagaa | atgtttgcaa | gataggccaa | aatgagtaca | 8280 |
| aaaggtctgt | cttccatcag | acccagtgat | gctgcgactc | acacgcttca | attcaagacc | 8340 |
| tgaccgctag | tagggaggtt | tattcagatc | gctggcagcc | tcggctgagc | agatgcacag | 8400 |
| aggggatcac | tgtgcagtgg | gaccaccctc | actggccttc | tgcagcaggg | ttctgggatg | 8460 |
| ttttcagtgg | tcaaaatact | ctgtttagag | caagggctca | gaaaacagaa | atactgtcat | 8520 |
| ggaggtgctg | aacacaggga | aggtctggta | catattggaa | attatgagca | gaacaaatac | 8580 |
| tcaactaaat | gcacaaagta | taaagtgtag | ccatgtctag | acaccatgtt | gtatcagaat | 8640 |
| aattttttgtg | ccaataaatg | acatcagaat | tttaaacata | | | 8680 |

<210> SEQ ID NO 5
<211> LENGTH: 5572
<212> TYPE: DNA
<213> ORGANISM: Homo sapiens

<400> SEQUENCE: 5

| | | | | | | |
|---|---|---|---|---|---|---|
| cctccctcg | cccggcgcgg | tcccgtccgc | ctctcgctcg | cctcccgcct | cccctcggtc | 60 |
| ttccgaggcg | cccgggctcc | cggcgcggcg | gcggagggg | cggcaggcc | ggcgggcggt | 120 |
| gatgtggcgg | gactctttat | gcgctgcggc | aggatacgcg | ctcggcgctg | ggacgcgact | 180 |
| gcgctcagtt | ctctcctctc | ggaagctgca | gccatgatgg | aagtttgaga | gttgagccgc | 240 |
| tgtgaggcga | ggccgggctc | aggcgaggga | gatgagagac | ggcggcggcc | gcggcccgga | 300 |
| gcccctctca | gcgcctgtga | gcagccgcgg | gggcagcgcc | ctcggggagc | cggccggcct | 360 |
| gcggcggcgg | cagcggcggc | gtttctcgcc | tcctcttcgt | cttttctaac | cgtgcagcct | 420 |
| cttcctcggc | ttctcctgaa | agggaaggtg | gaagccgtgg | gctcgggcgg | gagccggctg | 480 |
| aggcgcggcg | gcggcggcgg | cacctcccgc | tcctggagcg | gggggagaa | gcggcggcgg | 540 |
| cggcggccgc | ggcggctgca | gctccaggga | gggggtctga | gtcgcctgtc | accatttcca | 600 |
| gggctgggaa | cgccggagag | ttggtctctc | cccttctact | gcctccaaca | cggcggcggc | 660 |
| ggcggcggca | catccaggga | cccgggccgg | ttttaaacct | cccgtccgcc | gccgccgcac | 720 |
| cccccgtggc | ccgggctccg | gaggccgccg | gcggaggcag | ccgttcggag | gattattcgt | 780 |
| cttctcccca | ttccgctgcc | gccgctgcca | ggcctctggc | tgctgaggag | aagcaggccc | 840 |
| agtcgctgca | accatccagc | agccgccgca | gcagccatta | cccggctgcg | gtccagagcc | 900 |
| aagcggcggc | agagcgaggg | gcatcagcta | ccgccaagtc | cagagccatt | ccatcctgc | 960 |
| agaagaagcc | ccgccaccag | cagcttctgc | catctctctc | ctccttttc | ttcagccaca | 1020 |
| ggctcccaga | catgacagcc | atcatcaaag | agatcgttag | cagaaacaaa | aggagatatc | 1080 |
| aagaggatgg | attcgactta | gacttgacct | atatttatcc | aaacattatt | gctatgggat | 1140 |
| ttcctgcaga | aagacttgaa | ggcgtataca | ggaacaatat | tgatgatgta | gtaaggtttt | 1200 |
| tggattcaaa | gcataaaaac | cattacaaga | tatacaatct | ttgtgctgaa | agacattatg | 1260 |
| acaccgccaa | atttaattgc | agagttcac | aatatccttt | tgaagaccat | aacccaccac | 1320 |
| agctagaact | tatcaaaccc | ttttgtgaag | atcttgacca | atggctaagt | gaagatgaca | 1380 |
| atcatgttgc | agcaattcac | tgtaaagctg | gaaaggacg | aactggtgta | atgatatgtg | 1440 |
| catatttatt | acatcggggc | aaattttaa | aggcacaaga | ggcctagat | ttctatgggg | 1500 |

```
aagtaaggac cagagacaaa aagggagtaa ctattcccag tcagaggcgc tatgtgtatt    1560
attatagcta cctgttaaag aatcatctgg attatagacc agtggcactg ttgtttcaca    1620
agatgatgtt tgaaactatt ccaatgttca gtggcggaac ttgcaatcct cagtttgtgg    1680
tctgccagct aaaggtgaag atatattcct ccaattcagg acccacacga cgggaagaca    1740
agttcatgta ctttgagttc cctcagccgt tacctgtgtg tggtgatatc aaagtagagt    1800
tcttccacaa acagaacaag atgctaaaaa aggacaaaat gtttcacttt tgggtaaata    1860
cattcttcat accaggacca gaggaaacct cagaaaagt agaaaatgga agtctatgtg     1920
atcaagaaat cgatagcatt tgcagtatag agcgtgcaga taatgacaag gaatatctag    1980
tacttacttt aacaaaaaat gatcttgaca aagcaaataa agacaaagcc aaccgatact    2040
tttctccaaa ttttaaggtg aagctgtact tcacaaaaac agtagaggag ccgtcaaatc    2100
cagaggctag cagttcaact tctgtaacac cagatgttag tgacaatgaa cctgatcatt    2160
atagatattc tgacaccact gactctgatc cagagaatga accttttgat gaagatcagc    2220
atacacaaat tacaaaagtc tgaatttttt tttatcaaga gggataaaac accatgaaaa    2280
taaacttgaa taaactgaaa atggacccttt tttttttaa tggcaatagg acattgtgtc    2340
agattaccag ttataggaac aattctcttt tcctgaccaa tcttgtttta ccctatacat     2400
ccacagggtt ttgacacttg ttgtccagtt gaaaaaggt tgtgtagctg tgtcatgtat      2460
ataccttttt gtgtcaaaag gacatttaaa attcaattag gattaataaa gatggcactt    2520
tcccgtttta ttccagtttt ataaaaagtg gagacagact gatgtgtata cgtaggaatt    2580
ttttcctttt gtgttctgtc accaactgaa gtggctaaag agctttgtga tatactggtt    2640
cacatcctac ccctttgcac ttgtggcaac agataagttt gcagttggct aagagaggtt    2700
tccgaagggt tttgctacat tctaatgcat gtattcgggt taggggaatg gagggaatgc    2760
tcagaaagga ataattttta tgctggactc tggaccatat accatctcca gctatttaca    2820
cacacctttc tttagcatgc tacagttatt aatctggaca ttcgaggaat tggccgctgt    2880
cactgcttgt tgtttgcgca ttttttttta aagcatattg gtgctagaaa aggcagctaa    2940
aggaagtgaa tctgtattgg ggtacaggaa tgaaccttct gcaacatctt aagatccaca    3000
aatgaaggga tataaaaata atgtcatagg taagaaacac agcaacaatg acttaaccat    3060
ataaatgtgg aggctatcaa caaagaatgg gcttgaaaca ttataaaaat tgacaatgat    3120
ttattaaata tgttttctca attgtaacga cttctccatc tcctgtgtaa tcaaggccag    3180
tgctaaaatt cagatgctgt tagtacctac atcagtcaac aacttacact tattttacta    3240
gttttcaatc ataataccctg ctgtggatgc ttcatgtgct gcctgcaagc ttcttttttc    3300
tcattaaata taaatatttt tgtaatgctg cacagaaatt ttcaatttga gattctacag    3360
taagcgtttt ttttctttga agatttatga tgcacttatt caatagctgt cagccgttcc    3420
acccttttga ccttacacat tctattacaa tgaattttgc agttttgcac atttttttaaa    3480 tgtcattaac tgttagggaa ttttacttga atactgaata catataatgt ttatattaaa    3540
aaggacattt gtgttaaaaa ggaaattaga gttgcagtaa actttcaatg ctgcacacaa    3600
aaaaaagaca tttgattttt cagtagaaat tgtcctacat gtgctttatt gatttgctat    3660
tgaaagaata gggtttttt ttttttttttt ttttttttttt ttaaatgtgc agtgttgaat    3720
catttcttca tagtgctccc ccgagttggg actagggctt caatttcact tcttaaaaaa    3780
aatcatcata tatttgatat gcccagactg catacgattt taagcggagt acaactacta    3840
ttgtaaagct aatgtgaaga tattattaaa aaggtttttt tttccagaaa tttggtgtct    3900
```

```
tcaaattata ccttcacctt gacatttgaa tatccagcca ttttgtttct taatggtata    3960
aaattccatt ttcaataact tattggtgct gaaattgttc actagctgtg gtctgaccta    4020
gttaatttac aaatacagat tgaataggac ctactagagc agcatttata gagtttgatg    4080
gcaaatagat taggcagaac ttcatctaaa atattcttag taaataatgt tgacacgttt    4140 tccataccttt gtcagtttca ttcaacaatt tttaaatttt taacaaagct cttaggattt    4200
acacatttat atttaaacat tgatatatag agtattgatt gattgctcat aagttaaatt    4260
ggtaaagtta gagacaacta ttctaacacc tcaccattga aatttatatg ccaccttgtc    4320
tttcataaaa gctgaaaatt gttacctaaa atgaaaatca acttcatgtt ttgaagatag    4380
ttataaatat tgttctttgt tacaatttcg ggcaccgcat attaaaacgt aactttattg    4440
ttccaatatg taacatggag ggccaggtca taaataatga cattataatg ggcttttgca    4500
ctgttattat ttttccttttg gaatgtgaag gtctgaatga gggttttgat tttgaatgtt    4560
tcaatgtttt tgagaagcct tgcttacatt ttatggtgta gtcattggaa atggaaaaat    4620
ggcattatat atattatata tataaatata tattatacat actctcctta ctttatttca    4680
gttaccatcc ccatagaatt tgacaagaat tgctatgact gaaaggtttt cgagtcctaa    4740 ttaaacttt atttatggca gtattcataa ttagcctgaa atgcattctg taggtaatct    4800
ctgagtttct ggaatatttt cttagacttt ttggatgtgc agcagcttac atgtctgaag    4860
ttacttgaag gcatcacttt taagaaagct tacagttggg ccctgtacca tcccaagtcc    4920
tttgtagctc ctcttgaaca tgtttgccat acttttaaaa gggtagttga ataaatagca    4980
tcaccattct ttgctgtggc acaggttata aacttaagtg gagtttaccg gcagcatcaa    5040
atgtttcagc tttaaaaaat aaaagtaggg tacaagttta atgtttagtt ctagaaattt    5100
tgtgcaatat gttcataacg atggctgtgg ttgccacaaa gtgcctcgtt tacctttaaa    5160
tactgttaat gtgtcatgca tgcagatgga aggggtggaa ctgtgcacta aagtgggggc    5220
tttaactgta gtatttggca gagttgcctt ctacctgcca gttcaaaagt tcaacctgtt    5280
ttcatataga atatatatac taaaaaattt cagtctgtta aacagcctta ctctgattca    5340
gcctcttcag atactcttgt gctgtgcagc agtggctctg tgtgtaaatg ctatgcactg    5400
aggatacaca aaaataccaa tatgatgtgt acaggataat gcctcatccc aatcagatgt    5460
ccatttgtta ttgtgtttgt taacaaccct ttatctctta gtgttataaa ctccacttaa    5520
aactgattaa agtctcattc ttgtcaaaaa aaaaaaaaa aaaaaaaaaa aa    5572
```

<210> SEQ ID NO 6
<211> LENGTH: 2222
<212> TYPE: DNA
<213> ORGANISM: Homo sapiens

<400> SEQUENCE: 6

```
attcggcacg agggaggaag cgagaggtgc tgccctcccc ccggagttgg aagcgcgtta      60
cccgggtcca aaatgcccaa gaagaagccg acgcccatcc agctgaaccc ggcccccgac     120
ggctctgcag ttaacgggac cagctctgcg gagaccaact tggaggcctt gcagaagaag     180
ctggaggagc tagagcttga tgagcagcag cgaaagcgcc ttgaggcctt tcttacccag     240
aagcagaagg tgggagaact gaaggatgac gactttgaga agatcagtga gctgggggct     300
ggcaatggcg gtgtggtgtt caaggtctcc cacaagcctt ctggcctggt catggccaga     360
aagctaattc atctggagat caaacccgca atccggaacc agatcataag ggagctgcag     420
gttctgcatg agtgcaactc tccgtacatc gtgggcttct atggtgcgtt ctacagcgat     480
```

-continued

| | |
|---|---|
| ggcgagatca gtatctgcat ggagcacatg gatggaggtt ctctggatca agtcctgaag | 540 |
| aaagctggaa gaattcctga acaaatttta ggaaaagtta gcattgctgt aataaaaggc | 600 |
| ctgacatatc tgagggagaa gcacaagatc atgcacagag atgtcaagcc ctccaacatc | 660 |
| ctagtcaact cccgtgggga gatcaagctc tgtgactttg ggtcagcgg gcagctcatc | 720 |
| gactccatgg ccaactcctt cgtgggcaca aggtcctaca tgtcgccaga aagactccag | 780 |
| gggactcatt actctgtgca gtcagacatc tggagcatgg gactgtctct ggtagagatg | 840 |
| gcggttggga ggtatcccat ccctcctcca gatgccaagg agctggagct gatgtttggg | 900 |
| tgccaggtgg aaggagatgc ggctgagacc ccacccaggc caaggacccc cgggaggccc | 960 |
| cttagctcat acggaatgga cagccgacct cccatggcaa ttttgagtt gttggattac | 1020 |
| atagtcaacg agcctcctcc aaaactgccc agtggagtgt tcagtctgga atttcaagat | 1080 |
| tttgtgaata atgcttaat aaaaaacccc gcagagagag cagatttgaa gcaactcatg | 1140 |
| gttcatgctt ttatcaagag atctgatgct gaggaagtgg atttttgcagg ttggctctgc | 1200 |
| tccaccatcg gccttaacca gcccagcaca ccaacccatg ctgctggcgt ctaagtgttt | 1260 |
| gggaagcaac aaagagcgag tcccctgccc ggtggtttgc catgtcgctt ttgggcctcc | 1320 |
| ttcccatgcc tgtctctgtt cagatgtgca tttcacctgt gacaaaggat gaagaacaca | 1380 |
| gcatgtgcca agattctact cttgtcattt taatattac tgtctttatt cttattacta | 1440 |
| ttattgttcc cctaagtgga ttggctttgt gcttggggct atttgtgtgt atgctgatga | 1500 |
| tcaaaacctg tgccaggctg aattacagtg aaattttttgg tgaatgtggg tagtcattct | 1560 |
| tacaattgca ctgctgttcc tgctccatga ctggctgtct gcctgtattt tcggactttg | 1620 |
| acatttgaca tttggtggac tttatccttgc tgggcatact ttctctctag gagggagcct | 1680 |
| tgtgagatcc ttcacaggca gtgcatgtga agcatgcttt gctgctatga aaatgagcat | 1740 |
| cagagagtgt acatcatgtt attttattat tattatttgc ttttcatgta gaactcagca | 1800 |
| gttgacatcc aaatctagcc agagcccttc actgccatga tagctggggc ttcaccagtc | 1860 |
| tgtctactgt ggtgatctgt agacttctgg ttgtatttct atatttattt tcagtatact | 1920 |
| gtgtgggata cttagtggta tgtctcttta agttttgatt aatgtttctt aaatggaatt | 1980 |
| atttgaatgt cacaaattga tcaagatatt aaaatgtcgg atttatcttt ccccatatcc | 2040 |
| aagtaccaat gctgttgtaa acaacgtgta tagtgcctaa aattgtatga aaatcctttt | 2100 |
| aaccatttta acctagatgt ttaacaaatc taatctctta ttctaataaa tatactatga | 2160 |
| aataaaaaa aaggagaaa gctaaaaaaa aaaaaaaaa aaaaaaaaa aaaaaaaaa | 2220 |
| aa | 2222 |

<210> SEQ ID NO 7
<211> LENGTH: 5916
<212> TYPE: DNA
<213> ORGANISM: Homo sapiens

<400> SEQUENCE: 7

| | |
|---|---|
| gcccctccct ccgcccgccc gccggcccgc ccgtcagtct ggcaggcagg caggcaatcg | 60 |
| gtccgagtgg ctgtcggctc ttcagctctc ccgctcggcg tcttccttcc tcctcccggt | 120 |
| cagcgtcggc ggctgcaccg gcggcggcgc agtccctgcg ggaggggcga caagagctga | 180 |
| gcggcggccg ccgagcgtcg agctcagcgc ggcggaggcg gcggcggccc ggcagccaac | 240 |
| atggcggcgg cggcgcggc gggcgcgggc ccggagatgg tccgcgggca ggtgttcgac | 300 |
| gtggggcccg gctacaccaa cctctcgtac atcggcgagg gcgcctacgg catggtgtgc | 360 |

```
tctgcttatg ataatgtcaa caaagttcga gtagctatca agaaaatcag cccctttgag    420
caccagacct actgccagag aaccctgagg gagataaaaa tcttactgcg cttcagacat    480
gagaacatca ttggaatcaa tgacattatt cgagcaccaa ccatcgagca aatgaaagat    540
gtatatatag tacaggacct catggaaaca gatctttaca agctcttgaa gacacaacac    600
ctcagcaatg accatatctg ctattttctc taccagatcc tcagagggtt aaaatatatc    660
cattcagcta acgttctgca ccgtgacctc aagccttcca acctgctgct caacaccacc    720
tgtgatctca agatctgtga ctttggcctg gcccgtgttg cagatccaga ccatgatcac    780
acagggttcc tgacagaata tgtggccaca cgttggtaca gggctccaga aattatgttg    840
aattccaagg gctacaccaa gtccattgat atttggtctg taggctgcat tctggcagaa    900
atgctttcta acaggcccat ctttccaggg aagcattatc ttgaccagct gaaccacatt    960
ttgggtattc ttggatcccc atcacaagaa gacctgaatt gtataataaa tttaaaagct   1020
aggaactatt tgctttctct tccacacaaa ataaggtgc catggaacag gctgttccca    1080
aatgctgact ccaaagctct ggacttattg acaaaatgt tgacattcaa cccacacaag    1140
aggattgaag tagaacaggc tctggcccac ccatatctgg agcagtatta cgacccgagt   1200
gacgagccca tcgccgaagc accattcaag ttcgacatgg aattggatga cttgcctaag   1260
gaaaagctca agaactaat ttttgaagag actgctagat tccagccagg atacagatct   1320
taaatttgtc aggacaaggg ctcagaggac tggacgtgct cagacatcgg tgttcttctt   1380
cccagttctt gacccctggt cctgtctcca gccgtcttg gcttatccac tttgactcct   1440
ttgagccgtt tggaggggcg gtttctggta gttgtggctt ttatgctttc aaagaatttc   1500
ttcagtccag agaattcctc ctggcagccc tgtgtgtgtc acccattggt gacctgcggc   1560
agtatgtact tcagtgcacc tactgcttac tgttgcttta gtcactaatt gctttctggt   1620
ttgaaagatg cagtggttcc tccctctcct gaatcctttt ctacatgatg ccctgctgac   1680
catgcagccg caccagagag agattcttcc ccaattggct ctagtcactg gcatctcact   1740
ttatgatagg gaaggctact acctagggca cttttaagtca gtgacagccc cttatttgca   1800
cttcaccttt tgaccataac tgtttcccca gagcaggagc ttgtggaaat accttggctg   1860
atgttgcagc ctgcagcaag tgcttccgtc tccggaatcc ttggggagca cttgtccacg   1920
tcttttctca tatcatggta gtcactaaca tatataaggt atgtgctatt ggcccagctt   1980
ttagaaaatg cagtcatttt tctaaataaa aggaagtac tgcacccagc agtgtcactc    2040
tgtagttact gtggtcactt gtaccatata gaggtgtaac acttgtcaag aagcgttatg   2100
tgcagtactt aatgtttgta agacttacaa aaaagattt aaagtggcag cttcactcga    2160
catttggtga gagaagtaca aaggttgcag tgctgagctg tgggcggttt ctggggatgt   2220
cccagggtgg aactccacat gctggtgcat atacgcccct gagctacttc aaatgtgggt   2280
gtttcagtaa ccacgttcca tgcctgagga tttagcagag aggaacactg cgtctttaaa   2340
tgagaaagta tacaattctt tttccttcta cagcatgtca gcatctcaag ttcatttttc   2400
aacctacagt ataacaattt gtaataaagc ctccaggagc tcatgacgtg aagcactgtt   2460
ctgtcctcaa gtactcaaat atttctgata ctgctgagtc agactgtcag aaaaagctag   2520
cactaactcg tgtttggagc tctatccata ttttactgat ctctttaagt atttgttcct   2580
gccactgtgt actgtggagt tgactcggtg ttctgtccca gtgcggtgcc tcctcttgac   2640
ttccccactg ctctctgtgg tgagaaattt gccttgttca ataattactg taccctcgca   2700
tgactgttac agctttctgt gcagagatga ctgtccaagt gccacatgcc tacgattgaa   2760
```

```
atgaaaactc tattgttacc tctgagttgt gttccacgga aaatgctatc cagcagatca    2820
tttaggaaaa ataattctat ttttagcttt tcatttctca gctgtccttt tttcttgttt    2880 gattttgac agcaatggag aatgggttat ataaagactg cctgctaata tgaacagaaa     2940
tgcatttgta attcatgaaa ataaatgtac atcttctatc ttcacattca tgttaagatt    3000
cagtgttgct ttcctctgga tcagcgtgtc tgaatggaca gtcaggttca ggttgtgctg    3060
aacacagaaa tgctcacagg cctcactttg ccgcccaggc actggcccag cacttggatt    3120
tacataagat gagttagaaa ggtacttctg tagggtcctt tttacctctg ctcggcagag    3180
aatcgatgct gtcatgttcc tttattcaca atcttaggtc tcaaatattc tgtcaaaccc    3240
taacaaagaa gccccgacat ctcaggttgg attccctggt tctctctaaa gagggcctgc    3300
ccttgtgccc cagaggtgct gctgggcaca gccaagagtt gggaagggcc gccccacagt    3360
acgcagtcct caccacccag cccagggtgc tcacgctcac cactcctgtg gctgaggaag    3420
gatagctggc tcatcctcgg aaaacagacc cacatctcta ttcttgccct gaaatacgcg    3480
cttttcactt gcgtgctcag agctgccgtc tgaaggtcca cacagcattg acgggacaca    3540
gaaatgtgac tgttaccgga taacactgat tagtcagttt tcatttataa aaaagcattg    3600
acagttttat tactcttgtt tcttttttaaa tggaaagtta ctattataag gttaatttgg    3660
agtcctcttc taaatagaaa accatatcct tggctactaa catctggaga ctgtgagctc    3720
cttcccattc cccttcctgg tactgtggag tcagattggc atgaaaccac taacttcatt    3780
ctagaatcat tgtagccata agttgtgtgc tttttattaa tcatgccaaa cataatgtaa    3840
ctgggcagag aatggtccta accaaggtac ctatgaaaag cgctagctat catgtgtagt    3900
agatgcatca ttttggctct tcttacattt gtaaaaatgt acagattagg tcatcttaat    3960
tcatattagt gacacggaac agcacctcca ctatttgtat gttcaaataa gctttcagac    4020
taatagcttt tttggtgtct aaaatgtaag caaaaaattc ctgctgaaac attccagtcc    4080
tttcatttag tataaaagaa atactgaaca agccagtggg atggaattga aagaactaat    4140
catgaggact ctgtcctgac acaggtcctc aaagctagca gagatacgca gacattgtgg    4200
catctgggta aagaatact gtattgtgtg tgcagtgcac agtgtgtggt gtgtgcacac     4260
tcattccttc tgctcttggg cacaggcagt gggtgtagag gtaaccagta gctttgagaa    4320
gctacatgta gctcaccagt ggttttctct aaggaatcac aaaagtaaac tacccaacca    4380
catgccacgt aatatttcag ccattcagag gaaactgttt tctctttatt tgcttatatg    4440
ttaatatggt ttttaaattg gtaacttta tatagtatgg taacagtatg ttaatacaca     4500
catacatacg cacacatgct ttgggtcctt ccataatact tttatatttg taaatcaatg    4560
ttttggagca atcccaagtt taagggaaat attttttgtaa atgtaatggt tttgaaaatc   4620
tgagcaatcc ttttgcttat acatttttaa agcatttgtg ctttaaaatt gttatgctgg    4680
tgtttgaaac atgatactcc tgtggtgcag atgagaagct ataacagtga atatgtggtt    4740
tctcttacgt catccacctt gacatgatgg gtcagaaaca aatggaaatc cagagcaagt    4800
cctccagggt tgcaccaggt ttacctaaag cttgttgcct tttcttgtgc tgtttatgcg    4860
tgtagagcac tcaagaaagt tctgaaactg ctttgtatct gctttgtact gttggtgcct    4920
tcttggtatt gtaccccaaa attctgcata gattatttag tataatggta agttaaaaaa    4980
tgttaaagga agatttttatt aagaatctga atgtttattc attatattgt tacaatttaa   5040
cattaacatt tatttgtggt atttgtgatt tggttaatct gtataaaaat tgtaagtaga    5100
aaggtttata tttcatctta attcttttga tgttgtaaac gtacttttta aaagatggat    5160
```

| tatttgaatg tttatggcac ctgacttgta aaaaaaaaaa actacaaaaa aatccttaga | 5220 |
| atcattaaat tgtgtccctg tattaccaaa ataacacagc accgtgcatg tatagtttaa | 5280 |
| ttgcagtttc atctgtgaaa acgtgaaatt gtctagtcct tcgttatgtt ccccagatgt | 5340 |
| cttccagatt tgctctgcat gtggtaactt gtgttagggc tgtgagctgt tcctcgagtt | 5400 |
| gaatggggat gtcagtgctc ctagggttct ccaggtggtt cttcagacct tcacctgtgg | 5460 |
| ggggggggt aggcggtgcc cacgcccatc tcctcatcct cctgaacttc tgcaacccca | 5520 |
| ctgctgggca gacatcctgg gcaacccctt ttttcagagc aagaagtcat aaagatagga | 5580 |
| tttcttggac atttggttct tatcaatatt gggcattatg taatgactta tttacaaaac | 5640 |
| aaagatactg gaaatgtttt tggatgtggt gttatggaaa gagcacaggc cttgaccca | 5700 |
| tccagctggg ttcagaacta cccctgctt ataactgcgg ctggctgtgg gccagtcatt | 5760 |
| ctgcgtctct gctttcttcc tctgcttcag actgtcagct gtaaagtgga agcaatatta | 5820 |
| cttgccttgt atatggtaaa gattataaaa atacatttca actgttcagc atagtacttc | 5880 |
| aaagcaagta ctcagtaaat agcaagtctt tttaaa | 5916 |

<210> SEQ ID NO 8
<211> LENGTH: 2230
<212> TYPE: DNA
<213> ORGANISM: Homo sapiens

<400> SEQUENCE: 8

| cttggagaca acatgtggtt cttgacaact ctgctccttt gggttccagt tgatgggcaa | 60 |
| gtggacacca caaaggcagt gatcactttg cagcctccat gggtcagcgt gttccaagag | 120 |
| gaaaccgtaa ccttgcattg tgaggtgctc catctgcctg ggagcagctc tacacagtgg | 180 |
| tttctcaatg gcacagccac tcagacctcg accccagct acagaatcac ctctgccagt | 240 |
| gtcaatgaca gtggtgaata caggtgccag agaggtctct cagggcgaag tgaccccata | 300 |
| cagctggaaa tccacagagg ctggctacta ctgcaggtct ccagcagagt cttcacggaa | 360 |
| ggagaacctc tggccttgag gtgtcatgcg tggaaggata agctggtgta caatgtgctt | 420 |
| tactatcgaa atggcaaagc cttaagtttt ttccactgga attctaacct caccattctg | 480 |
| aaaaccaaca taagtcacaa tggcacctac cattgctcag gcatgggaaa gcatcgctac | 540 |
| acatcagcag gaatatctgt cactgtgaaa gagctatttc cagctccagt gctgaatgca | 600 |
| tctgtgacat ccccactcct ggaggggaat ctggtcaccc tgagctgtga aacaaagttg | 660 |
| ctcttgcaga ggcctggttt gcagctttac ttctcccttct acatgggcag caagaccctg | 720 |
| cgaggcagga acatcctc tgaataccaa atactaactg ctagaagaga agactctggg | 780 |
| ttatactggt gcgaggctgc cacagaggat ggaaatgtcc ttaagcgcag ccctgagttg | 840 |
| gagcttcaag tgcttggcct ccagttacca actcctgtct ggtttcatgt cctttctat | 900 |
| ctggcagtgg gaataatgtt tttagtgaac actgttctct gggtgacaat acgtaaagaa | 960 |
| ctgaaaagaa agaaaagtg ggatttagaa atctctttgg attctggtca tgagaagaag | 1020 |
| gtaatttcca gccttcaaga agacagacat ttagaagaag agctgaaatg tcaggaacaa | 1080 |
| aaagaagaac agctgcagga aggggtgcac cggaaggagc cccaggggc cacgtagcag | 1140 |
| cggctcagtg ggtggccatc gatctggacc gtccctgcc cacttgctcc ccgtgagcac | 1200 |
| tgcgtacaaa catccaaaag ttcaacaaca ccagaactgt gtgtctcatg gtatgtaact | 1260 |
| cttaaagcaa ataaatgaac tgacttcaac tgggatacat ttggaaatgt ggtcatcaaa | 1320 |
| gatgacttga aatgaggcct actctaaaga attcttgaaa aacttacaag tcaagcctag | 1380 |

| | |
|---|---|
| cctgataatc ctattacata gtttgaaaaa tagtatttta tttctcagaa caaggtaaaa | 1440 |
| aggtgagtgg gtgcatatgt acagaagatt aagacagaga acagacaga aagagacaca | 1500 |
| cacacagcca ggagtgggta gatttcaggg agacaagagg gaatagtata gacaataagg | 1560 |
| aaggaaaatag tacttacaaa tgactcctaa gggactgtga gactgagagg gctcacgcct | 1620 |
| ctgtgttcag gatacttagt tcatggcttt tctctttgac tttactaaaa gagaatgtct | 1680 |
| ccatacgcgt tctaggcata caaggggta actcatgatg agaaatggat gtgttattct | 1740 |
| tgccctctct tttgaggctc tctcataacc cctctatttc tagagacaac aaaaatgctg | 1800 |
| ccagtcctag gcccctgccc tgtaggaagg cagaatgtaa ctgttctgtt tgtttaacga | 1860 |
| ttaagtccaa atctccaagt gcggcactgc aaagagacgc ttcaagtggg gagaagcggc | 1920 |
| gataccatag agtccagatc ttgcctccag agatttgctt taccttcctg attttctggt | 1980 |
| tactaattag cttcaggata cgctgctctc atacttgggc tgtagtttgg agacaaaata | 2040 |
| ttttcctgcc actgtgtaac atagctgagg taaaaactga actatgtaaa tgactctact | 2100 |
| aaaagtttag ggaaaaaaaa caggaggagt atgacacaaa aaaaaaaaa aaaaaaaaa | 2160 |
| aaaaaaaaaa aaaaaaaaaa aaaaaaaaaa aaaaaaaaaa aaaaaaaaaa aaaaaaaaaa | 2220 |
| aaaaaaaaaa | 2230 |

<210> SEQ ID NO 9
<211> LENGTH: 5616
<212> TYPE: DNA
<213> ORGANISM: Homo sapiens

<400> SEQUENCE: 9

| | |
|---|---|
| ccccggcgca gcgcggccgc agcagcctcc gccccccgca cggtgtgagc gcccgacgcg | 60 |
| gccgaggcgg ccggagtccc gagctagccc cggcggccgc cgccgcccag accggacgac | 120 |
| aggccacctc gtcggcgtcc gcccgagtcc ccgcctcgcc gccaacgcca caaccaccgc | 180 |
| gcacggcccc ctgactccgt ccagtattga tcgggagagc cggagcgagc tcttcgggga | 240 |
| gcagcgatgc gaccctccgg gacggccggg gcagcgctcc tggcgctgct ggctgcgctc | 300 |
| tgcccggcga gtcgggctct ggaggaaaag aaagtttgcc aaggcacgag taacaagctc | 360 |
| acgcagttgg gcacttttga agatcatttt ctcagcctcc agaggatgtt caataactgt | 420 |
| gaggtggtcc ttgggaattt ggaaattacc tatgtgcaga ggaattatga tctttccttc | 480 |
| ttaaagacca tccaggaggt ggctggttat gtcctcattg ccctcaacac agtggagcga | 540 |
| attcctttgg aaaacctgca gatcatcaga ggaaatatgt actacgaaaa ttcctatgcc | 600 |
| ttagcagtct tatctaacta tgatgcaaat aaaaccggac tgaaggagct gcccatgaga | 660 |
| aatttacagg aaatcctgca tggcgccgtg cggttcagca caaccctgc cctgtgcaac | 720 |
| gtggagagca tccagtggcg ggacatagtc agcagtgact ttctcagcaa catgtcgatg | 780 |
| gacttccaga accacctggg cagctgccaa aagtgtgatc caagctgtcc aatgggagc | 840 |
| tgctggggtg caggagagga gaactgccag aaactgacca aaatcatctg tgcccagcag | 900 |
| tgctccgggc gctgccgtgg caagtccccc agtgactgct gccacaacca gtgtgctgca | 960 |
| ggctgcacag gccccccggga gagcgactgc ctggtctgcc gcaaattccg agacgaagcc | 1020 |
| acgtgcaagg acacctgccc cccactcatg ctctacaacc ccaccacgta ccagatggat | 1080 |
| gtgaacccg agggcaaata cagctttggt gccacctgcg tgaagaagtg tccccgtaat | 1140 |
| tatgtggtga cagatcacgg ctcgtgcgtc cgagcctgtg gggccgacag ctatgagatg | 1200 |
| gaggaagacg gcgtccgcaa gtgtaagaag tgcgaagggc cttgccgcaa agtgtgtaac | 1260 |

```
ggaataggta ttggtgaatt taaagactca ctctccataa atgctacgaa tattaaacac    1320
ttcaaaaact gcacctccat cagtggcgat ctccacatcc tgccggtggc atttaggggt    1380
gactccttca cacatactcc tcctctggat ccacaggaac tggatattct gaaaaccgta    1440
aaggaaatca cagggttttt gctgattcag gcttggcctg aaaacaggac ggacctccat    1500
gcctttgaga acctagaaat catacgcggc aggaccaagc aacatggtca gttttctctt    1560
gcagtcgtca gcctgaacat aacatccttg ggattacgct ccctcaagga gataagtgat    1620
ggagatgtga taatttcagg aaacaaaaat ttgtgctatg caaatacaat aaactggaaa    1680
aaactgtttg ggacctccgg tcagaaaacc aaaattataa gcaacagagg tgaaaacagc    1740
tgcaaggcca caggccaggt ctgccatgcc ttgtgctccc ccgagggctg ctggggcccg    1800
gagcccaggg actgcgtctc ttgccggaat gtcagccgag gcaggaatg cgtggacaag    1860 tgcaaccttc tggagggtga gccaagggag tttgtggaga actctgagtg catacagtgc    1920
cacccagagt gcctgcctca ggccatgaac atcacctgca caggacgggg accagacaac    1980
tgtatccagt gtgcccacta cattgacggc ccccactgcg tcaagacctg cccggcagga    2040
gtcatgggag aaaacaacac cctggtctgg aagtacgcag acgccggcca tgtgtgccac    2100
ctgtgccatc caaactgcac ctacggatgc actgggccag gtcttgaagg ctgtccaacg    2160
aatgggccta agatcccgtc catcgccact gggatggtgg gggcctcct cttgctgctg    2220 gtggtggccc tggggatcgg cctcttcatg cgaaggcgcc acatcgttcg gaagcgcacg    2280
ctgcggaggc tgctgcagga gagggagctt gtggagcctc ttacacccag tggagaagct    2340
cccaaccaag ctctcttgag gatcttgaag gaaactgaat tcaaaaagat caaagtgctg    2400
ggctccggtg cgttcggcac ggtgtataag ggactctgga tcccagaagg tgagaaagtt    2460
aaaattcccg tcgctatcaa ggaattaaga gaagcaacat ctccgaaagc caacaaggaa    2520
atcctcgatg aagcctacgt gatggccagc gtggacaacc ccacgtgtgt ccgcctgctg    2580
ggcatctgcc tcacctccac cgtgcagctc atcacgcagc tcatgccctt cggctgcctc    2640
ctggactatg tccgggaaca caaagacaat attggctccc agtacctgct caactggtgt    2700
gtgcagatcg caaagggcat gaactacttg gaggaccgtc gcttggtgca ccgcgacctg    2760
gcagccagga acgtactggt gaaaacaccg cagcatgtca agatcacaga ttttgggctg    2820
gccaaactgc tgggtgcgga agagaaagaa taccatgcag aaggaggcaa agtgccatc    2880 aagtggatgg cattggaatc aattttacac agaatctata cccaccagag tgatgtctgg    2940
agctacgggg tgaccgtttg ggagttgatg acctttggat ccaagccata tgacggaatc    3000
cctgccagcg agatctcctc catcctggag aaaggagaac gcctccctca gccacccata    3060
tgtaccatcg atgtctacat gatcatggtc aagtgctgga tgatagacgc agatagtcgc    3120
ccaaagttcc gtgagttgat catcgaattc tccaaaatgg cccgagaccc ccagcgctac    3180
cttgtcattc aggggatgaa agaatgcat ttgccaagtc ctacagactc caacttctac    3240
cgtgccctga tggatgaaga agacatggac gacgtggtgg atgccgacga gtacctcatc    3300
ccacagcagg gcttcttcag cagccccctcc acgtcacgga ctccctcct gagctctctg    3360 agtgcaacca gcaacaattc caccgtggct tgcattgata gaaatgggct gcaaagctgt    3420
cccatcaagg aagacagctt cttgcagcga tacagctcag accccacagg cgccttgact    3480
gaggacagca tagacgacac cttcctccca gtgcctgaat acataaacca gtccgttccc    3540
aaaaggcccg ctggctctgt gcagaatcct gtctatcaca atcagcctct gaaccccgcg    3600
cccagcagag acccacacta ccaggacccc cacagcactg cagtgggcaa ccccgagtat    3660
```

```
ctcaacactg tccagcccac ctgtgtcaac agcacattcg acagccctgc ccactgggcc   3720
cagaaaggca gccaccaaat tagcctggac aaccctgact accagcagga cttctttccc   3780
aaggaagcca agccaaatgg catctttaag ggctccacag ctgaaaatgc agaataccta   3840
agggtcgcgc cacaaagcag tgaatttatt ggagcatgac cacggaggat agtatgagcc   3900
ctaaaaatcc agactctttc gatacccagg accaagccac agcaggtcct ccatcccaac   3960
agccatgccc gcattagctc ttagacccac agactggttt tgcaacgttt acaccgacta   4020
gccaggaagt acttccacct cgggcacatt tgggaagtt gcattccttt gtcttcaaac    4080
tgtgaagcat ttacagaaac gcatccagca agaatattgt cccctttgagc agaaatttat   4140 cttccaaaga ggtatatttg aaaaaaaaaa aaagtatatg tgaggatttt tattgattgg    4200
ggatcttgga gttttcatt gtcgctattg attttttactt caatgggctc ttccaacaag    4260
gaagaagctt gctggtagca cttgctaccc tgagttcatc caggcccaac tgtgagcaag    4320
gagcacaagc cacaagtctt ccagaggatg cttgattcca gtggttctgc ttcaaggctt    4380
ccactgcaaa acactaaaga tccaagaagg ccttcatggc cccagcaggc cggatcggta    4440
ctgtatcaag tcatggcagg tacagtagga taagccactc tgtcccttcc tgggcaaaga    4500
agaaacggag gggatggaat tcttccttag acttactttt gtaaaaatgt ccccacggta    4560
cttactcccc actgatggac cagtggtttc cagtcatgag cgttagactg acttgtttgt    4620
cttccattcc attgttttga aactcagtat gctgcccctg tcttgctgtc atgaaatcag    4680
caagagagga tgacacatca ataataact cggattccag cccacattgg attcatcagc     4740
atttggacca atagcccaca gctgagaatg tggaatacct aaggatagca ccgcttttgt    4800
tctcgcaaaa acgtatctcc taatttgagg ctcagatgaa atgcatcagg tcctttgggg    4860
catagatcag aagactacaa aaatgaagct gctctgaaat ctcctttagc catcacccca    4920
accccccaaa attagtttgt gttacttatg gaagatagtt ttctcctttt acttcacttc    4980
aaaagctttt tactcaaaga gtatatgttc cctccaggtc agctgccccc aaaccccctc    5040
cttacgcttt gtcacacaaa aagtgtctct gccttgagtc atctattcaa gcacttacag    5100
ctctggccac aacagggcat tttacaggtg cgaatgacag tagcattatg agtagtgtgg    5160
aattcaggta gtaaatatga aactagggtt tgaaattgat aatgctttca caacatttgc    5220
agatgtttta gaaggaaaaa agttccttcc taaaataatt tctctacaat tggaagattg    5280
gaagattcag ctagttagga gcccacccttt tttcctaatc tgtgtgtgcc ctgtaacctg    5340
actggttaac agcagtcctt tgtaaacagt gtttaaact ctcctagtca atatccaccc     5400
catccaattt atcaaggaag aaatggttca gaaaatattt tcagcctaca gttatgttca    5460
gtcacacaca catacaaaat gttccttttg cttttaaagt aatttttgac tcccagatca    5520
gtcagagccc ctacagcatt gttaagaaag tatttgattt ttgtctcaat gaaaataaaa    5580
ctatattcat ttccactcta aaaaaaaaaa aaaaaa                              5616

<210> SEQ ID NO 10
<211> LENGTH: 4816
<212> TYPE: DNA
<213> ORGANISM: Homo sapiens

<400> SEQUENCE: 10
gttcccggat ttttgtgggc gcctgccccg cccctcgtcc ccctgctgtg tccatatatc      60
gaggcgatag ggttaaggga aggcggacgc ctgatgggtt aatgagcaaa ctgaagtgtt    120
ttccatgatc ttttttgagt cgcaattgaa gtaccacctc ccgagggtga ttgcttcccc    180
```

| | |
|---|---|
| atgcggggta gaacctttgc tgtcctgttc accactctac ctccagcaca gaatttggct | 240 |
| tatgcctact caatgtgaag atgatgagga tgaaaacctt tgtgatgatc cacttccact | 300 |
| taatgaatgg tggcaaagca aagctatatt caagaccaca tgcaaagcta ctccctgagc | 360 |
| aaagagtcac agataaaacg ggggcaccag tagaatggcc aggacaaacg cagtgcagca | 420 |
| cagagactca gaccctggca gccatgcctg cgcaggcagt gatgagagtg acatgtactg | 480 |
| ttgtggacat gcacaaaagt gagtgtgcac cggcacagac atgaagctgc ggctccctgc | 540 |
| cagtcccgag acccacctgg acatgctccg ccacctctac cagggctgcc aggtggtgca | 600 |
| gggaaacctg gaactcacct acctgccccac caatgccagc ctgtccttcc tgcaggatat | 660 |
| ccaggaggtg cagggctacg tgctcatcgc tcacaaccaa gtgaggcagg tcccactgca | 720 |
| gaggctgcgg attgtgcgag gcacccagct ctttgaggac aactatgccc tggccgtgct | 780 |
| agacaatgga gacccgctga caataccac ccctgtcaca ggggcctccc caggaggcct | 840 |
| gcgggagctg cagcttcgaa gcctcacaga gatcttgaaa ggaggggtct tgatccagcg | 900 |
| gaaccccag ctctgctacc aggacacgat tttgtggaag acatcttcc acaagaacaa | 960 |
| ccagctggct ctcacactga tagacaccaa ccgctctcgg gcctgccacc cctgttctcc | 1020 |
| gatgtgtaag ggctcccgct gctggggaga gagttctgag gattgtcaga gcctgacgcg | 1080 |
| cactgtctgt gccggtggct gtgcccgctg caagggccca ctgcccactg actgctgcca | 1140 |
| tgagcagtgt gctgccggct gcacgggccc caagcactct gactgcctgg cctgcctcca | 1200 |
| cttcaaccac agtggcatct gtgagctgca ctgcccagcc ctggtcacct acaacacaga | 1260 |
| cacgtttgag tccatgccca atcccgaggg ccggtataca ttcggcgcca gctgtgtgac | 1320 |
| tgcctgtccc tacaactacc tttctacgga cgtgggatcc tgcacccctcg tctgccccct | 1380 |
| gcacaaccaa gaggtgacag cagaggatgg aacacagcgg tgtgagaagt gcagcaagcc | 1440 |
| ctgtgcccga gtgtgctatg gtctgggcat ggagcacttg cgagaggtga gggcagttac | 1500 |
| cagtgccaat atccaggagt ttgctggctg caagaagatc tttgggagcc tggcatttct | 1560 |
| gccggagagc tttgatgggg acccagcctc caacactgcc ccgctccagc cagagcagct | 1620 |
| ccaagtgttt gagactctgg aagagatcac aggttaccta tacatctcag catggccgga | 1680 |
| cagcctgcct gacctcagcg tcttccagaa cctgcaagta atccggggac gaattctgca | 1740 |
| caatggcgcc tactcgctga ccctgcaagg gctgggcatc agctggctgg gctgcgctc | 1800 |
| actgagggaa ctgggcagtg gactggcccct catccaccat aacacccacc tctgcttcgt | 1860 |
| gcacacggtg ccctgggacc agctctttcg gaacccgcac caagctctgc tccacactgc | 1920 |
| caaccggcca gaggacgagt gtgtgggcga gggcctggcc tgccaccagc tgtgcgcccg | 1980 |
| agggcactgc tggggtccag ggcccaccca gtgtgtcaac tgcagccagt ccttcgggg | 2040 |
| ccaggagtgc gtggaggaat gccgagtact gcaggggctc cccagggagt atgtgaatgc | 2100 |
| caggcactgt ttgccgtgcc accctgagtg tcagccccag aatggctcag tgacctgttt | 2160 |
| tggaccggag gctgaccagt gtgtggcctg tgcccactat aaggaccctc ccttctgcgt | 2220 |
| ggcccgctgc cccagcggtg tgaaacctga cctctcctac atgcccatct ggaagtttcc | 2280 |
| agatgaggag ggcgcatgcc agccttgccc catcaactgc acccactcct gtgtggacct | 2340 |
| ggatgacaag ggctgccccg ccgagcagag agccagccct ctgacgtcca tcatctctgc | 2400 |
| ggtggttggc attctgctgg tcgtggtctt gggggtggtc tttgggatcc tcatcaagcg | 2460 |
| acggcagcag aagatccgga agtacacgat gcggagactg ctgcaggaaa cggagctggt | 2520 |
| ggagccgctg acacctagcg gagcgatgcc caaccaggcg cagatgcgga tcctgaaaga | 2580 |

-continued

```
gacggagctg aggaaggtga aggtgcttgg atctggcgct tttggcacag tctacaaggg    2640
catctggatc cctgatgggg agaatgtgaa aattccagtg gccatcaaag tgttgaggga    2700
aaacacatcc cccaaagcca acaaagaaat cttagacgaa gcatacgtga tggctggtgt    2760
gggctcccca tatgtctccc gccttctggg catctgcctg acatccacgg tgcagctggt    2820
gacacagctt atgccctatg ctgcctctt agaccatgtc cgggaaaacc gcggacgcct     2880
gggctcccag gacctgctga actggtgtat gcagattgcc aaggggatga gctacctgga    2940
ggatgtgcgg ctcgtacaca gggacttggc cgctcggaac gtgctggtca agagtcccaa    3000
ccatgtcaaa attacagact cgggctggc tcggctgctg acattgacg agacagagta      3060
ccatgcagat gggggcaagg tgcccatcaa gtggatggcg ctggagtcca ttctccgccg    3120
gcggttcacc caccagagtg atgtgtgag ttatggtgtg actgtgtggg agctgatgac     3180
ttttggggcc aaaccttacg atgggatccc agcccgggag atccctgacc tgctggaaaa    3240
gggggagcgc ctgccccagc cccccatctg caccattgat gtctacatga tcatggtcaa    3300
atgttggatg attgactctg aatgtcggcc aagattccgg gagttggtgt ctgaattctc    3360
ccgcatggcc agggacccccc agcgctttgt ggtcatccag aatgaggact gggcccagc    3420
cagtcccttg gacagcacct tctaccgctc actgctggag gacgatgaca tggggggacct   3480
ggtggatgct gaggagtatc tggtaccccca gcagggcttc ttctgtccag accctgcccc   3540
gggcgctggg ggcatggtcc accacaggca ccgcagctca tctaccagga gtggcggtgg    3600
ggacctgaca ctagggctgg agccctctga gaggaggcc cccaggtctc cactggcacc     3660
ctccgaaggg gctggctccg atgtatttga tggtgacctg gaatgggggg cagccaaggg    3720
gctgcaaagc ctccccacac atgacccag ccctctacag cggtacagtg aggaccccac     3780
agtacccctg ccctctgaga ctgatggcta cgttgccccc ctgacctgca gccccagcc    3840
tgaatatgtg aaccagccag atgttcggcc ccagccccct tcgccccgag agggccctct    3900
gcctgctgcc cgacctgctg gtgccactct ggaaaggccc aagactctct ccccagggaa    3960
gaatggggtc gtcaaagacg ttttttgcctt tgggggtgcc gtggagaacc ccgagtactt    4020
gacacccag ggaggagctg cccctcagcc ccacctcct cctgccttca gcccagcctt      4080
cgacaacctc tattactggg accaggaccc accagagcgg ggggctccac ccagcacctt    4140
caaagggaca cctacggcag agaacccaga gtacctgggt ctggacgtgc cagtgtgaac    4200
cagaaggcca agtccgcaga agccctgatg tgtcctcagg gagcagggaa ggcctgactt    4260
ctgctggcat caagaggtgg gagggccctc cgaccactcc caggggaacc tgccatgcca    4320
ggaacctgtc ctaaggaacc ttccttcctg cttgagttcc cagatggctg aaggggtcc     4380
agcctcgttg gaagaggaac agcactgggg agtctttgtg gattctgagg ccctgcccaa    4440
tgagactcta gggtccagtg gatgccacag cccagcttgg ccctttcctt ccagatcctg    4500
ggtactgaaa gccttaggga agctggcctg agaggggaag cggccctaag ggagtgtcta    4560
agaacaaaag cgacccattc agagactgtc cctgaaacct agtactgccc cccatgagga    4620
aggaacagca atggtgtcag tatccaggct ttgtacagag tgcttttctg tttagttttt    4680
acttttttttg ttttgttttt ttaaagatga aataaagacc caggggggaga atgggtgttg   4740
tatgggggagg caagtgtggg gggtccttct ccacacccac tttgtccatt tgcaaatata    4800
ttttggaaaa cagcta                                                    4816
```

<210> SEQ ID NO 11
<211> LENGTH: 6456
<212> TYPE: DNA

<213> ORGANISM: Homo sapiens

<400> SEQUENCE: 11

```
gagttgtgcc tggagtgatg tttaagccaa tgtcagggca aggcaacagt ccctggccgt      60
cctccagcac ctttgtaatg catatgagct cgggagacca gtacttaaag ttggaggccc     120
gggagcccag gagctggcgg agggcgttcg tcctgggact gcacttgctc ccgtcgggtc     180
gcccggcttc accggacccg caggctcccg gggcagggcc ggggcagag ctcgcgtgtc     240
ggcgggacat gcgctgcgtc gcctctaacc tcgggctgtg ctcttttcc aggtggcccg     300
ccggtttctg agccttctgc cctgcgggga cacggtctgc accctgcccg cggccacgga     360
ccatgaccat gaccctccac accaaagcat ccgggatggc cctactgcat cagatccaag     420
ggaacgagct ggagcccctg aaccgtccgc agctcaagat cccctggag cggccctgg      480
gcgaggtgta cctggacagc agcaagcccg ccgtgtacaa ctaccccgag ggcgccgcct     540
acgagttcaa cgccgcggcc gccgccaacg cgcaggtcta cggtcagacc ggcctccct     600
acggccccgg gtctgaggct gcggcgttcg gctccaacgg cctgggggt tccccccac     660
tcaacagcgt gtcccgagc ccgctgatgc tactgcaccc gccgccgcag ctgtcgcctt     720
tcctgcagcc ccacggccag caggtgccct actacctgga gaacgagccc agcggctaca     780
cggtgcgcga ggccggcccg ccggcattct acaggccaaa ttcagataat cgacgccagg     840
gtggcagaga aagattggcc agtaccaatg acaagggaag tatggctatg aatctgcca    900
aggagactcg ctactgtgca gtgtgcaatg actatgcttc aggctaccat tatgagtct    960
ggtcctgtga gggctgcaag gccttcttca agagaagtat tcaaggacat aacgactata   1020
tgtgtccagc caccaaccag tgcaccattg ataaaaacag gaggaagagc tgccaggcct   1080
gccggctccg caaatgctac gaagtgggaa tgatgaaagg tgggatacga aaagaccgaa   1140
gaggagggag aatgttgaaa cacaagcgcc agagagatga tggggagggc agggtgaag    1200
tgggtctgc tggagacatg agagctgcca acctttggcc aagcccgctc atgatcaaac   1260
gctctaagaa gaacagcctg gccttgtccc tgacggccga ccagatggtc agtgccttgt   1320
tggatgctga gccccccata ctctattccg agtatgatcc taccagaccc ttcagtgaag   1380
cttcgatgat gggcttactg accaacctgg cagacaggga gctggttcac atgatcaact   1440
gggcgaagag ggtgccaggc tttgtggatt tgaccctcca tgatcaggtc caccttctag   1500
aatgtgcctg gctagagatc ctgatgattg gtctcgtctg gcgctccatg gagcacccag   1560
ggaagctact gtttgctcct aacttgctct tggacaggaa ccagggaaaa tgtgtagagg   1620
gcatggtgga gatcttcgac atgctgctgg ctacatcatc tcggttccgc atgatgaatc   1680
tgcagggaga ggagtttgtg tgcctcaaat ctattatttt gcttaattct ggagtgtaca   1740
catttctgtc cagcaccctg aagtctctgg aagagaagga ccatatccac cgagtcctgg   1800
acaagatcac agacactttg atccacctga tggccaaggc aggcctgacc ctgcagcagc   1860
agcaccagcg gctggcccag ctcctcctca tcctctccca catcaggcac atgagtaaca   1920
aaggcatgga gcatctgtac agcatgaagt gcaagaacgt ggtgcccctc tatgacctgc   1980
tgctggagat gctggacgcc caccgcctac atgcgcccac tagccgtgga ggggcatccg   2040
tggaggagac ggaccaaagc cacttggcca ctgcgggctc tacttcatcg cattccttgc   2100
aaaagtatta catcacgggg gaggcagagg gttttcctgc cacggtctga gagctccctg   2160
gctcccacac ggttcagata atccctgctg cattttaccc tcatcatgca ccactttagc   2220
caaattctgt ctcctgcata cactccggca tgcatccaac accaatggct ttctagatga   2280
```

```
gtggccattc atttgcttgc tcagttctta gtggcacatc ttctgtcttc tgttgggaac   2340
agccaaaggg attccaaggc taaatctttg taacagctct ctttcccct tgctatgtta    2400 ctaagcgtga ggattcccgt agctcttcac agctgaactc agtctatggg ttggggctca   2460
gataactctg tgcatttaag ctacttgtag agacccaggc ctggagagta dacattttgc   2520
ctctgataag cacttttttaa atggctctaa gaataagcca cagcaaagaa tttaaagtgg  2580
ctcctttaat tggtgacttg gagaaagcta ggtcaagggt ttattatagc accctcttgt   2640
attcctatgg caatgcatcc ttttatgaaa gtggtacacc ttaaagcttt tatatgactg   2700
tagcagagta tctggtgatt gtcaattcat tccccctata ggaatacaag gggcacacag   2760
ggaaggcaga tcccctagtt ggcaagacta ttttaacttg atacactgca gattcagatg   2820
tgctgaaagc tctgcctctg gctttccggt catgggttcc agttaattca tgcctcccat   2880
ggacctatgg agagcagcaa gttgatctta gttaagtctc cctatatgag ggataagttc   2940
ctgattttgt tttttatttt tgtgttacaa aagaaagccc tccctccctg aacttgcagt   3000
aaggtcagct tcaggacctg ttccagtggg cactgtactt ggatcttccc ggcgtgtgtg   3060
tgccttacac aggggtgaac tgttcactgt ggtgatgcat gatgagggta aatggtagtt   3120
gaaaggagca ggggccctgg tgttgcattt agccctgggg catggagctg aacagtactt   3180
gtgcaggatt gttgtggcta ctagagaaca agagggaaag tagggcagaa actggataca   3240
gttctgaggc acagccagac ttgctcaggg tggccctgcc acaggctgca gctacctagg   3300
aacattcctt gcagacccg cattgcccctt tgggggtgcc ctgggatccc tggggtagtc   3360
cagctcttct tcatttccca gcgtggccct ggttggaaga agcagctgtc acagctgctg   3420
tagacagctg tgttcctaca attggcccag caccctgggg cacggagaa gggtggggac   3480 cgttgctgtc actactcagg ctgactgggg cctggtcaga ttacgtatgc ccttggtggt   3540
ttagagataa tccaaaatca gggtttggtt tggggaagaa aatcctcccc cttcctcccc   3600
cgccccgttc cctaccgcct ccactcctgc cagctcattt ccttcaattt cctttgaacc   3660
tataggctaa aaaagaaagg ctcattccag ccacagggca gccttccctg ggcctttgct   3720
tctctagcac aattatgggt tacttccttt ttccttaacaa aaagaatgt ttgatttcct   3780 ctgggtgacc ttattgtctg taattgaaac cctattgaga ggtgatgtct gtgttagcca   3840
atgacccagg tgagctgctc gggcttctct tggtatgtct tgtttggaaa agtggatttc   3900
attcatttct gattgtccag ttaagtgatc accaaaggac tgagaatctg ggagggcaaa   3960
aaaaaaaaaa aagtttttat gtgcacttaa atttggggac aattttatgt atctgtgtta   4020
aggatatgtt taagaacata attctttttgt tgctgtttgt ttaagaagca ccttagtttg   4080
tttaagaagc accttatata gtataatata tattttttg aaattacatt gcttgtttat    4140
cagacaattg aatgtagtaa ttctgttctg gatttaattt gactgggtta acatgcaaaa   4200
accaaggaaa aatatttagt ttttttttt ttttttgtat acttttcaag ctaccttgtc    4260
atgtatacag tcatttatgc ctaaagcctg gtgattattc atttaaatga agatcacatt   4320
tcatatcaac ttttgtatcc acagtagaca aatagcact aatccagatg cctattgttg     4380
gatattgaat gacagacaat cttatgtagc aaagattatg cctgaaaagg aaaattattc   4440
agggcagcta attttgcttt taccaaaata tcagtagtaa tattttttgga cagtagctaa  4500 tgggtcagtg ggttcttttt aatgttata cttagatttt cttttaaaaa aattaaaata    4560
aaacaaaaaa aaatttctag gactagacga tgtaatacca gctaaagcca aacaattata   4620
cagtggaagg ttttacatta ttcatccaat gtgtttctat tcatgttaag atactactac   4680
```

-continued

```
atttgaagtg ggcagagaac atcagatgat tgaaatgttc gcccaggggt ctccagcaac    4740
tttggaaatc tctttgtatt tttacttgaa gtgccactaa tggacagcag atattttctg    4800
gctgatgttg gtattgggtg taggaacatg atttaaaaaa aaactcttgc ctctgctttc    4860
ccccactctg aggcaagtta aaatgtaaaa gatgtgattt atctgggggg ctcaggtatg    4920
gtggggaagt ggattcagga atctggggaa tggcaaatat attaagaaga gtattgaaag    4980
tatttggagg aaaatggtta attctgggtg tgcaccaggg ttcagtagag tccacttctg    5040
ccctggagac cacaaatcaa ctagctccat ttacagccat ttctaaaatg gcagcttcag    5100
ttctagagaa gaaagaacaa catcagcagt aaagtccatg gaatagctag tggtctgtgt    5160 ttctttttcgc cattgcctag cttgccgtaa tgattctata atgccatcat gcagcaatta    5220
tgagaggcta ggtcatccaa agagaagacc ctatcaatgt aggttgcaaa atctaacccc    5280
taaggaagtg cagtctttga tttgatttcc ctagtaacct tgcagatatg tttaaccaag    5340
ccatagccca tgccttttga gggctgaaca aataagggac ttactgataa tttacttttg    5400
atcacattaa ggtgttctca ccttgaaatc ttatacactg aaatggccat tgatttaggc    5460
cactggctta gagtactcct tccccctgcat gacactgatt acaaatactt tcctattcat    5520
actttccaat tatgagatgg actgtgggta ctggagtgaa tcactaacac catagtaatg    5580
tctaatattc acaggcagat ctgcttgggg aagctagtta tgtgaaaggc aaatagagtc    5640
atacagtagc tcaaaaggca accataattc tctttggtgc aggtcttggg agcgtgatct    5700
agattacact gcaccattcc caagttaatc ccctgaaaac ttactctcaa ctggagcaaa    5760
tgaactttgg tcccaaatat ccatcttttc agtagcgtta attatgctct gtttccaact    5820
gcatttcctt tccaattgaa ttaaagtgtg gcctcgtttt tagtcattta aaattgtttt    5880
ctaagtaatt gctgcctcta ttatggcact tcaattttgc actgtctttt gagattcaag    5940
aaaaatttct attctttttt ttgcatccaa ttgtgcctga acttttaaaa tatgtaaatg    6000
ctgccatgtt ccaaacccat cgtcagtgtg tgtgtttaga gctgtgcacc ctagaaacaa    6060
catattgtcc catgagcagg tgcctgagac acagacccct ttgcattcac agagaggtca    6120
ttggttatag agacttgaat taataagtga cattatgcca gtttctgttc tctcacaggt    6180
gataaacaat gcttttttgtg cactacatac tcttcagtgt agagctcttg ttttatggga    6240
aaaggctcaa atgccaaatt gtgtttgatg gattaatatg ccctttttgcc gatgcatact    6300 attactgatg tgactcggtt ttgtcgcagc tttgctttgt ttaatgaaac acacttgtaa    6360
acctcttttg cactttgaaa aagaatccag cgggatgctc gagcacctgt aaacaatttt    6420
ctcaacctat ttgatgttca aataaagaat taaact                              6456
```

<210> SEQ ID NO 12
<211> LENGTH: 4314
<212> TYPE: DNA
<213> ORGANISM: Homo sapiens

<400> SEQUENCE: 12

```
cgagatcccg gggagccagc ttgctgggag agcgggacgg tccggagcaa gcccagaggc      60
agaggaggcg acagagggaa aaagggccga gctagccgct ccagtgctgt acaggagccg     120
aagggacgca ccacgccagc cccagcccgg ctccagcgac agccaacgcc tcttgcagcg     180
cggcggcttc gaagccgccg cccggagctg ccctttcctc ttcggtgaag tttttaaaag     240
ctgctaaaga ctcggaggaa gcaaggaaag tgcctggtag gactgacggc tgcctttgtc     300
ctcctcctct ccacccccgcc tccccccacc ctgccttccc ccctccccc gtcttctctc     360
```

```
ccgcagctgc ctcagtcggc tactctcagc caacccccct caccacccttc ctccccaccc    420 gccccccgc ccccgtcggc ccagcgctgc cagcccgagt tgcagagag gtaactccct      480 ttggctgcga gcgggcgagc tagctgcaca ttgcaaagaa ggctcttagg agccaggcga    540
ctggggagcg gcttcagcac tgcagccacg acccgcctgg ttaggctgca cgcggagaga    600
accctctgtt ttcccccact ctctctccac ctcctcctgc cttccccacc ccgagtgcgg   660
agccagagat caaagatgaa aaggcagtc aggtcttcag tagccaaaaa acaaaacaaa    720
caaaaacaaa aaagccgaaa taaagaaaa agataataac tcagttctta tttgcaccta    780
cttcagtgga cactgaattt ggaaggtgga ggattttgtt ttttctttt aagatctggg    840 catcttttga atctacccct caagtattaa gagacagact gtgagcctag cagggcagat   900
cttgtccacc gtgtgtcttc ttctgcacga gactttgagg ctgtcagagc gcttttttgcg   960 tggttgctcc cgcaagtttc cttctctgga gcttcccgca ggtgggcagc tagctgcagc  1020
gactaccgca tcatcacagc ctgttgaact cttctgagca agagaagggg aggcggggta  1080
agggaagtag gtggaagatt cagccaagct caaggatgga agtgcagtta gggctgggaa  1140
gggtctaccc tcggccgccg tccaagacct accgaggagc tttccagaat ctgttccaga  1200
gcgtgcgcga agtgatccag aacccgggcc ccaggcaccc agaggccgcg agcgcagcac  1260
ctcccggcgc cagtttgctg ctgctgcagc agcagcagca gcagcagcag cagcagcagc  1320
agcagcagca gcagcagcag cagcagcagc agcaagagac tagccccagg cagcagcagc  1380
agcagcaggg tgaggatggt tctccccaag cccatcgtag aggccccaca ggctacctgg  1440
tcctggatga ggaacagcaa ccttcacagc cgcagtcggc cctggagtgc caccccgaga  1500
gaggttgcgt cccagagcct ggagccgccg tggccgccag caaggggctg ccgcagcagc  1560
tgccagcacc tccggacgag gatgactcag ctgccccatc cacgttgtcc ctgctgggcc  1620
ccactttccc cggcttaagc agctgctccg ctgaccttaa agacatcctg agcgaggcca  1680
gcaccatgca actccttcag caacagcagc aggaagcagt atccgaaggc agcagcagcg  1740
ggagagcgag ggaggcctcg ggggctccca cttcctccaa ggacaattac ttaggggggca  1800 cttcgaccat ttctgacaac gccaaggagt tgtgtaaggc agtgtcggtg tccatgggcc  1860
tgggtgtgga ggcgttggag catctgagtc aggggaaca gcttcggggg gattgcatgt  1920 acgcccact tttgggagtt ccacccgctg tgcgtcccac tccttgtgcc ccattggccg  1980
aatgcaaagg ttctctgcta gacgacagcg caggcaagag cactgaagat actgctgagt  2040 attcccctt caagggaggt tacaccaaag gctagaagg cgagagccta ggctgctctg  2100
gcagcgctgc agcagggagc tccgggacac ttgaactgcc gtctaccctg tctctctaca  2160
agtccggagc actggacgag gcagctgcgt accagagtcg cgactactac aactttccac  2220
tggctctggc cggaccgccg ccccctccgc cgcctcccca tccccacgct cgcatcaagc  2280
tggagaaccc gctggactac ggcagcgcct gggcggctgc ggcggcgcag tgccgctatg  2340
gggacctggc gagcctgcat ggcgcgggtg cagcgggacc cggttctggg tcaccctcag  2400
ccgccgcttc ctcatcctgg cacactctct tcacagccga agaaggccag ttgtatggac  2460
cgtgtggtgg tggtgggggt ggtggcggcg gcggcggcgg cggcggcggc ggcggcggcg  2520
gcggcggcgg cggcgaggcg ggagctgtag ccccctacgg ctacactcgg ccccctcagg  2580
ggctggcggg ccaggaaagc gacttcaccg cacctgatgt gtggtaccct ggcggcatgg  2640
tgagcagagt gccctatccc agtcccactt gtgtcaaaag cgaaatgggc ccctggatgg  2700
atagctactc cggaccttac ggggacatgc gtttggagac tgccagggac catgtttttgc  2760
```

```
ccattgacta ttactttcca ccccagaaga cctgcctgat ctgtggagat gaagcttctg   2820
ggtgtcacta tggagctctc acatgtggaa gctgcaggt cttcttcaaa agagccgctg    2880
aagggaaaca gaagtacctg tgcgccagca gaaatgattg cactattgat aaattccgaa   2940
ggaaaaattg tccatcttgt cgtcttcgga aatgttatga agcagggatg actctgggag   3000
cccggaagct gaagaaactt ggtaatctga actacagga ggaaggagag gcttccagca    3060
ccaccagccc cactgaggag acaacccaga agctgacagt gtcacacatt gaaggctatg   3120
aatgtcagcc catctttctg aatgtcctgg aagccattga gccaggtgta gtgtgtgctg   3180
gacacgacaa caaccagccc gactcctttg cagccttgct ctctagcctc aatgaactgg   3240
gagagagaca gcttgtacac gtggtcaagt gggccaaggc cttgcctggc ttccgcaact   3300
tacacgtgga cgaccagatg gctgtcattc agtactcctg gatggggctc atggtgtttg   3360
ccatgggctg gcgatccttc accaatgtca actccaggat gctctacttc gccctgatc    3420 tggttttcaa tgagtaccgc atgcacaagt cccggatgta cagccagtgt gtccgaatga   3480
ggcacctctc tcaagagttt ggatggctcc aaatcacccc ccaggaattc ctgtgcatga   3540
aagcactgct actcttcagc attattccag tggatgggct gaaaaatcaa aaattctttg   3600
atgaacttcg aatgaactac atcaaggaac tcgatcgtat cattgcatgc aaaagaaaaa   3660
atcccacatc ctgctcaaga cgcttctacc agctcaccaa gctcctggac tccgtgcagc   3720
ctattgcgag agagctgcat cagttcactt ttgacctgct aatcaagtca cacatggtga   3780
gcgtggactt tccggaaatg atggcagaga tcatctctgt gcaagtgccc aagatccttt   3840
ctgggaaagt caagcccatc tatttccaca cccagtgaag cattggaaac cctatttccc   3900
caccccagct catgccccct ttcagatgtc ttctgcctgt tataactctg cactactcct   3960
ctgcagtgcc ttggggaatt tcctctattg atgtacagtc tgtcatgaac atgttcctga   4020
attctatttg ctgggctttt ttttctctt tctctcctt cttttcttc ttccctccct      4080 atctaaccct cccatggcac cttcagactt tgcttcccat tgtggctcct atctgtgttt   4140
tgaatggtgt tgtatgcctt taaatctgtg atgatcctca tatggcccag tgtcaagttg   4200
tgcttgttta cagcactact ctgtgccagc cacacaaacg tttacttatc ttatgccacg   4260
ggaagtttag agagctaaga ttatctgggg aaatcaaaac aaaaacaagc aaac         4314
```

<210> SEQ ID NO 13
<211> LENGTH: 2554
<212> TYPE: DNA
<213> ORGANISM: Homo sapiens

<400> SEQUENCE: 13

```
acaaggcagc ctcgctcgag cgcaggccaa tcggctttct agctagaggg tttaactcct     60
atttaaaaag aagaaccttt gaattctaac ggctgagctc ttggaagact gggtccttg    120 ggtcgcaggt gggagccgac gggtgggtag accgtggggg atatctcagt ggcggacgag   180
gacggcgggg acaaggggcg gctggtcgga gtggcggagc gtcaagtccc ctgtcggttc   240
ctccgtccct gagtgtcctt ggcgctgcct tgtgcccgcc cagcgccttt gcatccgctc   300
ctgggcaccg aggcgccctg taggatactg cttgttactt attacagcta gagggtctca   360
ctccattgcc caggccagag tgcggggata tttgataaga aacttcagtg aaggccgggc   420
gcggtggctc atgcccgtaa tcccagcatt tcggaggcc gaggctggag tgcaatggtg     480
tgatctcagc tcactgcaac ctctgcttcc tgggtttaag tgattctcct gcctcagcct   540
cccgagtagc tgggattaca ggcatcatgg accgatctaa agaaaactgc atttcaggac   600
```

-continued

| | |
|---|---|
| ctgttaaggc tacagctcca gttggaggtc caaaacgtgt tctcgtgact cagcaatttc | 660 |
| cttgtcagaa tccattacct gtaaatagtg gccaggctca gcgggtcttg tgtccttcaa | 720 |
| attcttccca gcgcattcct ttgcaagcac aaaagcttgt ctccagtcac aagccggttc | 780 |
| agaatcagaa gcagaagcaa ttgcaggcaa ccagtgtacc tcatcctgtc tccaggccac | 840 |
| tgaataacac ccaaaagagc aagcagcccc tgccatcggc acctgaaaat aatcctgagg | 900 |
| aggaactggc atcaaaacag aaaaatgaag aatcaaaaaa gaggcagtgg gctttggaag | 960 |
| actttgaaat tggtcgccct ctgggtaaag gaaagtttgg taatgtttat ttggcaagag | 1020 |
| aaaagcaaag caagtttatt ctggctctta agtgttatt taaagctcag ctggagaaag | 1080 |
| ccggagtgga gcatcagctc agaagagaag tagaaataca gtcccacctt cggcatccta | 1140 |
| atattcttag actgtatggt tatttccatg atgctaccag agtctaccta attctggaat | 1200 |
| atgcaccact tggaacagtt tatagagaac ttcagaaact ttcaaagttt gatgagcaga | 1260 |
| gaactgctac ttatataaca gaattggcaa atgccctgtc ttactgtcat tcgaagagag | 1320 |
| ttattcatag agacattaag ccagagaact tacttcttgg atcagctgga gagcttaaaa | 1380 |
| ttgcagattt tgggtggtca gtacatgctc catcttccag gaggaccact ctctgtggca | 1440 |
| ccctggacta cctgcccccct gaaatgattg aaggtcggat gcatgatgag aaggtggatc | 1500 |
| tctggagcct tggagttctt tgctatgaat ttttagttgg gaagcctcct tttgaggcaa | 1560 |
| acacatacca agagacctac aaaagaatat cacgggttga attcacattc cctgactttg | 1620 |
| taacagaggg agccagggac ctcatttcaa gactgttgaa gcataatccc agccagaggc | 1680 |
| caatgctcag agaagtactt gaacacccct ggatcacagc aaattcatca aaaccatcaa | 1740 |
| attgccaaaa caaagaatca gctagcaaac agtcttagga atcgtgcagg gggagaaatc | 1800 |
| cttgagccag ggctgccata taacctgaca ggaacatgct actgaagttt attttaccat | 1860 |
| tgactgctgc cctcaatcta aacgctaca caagaaatat ttgttttact cagcaggtgt | 1920 |
| gccttaacct ccctattcag aaagctccac atcaataaac atgacactct gaagtgaaag | 1980 |
| tagccacgag aattgtgcta cttatactgg ttcataatct ggaggcaagg ttcgactgca | 2040 |
| gccgccccgt cagcctgtgc taggcatggt gtcttcacag gaggcaaatc cagagcctgg | 2100 |
| ctgtggggaa agtgaccact ctgccctgac cccgatcagt taaggagctg tgcaataacc | 2160 |
| ttcctagtac ctgagtgagt gtgtaactta ttgggttggc gaagcctggt aaagctgttg | 2220 |
| gaatgagtat gtgattcttt ttaagtatga aaataaagat atatgtacag acttgtatt | 2280 |
| tttctctggt ggcattcctt taggaatgct gtgtgtctgt ccggcacccc ggtaggcctg | 2340 |
| attgggtttc tagtcctcct taaccactta tctcccatat gagagtgtga aaaataggaa | 2400 |
| cacgtgctct acctccatt agggattgc ttgggataca gaagaggcca tgtgtctcag | 2460 |
| agctgttaag ggcttatttt tttaaaacat tggagtcata gcatgtgtgt aaactttaaa | 2520 |
| tatgcaaata aataagtatc tatgtctaaa aaaa | 2554 |

<210> SEQ ID NO 14
<211> LENGTH: 1616
<212> TYPE: DNA
<213> ORGANISM: Homo sapiens

<400> SEQUENCE: 14

| | |
|---|---|
| ctccctgtgt tggtggagga tgtctgcagc agcatttaaa ttctgggagg gcttggttgt | 60 |
| cagcagcagc aggaggaggc agagcacagc atcgtcggga ccagactcgt ctcaggccag | 120 |
| ttgcagcctt ctcagccaaa cgccgaccaa ggaaaactca ctaccatgag aattgcagtg | 180 |

-continued

```
atttgctttt gcctcctagg catcacctgt gccataccag ttaaacaggc tgattctgga       240
agttctgagg aaaagcagct ttacaacaaa tacccagatg ctgtggccac atggctaaac       300
cctgacccat ctcagaagca gaatctccta gccccacaga cccttccaag taagtccaac       360
gaaagccatg accacatgga tgatatggat gatgaagatg atgatgacca tgtggacagc       420
caggactcca ttgactcgaa cgactctgat gatgtagatg acactgatga ttctcaccag       480
tctgatgagt ctcaccattc tgatgaatct gatgaactgg tcactgattt tcccacggac       540
ctgccagcaa ccgaagtttt cactccagtt gtccccacag tagacacata tgatggccga       600
ggtgatagtg tggtttatgg actgaggtca aaatctaaga agtttcgcag acctgacatc       660
cagtaccctg atgctacaga cgaggacatc acctcacaca tggaaagcga ggagttgaat       720
ggtgcataca aggccatccc cgttgcccag gacctgaacg cgccttctga ttgggacagc       780
cgtgggaagg acagttatga aacgagtcag ctggatgacc agagtgctga aacccacagc       840
cacaagcagt ccagattata taagcggaaa gccaatgatg agagcaatga gcattccgat       900
gtgattgata gtcaggaact ttccaaagtc agccgtgaat tccacagcca tgaatttcac       960
agccatgaag atatgctggt tgtagacccc aaaagtaagg aagaagataa acacctgaaa      1020
tttcgtattt ctcatgaatt agatagtgca tcttctgagg tcaattaaaa ggagaaaaaa      1080
tacaatttct cactttgcat ttagtcaaaa gaaaaaatgc tttatagcaa aatgaaagag      1140
aacatgaaat gcttctttct cagtttattg gttgaatgtg tatctatttg agtctggaaa      1200
taactaatgt gtttgataat tagtttagtt tgtggcttca tggaaactcc ctgtaaacta      1260
aaagcttcag ggttatgtct atgttcattc tatagaagaa atgcaaacta tcactgtatt      1320
ttaatatttg ttattctctc atgaataaaa atttatgtag aagcaaacaa aatactttta      1380
cccacttaaa aagagaatat aacatttat gtcactataa tcttttgttt tttaagttag       1440
tgtatatttt gttgtgatta tcttttgtg gtgtgaataa atcttttatc ttgaatgtaa       1500
taagaatttg gtggtgtcaa ttgcttattt gttttcccac ggttgtccag caattaataa       1560
aacataacct tttttactgc ctaaaaaaaa aaaaaaaaa aaaaaaaaa aaaaaa           1616
```

<210> SEQ ID NO 15
<211> LENGTH: 2276
<212> TYPE: DNA
<213> ORGANISM: Homo sapiens

<400> SEQUENCE: 15

```
aagcccagca gccccggggc ggatggctcc ggccgcctgg ctccgcagcg cggccgcgcg        60
cgccctcctg cccccgatgc tgctgctgct gctccagccg ccgccgctgc tggcccgggc       120
tctgccgccg gacgcccacc acctccatgc cgagaggagg gggccacagc cctggcatgc       180
agccctgccc agtagcccgg cacctgcccc tgccacgcag gaagcccccc ggcctgccag       240
cagcctcagg cctccccgct gtggcgtgcc cgacccatct gatgggctga gtgcccgcaa       300
ccgacagaag aggttcgtgc tttctggcgg gcgctgggag aagacggacc tcacctacag       360
gatccttcgg ttcccatggc agttggtgca ggagcaggtg cggcagacga tggcagaggc       420
cctaaaggta tggagcgatg tgacgccact cacctttact gaggtgcacg agggccgtgc       480
tgacatcatg atcgacttcg ccaggtactg catggggac gacctgccgt ttgatgggcc       540
tgggggcatc ctggcccatg ccttcttccc caagactcac cgagaagggg atgtccactt       600
cgactatgat gagacctgga ctatcgggga tgaccagggc acagacctgc tgcaggtggc       660
agcccatgaa tttggccacg tgctggggct gcagcacaca acagcagcca aggccctgat       720
```

| | |
|---|---|
| gtccgccttc tacacctttc gctacccact gagtctcagc ccagatgact gcaggggcgt | 780 |
| tcaacaccta tatggccagc cctggccac tgtcacctcc aggacccag ccctgggccc | 840 |
| ccaggctggg atagacacca atgagattgc accgctggag ccagacgccc cgccagatgc | 900 |
| ctgtgaggcc tcctttgacg cggtctccac catccgaggc gagctctttt tcttcaaagc | 960 |
| gggctttgtg tggcgcctcc gtgggggcca gctgcagccc ggctaccag cattggcctc | 1020 |
| tcgccactgg cagggactgc ccagcccctgt ggacgctgcc ttcgaggatg cccagggcca | 1080 |
| catttggttc ttccaaggtg ctcagtactg ggtgtacgac ggtgaaaagc cagtcctggg | 1140 |
| ccccgcaccc ctcaccgagc tgggcctggt gaggttcccg gtccatgctg ccttggtctg | 1200 |
| gggtcccgag aagaacaaga tctacttctt ccgaggcagg gactactggc gtttccaccc | 1260 |
| cagcacccgg cgtgtagaca gtcccgtgcc ccgcagggcc actgactgga gaggggtgcc | 1320 |
| ctctgagatc gacgctgcct tccaggatgc tgatggctat gcctacttcc tgcgcggccg | 1380 |
| cctctactgg aagtttgacc ctgtgaaggt gaaggctctg gaaggcttcc cccgtctcgt | 1440 |
| gggtcctgac ttctttggct gtgccgagcc tgccaacact ttcctctgac catggcttgg | 1500 |
| atgccctcag gggtgctgac ccctgccagg ccacgaatat caggctagag acccatggcc | 1560 |
| atctttgtgg ctgtgggcac caggcatggg actgagccca tgtctcctca gggggatggg | 1620 |
| gtggggtaca accaccatga caactgccgg gagggcacg caggtcgtgg tcacctgcca | 1680 |
| gcgactgtct cagactgggc agggaggctt tggcatgact aagaggaag ggcagtcttg | 1740 |
| ggcccgctat gcaggtcctg gcaaacctgg ctgccctgtc ccatccctg tcctcaggg | 1800 |
| tagcaccatg gcaggactgg gggaactgga gtgtccttgc tgtatccctg ttgtgaggtt | 1860 |
| ccttccaggg gctggcactg aagcaagggt gctggggccc catggccttc agccctggct | 1920 |
| gagcaactgg gctgtagggc agggccactt cctgaggtca ggtcttggta ggtgcctgca | 1980 |
| tctgtctgcc ttctggctga caatcctgga aatctgttct ccagaatcca ggccaaaaag | 2040 |
| ttcacagtca aatggggagg ggtattcttc atgcaggaga ccccaggccc tggaggctgc | 2100 |
| aacatacctc aatcctgtcc caggccggat cctcctgaag ccctttcgc agcactgcta | 2160 |
| tcctccaaag ccattgtaaa tgtgtgtaca gtgtgtataa accttcttct tctttttttt | 2220 |
| tttttaaact gaggattgtc attaaacaca gttgttttct aaaaaaaaaa aaaaaa | 2276 |

```
<210> SEQ ID NO 16
<211> LENGTH: 3035
<212> TYPE: DNA
<213> ORGANISM: Homo sapiens

<400> SEQUENCE: 16
```

| | |
|---|---|
| agagccagag caggatggag aggagacgca tcacctccgc tgctcgccgc tcctacgtct | 60 |
| cctcagggga gatgatggtg gggggcctgg ctcctggccg ccgtctgggt cctggcaccc | 120 |
| gcctctccct ggctcgaatg cccccctccac tcccgacccg ggtggatttc tccctggctg | 180 |
| ggcactcaa tgctggcttc aaggagaccc gggccagtga gcgggcagag atgatggagc | 240 |
| tcaatgaccg ctttgccagc tacatcgaga aggttcgctt cctggaacag caaaacaagg | 300 |
| cgctggctgc tgagctgaac cagctgcggg ccaaggagcc caccaagctg gcagacgtct | 360 |
| accaggctga gctgcgagag ctgcggctgc ggctcgatca actcaccgcc aacagcgccc | 420 |
| ggctggaggt tgagagggac aatctggcac aggacctggc cactgtgagg cagaagctcc | 480 |
| aggatgaaac caacctgagg ctggaagccg agaacaacct ggctgcctat agacaggaag | 540 |
| cagatgaagc caccctggcc cgtctggatc tggagaggaa gattgagtcg ctggaggagg | 600 |

| | |
|---|---|
| agatccggtt cttgaggaag atccacgagg aggaggttcg ggaactccag gagcagctgg | 660 |
| cccgacagca ggtccatgtg gagcttgacg tggccaagcc agacctcacc gcagccctga | 720 |
| aagagatccg cacgcagtat gaggcaatgg cgtccagcaa catgcatgaa gccgaagagt | 780 |
| ggtaccgctc caagtttgca gacctgacag acgctgctgc ccgcaacgcg gagctgctcc | 840 |
| gccaggccaa gcacgaagcc aacgactacc ggcgccagtt gcagtccttg acctgcgacc | 900 |
| tggagtctct gcgcggcacg aacgagtccc tggagaggca gatgcgcgag caggaggagc | 960 |
| ggcacgtgcg ggaggcggcc agttatcagg aggcgctggc gcggctggag aagaggggc | 1020 |
| agagcctcaa ggacgagatg gcccgccact tgcaggagta ccaggacctg ctcaatgtca | 1080 |
| agctggccct ggacatcgag atcgccacct acaggaagct gctagagggc gaggagaacc | 1140 |
| ggatcaccat tcccgtgcag accttctcca acctgcagat tcgagaaacc agcctggaca | 1200 |
| ccaagtctgt gtcagaaggc cacctcaaga ggaacatcgt ggtgaagacc gtggagatgc | 1260 |
| gggatggaga ggtcattaag gagtccaagc aggagcacaa ggatgtgatg tgaggcagga | 1320 |
| cccacctggt ggcctctgcc ccgtctcatg aggggcccga gcagaagcag gatagttgct | 1380 |
| ccgcctctgc tggcacattt ccccagacct gagctcccca ccaccccagc tgctcccctc | 1440 |
| cctcctctgt ccctaggtca gcttgctgcc ctaggctccg tcagtatcag gcctgccaga | 1500 |
| cggcacccac ccagcaccca gcaactccaa ctaacaagaa actcaccccc aaggggcagt | 1560 |
| ctggaggggc atggccagca gcttgcgtta gaatgaggag gaaggagaga aggggaggag | 1620 |
| ggcgggggc acctactaca tcgccctcca catccctgat tcctgttgtt atggaaactg | 1680 |
| ttgccagaga tggaggttct ctcggagtat ctgggaactg tgccttgag tttcctcagg | 1740 |
| ctgctggagg aaaactgaga ctcagacagg aaagggaagg ccccacagac aaggtagccc | 1800 |
| tggccagagg cttgttttgt cttttggttt ttatgaggtg ggatatccct atgctgccta | 1860 |
| ggctgacctt gaactcctgg gctcaagcag tctacccacc tcagcctcct gtgtagctgg | 1920 |
| gattatagat tggagccacc atgcccagct cagagggttg ttctcctaga ctgaccctga | 1980 |
| tcagtctaag atgggtgggg acgtcctgcc acctggggca gtcacctgcc cagatcccag | 2040 |
| aaggacctcc tgagcgatga ctcaagtgtc tcagtccacc tgagctgcca tccagggatg | 2100 |
| ccatctgtgg gcacgctgtg ggcaggtggg agcttgattc tcagcacttg ggggatctgt | 2160 |
| tgtgtacgtg gagagggatg aggtgctggg agggatagag gggggctgcc tggccccag | 2220 |
| ctgtgggtac agagaggtca agcccaggag gactgccccg tgcagactgg aggggacgct | 2280 |
| ggtagagatg gaggaggagg caattgggat ggcgctaggc atacaagtag gggttgtggg | 2340 |
| tgaccagttg cacttggcct ctggattgtg ggaattaagg aagtgactca tcctcttgaa | 2400 |
| gatgctgaaa caggagagaa aggggatgta tccatggggg cagggcatga ctttgtccca | 2460 |
| tttctaaagg cctcttcctt gctgtgtcat accaggccgc cccagcctct gagcccctgg | 2520 |
| gactgctgct tcttaacccc agtaagccac tgccacacgt ctgaccctct ccaccccata | 2580 |
| gtgaccggct gcttttccct aagccaaggg cctcttgcgg tcccttctta ctcacacaca | 2640 |
| aaatgtaccc agtattctag gtagtgccct attttacaat tgtaaaactg aggcacgagc | 2700 |
| aaagtgaaga cactggctca tattcctgca gcctggaggc cgggtgctca gggctgacac | 2760 |
| gtccacccca gtgcacccac tctgctttga ctgagcagac tggtgagcag actggtggga | 2820 |
| tctgtgccca gagatgggac tgggagggcc cacttcaggg ttctcctctc ccctctaagg | 2880 |
| ccgaagaagg gtccttccct ctccccaaga cttggtgtcc tttccctcca cttcctcctg | 2940 |
| ccacctgctg ctgctgctgc tgctaatctt cagggcactg ctgctgcctt tagtcgctga | 3000 | ggaaaaataa agacaaatgc tgcgcccttc cccag 3035

<210> SEQ ID NO 17
<211> LENGTH: 525
<212> TYPE: PRT
<213> ORGANISM: Homo sapiens

<400> SEQUENCE: 17

```
Met Arg Arg Arg Arg Arg Asp Gly Phe Tyr Pro Ala Pro Asp Phe
1               5                   10                  15

Arg Asp Arg Glu Ala Glu Asp Met Ala Gly Val Phe Asp Ile Asp Leu
            20                  25                  30

Asp Gln Pro Glu Asp Ala Gly Ser Glu Asp Glu Leu Glu Glu Gly Gly
        35                  40                  45

Gln Leu Asn Glu Ser Met Asp His Gly Val Gly Pro Tyr Glu Leu
    50                  55                  60

Gly Met Glu His Cys Glu Lys Phe Glu Ile Ser Glu Thr Ser Val Asn
65                  70                  75                  80

Arg Gly Pro Glu Lys Ile Arg Pro Glu Cys Phe Glu Leu Leu Arg Val
                85                  90                  95

Leu Gly Lys Gly Gly Tyr Gly Lys Val Phe Gln Val Arg Lys Val Thr
            100                 105                 110

Gly Ala Asn Thr Gly Lys Ile Phe Ala Met Lys Val Leu Lys Lys Ala
        115                 120                 125

Met Ile Val Arg Asn Ala Lys Asp Thr Ala His Thr Lys Ala Glu Arg
130                 135                 140

Asn Ile Leu Glu Glu Val Lys His Pro Phe Ile Val Asp Leu Ile Tyr
145                 150                 155                 160

Ala Phe Gln Thr Gly Gly Lys Leu Tyr Leu Ile Leu Glu Tyr Leu Ser
                165                 170                 175

Gly Gly Glu Leu Phe Met Gln Leu Glu Arg Glu Gly Ile Phe Met Glu
            180                 185                 190

Asp Thr Ala Cys Phe Tyr Leu Ala Glu Ile Ser Met Ala Leu Gly His
        195                 200                 205

Leu His Gln Lys Gly Ile Ile Tyr Arg Asp Leu Lys Pro Glu Asn Ile
    210                 215                 220

Met Leu Asn His Gln Gly His Val Lys Leu Thr Asp Phe Gly Leu Cys
225                 230                 235                 240

Lys Glu Ser Ile His Asp Gly Thr Val Thr His Thr Phe Cys Gly Thr
                245                 250                 255

Ile Glu Tyr Met Ala Pro Glu Ile Leu Met Arg Ser Gly His Asn Arg
            260                 265                 270

Ala Val Asp Trp Trp Ser Leu Gly Ala Leu Met Tyr Asp Met Leu Thr
        275                 280                 285

Gly Ala Pro Pro Phe Thr Gly Glu Asn Arg Lys Lys Thr Ile Asp Lys
    290                 295                 300

Ile Leu Lys Cys Lys Leu Asn Leu Pro Pro Tyr Leu Thr Gln Glu Ala
305                 310                 315                 320

Arg Asp Leu Leu Lys Lys Leu Leu Lys Arg Asn Ala Ala Ser Arg Leu
                325                 330                 335

Gly Ala Gly Pro Gly Asp Ala Gly Glu Val Gln Ala His Pro Phe Phe
            340                 345                 350

Arg His Ile Asn Trp Glu Glu Leu Leu Ala Arg Lys Val Glu Pro Pro
        355                 360                 365

Phe Lys Pro Leu Leu Gln Ser Glu Glu Asp Val Ser Gln Phe Asp Ser
```

```
              370                 375                 380
Lys Phe Thr Arg Gln Thr Pro Val Asp Ser Pro Asp Ser Thr Leu
385                 390                 395                 400

Ser Glu Ser Ala Asn Gln Val Phe Leu Gly Phe Thr Tyr Val Ala Pro
                405                 410                 415

Ser Val Leu Glu Ser Val Lys Glu Lys Phe Ser Phe Glu Pro Lys Ile
                420                 425                 430

Arg Ser Pro Arg Arg Phe Ile Gly Ser Pro Arg Thr Pro Val Ser Pro
                435                 440                 445

Val Lys Phe Ser Pro Gly Asp Phe Trp Gly Arg Gly Ala Ser Ala Ser
450                 455                 460

Thr Ala Asn Pro Gln Thr Pro Val Glu Tyr Pro Met Glu Thr Ser Gly
465                 470                 475                 480

Ile Glu Gln Met Asp Val Thr Met Ser Gly Glu Ala Ser Ala Pro Leu
                485                 490                 495

Pro Ile Arg Gln Pro Asn Ser Gly Pro Tyr Lys Lys Gln Ala Phe Pro
                500                 505                 510

Met Ile Ser Lys Arg Pro Glu His Leu Arg Met Asn Leu
                515                 520                 525

<210> SEQ ID NO 18
<211> LENGTH: 249
<212> TYPE: PRT
<213> ORGANISM: Homo sapiens

<400> SEQUENCE: 18

Met Lys Leu Asn Ile Ser Phe Pro Ala Thr Gly Cys Gln Lys Leu Ile
1               5                   10                  15

Glu Val Asp Asp Glu Arg Lys Leu Arg Thr Phe Tyr Glu Lys Arg Met
                20                  25                  30

Ala Thr Glu Val Ala Ala Asp Ala Leu Gly Glu Glu Trp Lys Gly Tyr
            35                  40                  45

Val Val Arg Ile Ser Gly Gly Asn Asp Lys Gln Gly Phe Pro Met Lys
        50                  55                  60

Gln Gly Val Leu Thr His Gly Arg Val Arg Leu Leu Leu Ser Lys Gly
65                  70                  75                  80

His Ser Cys Tyr Arg Pro Arg Arg Thr Gly Glu Arg Lys Arg Lys Ser
                85                  90                  95

Val Arg Gly Cys Ile Val Asp Ala Asn Leu Ser Val Leu Asn Leu Val
                100                 105                 110

Ile Val Lys Lys Gly Glu Lys Asp Ile Pro Gly Leu Thr Asp Thr Thr
            115                 120                 125

Val Pro Arg Arg Leu Gly Pro Lys Arg Ala Ser Arg Ile Arg Lys Leu
        130                 135                 140

Phe Asn Leu Ser Lys Glu Asp Asp Val Arg Gln Tyr Val Val Arg Lys
145                 150                 155                 160

Pro Leu Asn Lys Glu Gly Lys Lys Pro Arg Thr Lys Ala Pro Lys Ile
                165                 170                 175

Gln Arg Leu Val Thr Pro Arg Val Leu Gln His Lys Arg Arg Arg Ile
                180                 185                 190

Ala Leu Lys Lys Gln Arg Thr Lys Lys Asn Lys Glu Glu Ala Ala Glu
            195                 200                 205

Tyr Ala Lys Leu Leu Ala Lys Arg Met Lys Glu Ala Lys Glu Lys Arg
        210                 215                 220

Gln Glu Gln Ile Ala Lys Arg Arg Arg Leu Ser Ser Leu Arg Ala Ser
```

```
                225                 230                 235                 240
        Thr Ser Lys Ser Glu Ser Ser Gln Lys
                        245

<210> SEQ ID NO 19
<211> LENGTH: 480
<212> TYPE: PRT
<213> ORGANISM: Homo sapiens

<400> SEQUENCE: 19

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
```

```
                355             360             365
Pro Arg Thr Leu Gly Pro Glu Ala Lys Ser Leu Leu Ser Gly Leu Leu
370             375             380

Lys Lys Asp Pro Lys Gln Arg Leu Gly Gly Ser Glu Asp Ala Lys
385             390             395             400

Glu Ile Met Gln His Arg Phe Phe Ala Gly Ile Val Trp Gln His Val
    405             410             415

Tyr Glu Lys Lys Leu Ser Pro Pro Phe Lys Pro Gln Val Thr Ser Glu
        420             425             430

Thr Asp Thr Arg Tyr Phe Asp Glu Glu Phe Thr Ala Gln Met Ile Thr
        435             440             445

Ile Thr Pro Pro Asp Gln Asp Asp Ser Met Glu Cys Val Asp Ser Glu
    450             455             460

Arg Arg Pro His Phe Pro Gln Phe Ser Tyr Ser Ala Ser Gly Thr Ala
465             470             475             480

<210> SEQ ID NO 20
<211> LENGTH: 2549
<212> TYPE: PRT
<213> ORGANISM: Homo sapiens

<400> SEQUENCE: 20

Met Leu Gly Thr Gly Pro Ala Ala Ala Thr Thr Ala Ala Thr Thr Ser
1               5               10              15

Ser Asn Val Ser Val Leu Gln Gln Phe Ala Ser Gly Leu Lys Ser Arg
            20              25              30

Asn Glu Glu Thr Arg Ala Lys Ala Ala Lys Glu Leu Gln His Tyr Val
        35              40              45

Thr Met Glu Leu Arg Glu Met Ser Gln Glu Glu Ser Thr Arg Phe Tyr
    50              55              60

Asp Gln Leu Asn His His Ile Phe Glu Leu Val Ser Ser Ser Asp Ala
65              70              75              80

Asn Glu Arg Lys Gly Gly Ile Leu Ala Ile Ala Ser Leu Ile Gly Val
            85              90              95

Glu Gly Gly Asn Ala Thr Arg Ile Gly Arg Phe Ala Asn Tyr Leu Arg
        100             105             110

Asn Leu Leu Pro Ser Asn Asp Pro Val Val Met Glu Met Ala Ser Lys
    115             120             125

Ala Ile Gly Arg Leu Ala Met Ala Gly Asp Thr Phe Thr Ala Glu Tyr
130             135             140

Val Glu Phe Glu Val Lys Arg Ala Leu Glu Trp Leu Gly Ala Asp Arg
145             150             155             160

Asn Glu Gly Arg Arg His Ala Ala Val Leu Val Leu Arg Glu Leu Ala
            165             170             175

Ile Ser Val Pro Thr Phe Phe Phe Gln Gln Val Gln Pro Phe Phe Asp
        180             185             190

Asn Ile Phe Val Ala Val Trp Asp Pro Lys Gln Ala Ile Arg Glu Gly
    195             200             205

Ala Val Ala Ala Leu Arg Ala Cys Leu Ile Leu Thr Thr Gln Arg Glu
210             215             220

Pro Lys Glu Met Gln Lys Pro Gln Trp Tyr Arg His Thr Phe Glu Glu
225             230             235             240

Ala Glu Lys Gly Phe Asp Glu Thr Leu Ala Lys Glu Lys Gly Met Asn
            245             250             255

Arg Asp Asp Arg Ile His Gly Ala Leu Leu Ile Leu Asn Glu Leu Val
```

-continued

```
                    260                 265                 270
Arg Ile Ser Ser Met Glu Gly Glu Arg Leu Arg Glu Glu Met Glu Glu
            275                 280                 285
Ile Thr Gln Gln Gln Leu Val His Asp Lys Tyr Cys Lys Asp Leu Met
        290                 295                 300
Gly Phe Gly Thr Lys Pro Arg His Ile Thr Pro Phe Thr Ser Phe Gln
305                 310                 315                 320
Ala Val Gln Pro Gln Gln Ser Asn Ala Leu Val Gly Leu Leu Gly Tyr
                325                 330                 335
Ser Ser His Gln Gly Leu Met Gly Phe Gly Thr Ser Pro Ser Pro Ala
            340                 345                 350
Lys Ser Thr Leu Val Glu Ser Arg Cys Cys Arg Asp Leu Met Glu Glu
        355                 360                 365
Lys Phe Asp Gln Val Cys Gln Trp Val Leu Lys Cys Arg Asn Ser Lys
    370                 375                 380
Asn Ser Leu Ile Gln Met Thr Ile Leu Asn Leu Leu Pro Arg Leu Ala
385                 390                 395                 400
Ala Phe Arg Pro Ser Ala Phe Thr Asp Thr Gln Tyr Leu Gln Asp Thr
                405                 410                 415
Met Asn His Val Leu Ser Cys Val Lys Lys Glu Lys Glu Arg Thr Ala
            420                 425                 430
Ala Phe Gln Ala Leu Gly Leu Leu Ser Val Ala Val Arg Ser Glu Phe
        435                 440                 445
Lys Val Tyr Leu Pro Arg Val Leu Asp Ile Ile Arg Ala Ala Leu Pro
    450                 455                 460
Pro Lys Asp Phe Ala His Lys Arg Gln Lys Ala Met Gln Val Asp Ala
465                 470                 475                 480
Thr Val Phe Thr Cys Ile Ser Met Leu Ala Arg Ala Met Gly Pro Gly
                485                 490                 495
Ile Gln Gln Asp Ile Lys Glu Leu Leu Glu Pro Met Leu Ala Val Gly
            500                 505                 510
Leu Ser Pro Ala Leu Thr Ala Val Leu Tyr Asp Leu Ser Arg Gln Ile
        515                 520                 525
Pro Gln Leu Lys Lys Asp Ile Gln Asp Gly Leu Leu Lys Met Leu Ser
    530                 535                 540
Leu Val Leu Met His Lys Pro Leu Arg His Pro Gly Met Pro Lys Gly
545                 550                 555                 560
Leu Ala His Gln Leu Ala Ser Pro Gly Leu Thr Thr Leu Pro Glu Ala
                565                 570                 575
Ser Asp Val Gly Ser Ile Thr Leu Ala Leu Arg Thr Leu Gly Ser Phe
            580                 585                 590
Glu Phe Glu Gly His Ser Leu Thr Gln Phe Val Arg His Cys Ala Asp
        595                 600                 605
His Phe Leu Asn Ser Glu His Lys Glu Ile Arg Met Glu Ala Ala Arg
    610                 615                 620
Thr Cys Ser Arg Leu Leu Thr Pro Ser Ile His Leu Ile Ser Gly His
625                 630                 635                 640
Ala His Val Val Ser Gln Thr Ala Val Gln Val Val Ala Asp Val Leu
                645                 650                 655
Ser Lys Leu Leu Val Val Gly Ile Thr Asp Pro Asp Pro Asp Ile Arg
            660                 665                 670
Tyr Cys Val Leu Ala Ser Leu Asp Glu Arg Phe Asp Ala His Leu Ala
        675                 680                 685
```

-continued

```
Gln Ala Glu Asn Leu Gln Ala Leu Phe Val Ala Leu Asn Asp Gln Val
    690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
                740                 745                 750

Ser Ala Arg Met Leu Gly His Leu Val Ser Asn Ala Pro Arg Leu Ile
            755                 760                 765

Arg Pro Tyr Met Glu Pro Ile Leu Lys Ala Leu Ile Leu Lys Leu Lys
770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Met Asp Met Leu Gln Asp Ser Ser
                820                 825                 830

Leu Leu Ala Lys Arg Gln Val Ala Leu Trp Thr Leu Gly Gln Leu Val
            835                 840                 845

Ala Ser Thr Gly Tyr Val Val Glu Pro Tyr Arg Lys Tyr Pro Thr Leu
850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Gly Ala Leu Asp Pro
                885                 890                 895

Tyr Lys His Lys Val Asn Ile Gly Met Ile Asp Gln Ser Arg Asp Ala
                900                 905                 910

Ser Ala Val Ser Leu Ser Glu Ser Lys Ser Ser Gln Asp Ser Ser Asp
            915                 920                 925

Tyr Ser Thr Ser Glu Met Leu Val Asn Met Gly Asn Leu Pro Leu Asp
            930                 935                 940

Glu Phe Tyr Pro Ala Val Ser Met Val Ala Leu Met Arg Ile Phe Arg
945                 950                 955                 960

Asp Gln Ser Leu Ser His His His Thr Met Val Val Gln Ala Ile Thr
                965                 970                 975

Phe Ile Phe Lys Ser Leu Gly Leu Lys Cys Val Gln Phe Leu Pro Gln
                980                 985                 990

Val Met Pro Thr Phe Leu Asn Val Ile Arg Val Cys Asp Gly Ala Ile
                995                 1000                1005

Arg Glu Phe Leu Phe Gln Gln Leu Gly Met Leu Val Ser Phe Val
    1010                1015                1020

Lys Ser His Ile Arg Pro Tyr Met Asp Glu Ile Val Thr Leu Met
    1025                1030                1035

Arg Glu Phe Trp Val Met Asn Thr Ser Ile Gln Ser Thr Ile Ile
    1040                1045                1050

Leu Leu Ile Glu Gln Ile Val Val Ala Leu Gly Gly Glu Phe Lys
    1055                1060                1065

Leu Tyr Leu Pro Gln Leu Ile Pro His Met Leu Arg Val Phe Met
    1070                1075                1080

His Asp Asn Ser Pro Gly Arg Ile Val Ser Ile Lys Leu Leu Ala
    1085                1090                1095

Ala Ile Gln Leu Phe Gly Ala Asn Leu Asp Asp Tyr Leu His Leu
    1100                1105                1110
```

-continued

Leu Leu Pro Pro Ile Val Lys Leu Phe Asp Ala Pro Glu Ala Pro
    1115            1120                1125

Leu Pro Ser Arg Lys Ala Ala Leu Glu Thr Val Asp Arg Leu Thr
    1130            1135                1140

Glu Ser Leu Asp Phe Thr Asp Tyr Ala Ser Arg Ile Ile His Pro
    1145            1150                1155

Ile Val Arg Thr Leu Asp Gln Ser Pro Glu Leu Arg Ser Thr Ala
    1160            1165                1170

Met Asp Thr Leu Ser Ser Leu Val Phe Gln Leu Gly Lys Lys Tyr
    1175            1180                1185

Gln Ile Phe Ile Pro Met Val Asn Lys Val Leu Val Arg His Arg
    1190            1195                1200

Ile Asn His Gln Arg Tyr Asp Val Leu Ile Cys Arg Ile Val Lys
    1205            1210                1215

Gly Tyr Thr Leu Ala Asp Glu Glu Asp Pro Leu Ile Tyr Gln
    1220            1225                1230

His Arg Met Leu Arg Ser Gly Gln Gly Asp Ala Leu Ala Ser Gly
    1235            1240                1245

Pro Val Glu Thr Gly Pro Met Lys Lys Leu His Val Ser Thr Ile
    1250            1255                1260

Asn Leu Gln Lys Ala Trp Gly Ala Ala Arg Arg Val Ser Lys Asp
    1265            1270                1275

Asp Trp Leu Glu Trp Leu Arg Arg Leu Ser Leu Glu Leu Leu Lys
    1280            1285                1290

Asp Ser Ser Ser Pro Ser Leu Arg Ser Cys Trp Ala Leu Ala Gln
    1295            1300                1305

Ala Tyr Asn Pro Met Ala Arg Asp Leu Phe Asn Ala Ala Phe Val
    1310            1315                1320

Ser Cys Trp Ser Glu Leu Asn Glu Asp Gln Gln Asp Glu Leu Ile
    1325            1330                1335

Arg Ser Ile Glu Leu Ala Leu Thr Ser Gln Asp Ile Ala Glu Val
    1340            1345                1350

Thr Gln Thr Leu Leu Asn Leu Ala Glu Phe Met Glu His Ser Asp
    1355            1360                1365

Lys Gly Pro Leu Pro Leu Arg Asp Asp Asn Gly Ile Val Leu Leu
    1370            1375                1380

Gly Glu Arg Ala Ala Lys Cys Arg Ala Tyr Ala Lys Ala Leu His
    1385            1390                1395

Tyr Lys Glu Leu Glu Phe Gln Lys Gly Pro Thr Pro Ala Ile Leu
    1400            1405                1410

Glu Ser Leu Ile Ser Ile Asn Asn Lys Leu Gln Gln Pro Glu Ala
    1415            1420                1425

Ala Ala Gly Val Leu Glu Tyr Ala Met Lys His Phe Gly Glu Leu
    1430            1435                1440

Glu Ile Gln Ala Thr Trp Tyr Glu Lys Leu His Glu Trp Glu Asp
    1445            1450                1455

Ala Leu Val Ala Tyr Asp Lys Lys Met Asp Thr Asn Lys Asp Asp
    1460            1465                1470

Pro Glu Leu Met Leu Gly Arg Met Arg Cys Leu Glu Ala Leu Gly
    1475            1480                1485

Glu Trp Gly Gln Leu His Gln Gln Cys Cys Glu Lys Trp Thr Leu
    1490            1495                1500

Val Asn Asp Glu Thr Gln Ala Lys Met Ala Arg Met Ala Ala Ala

-continued

```
            1505                1510                1515

Ala Ala Trp Gly Leu Gly Gln Trp Asp Ser Met Glu Glu Tyr Thr
    1520                1525                1530

Cys Met Ile Pro Arg Asp Thr His Asp Gly Ala Phe Tyr Arg Ala
    1535                1540                1545

Val Leu Ala Leu His Gln Asp Leu Phe Ser Leu Ala Gln Gln Cys
    1550                1555                1560

Ile Asp Lys Ala Arg Asp Leu Leu Asp Ala Glu Leu Thr Ala Met
    1565                1570                1575

Ala Gly Glu Ser Tyr Ser Arg Ala Tyr Gly Ala Met Val Ser Cys
    1580                1585                1590

His Met Leu Ser Glu Leu Glu Glu Val Ile Gln Tyr Lys Leu Val
    1595                1600                1605

Pro Glu Arg Arg Glu Ile Ile Arg Gln Ile Trp Trp Glu Arg Leu
    1610                1615                1620

Gln Gly Cys Gln Arg Ile Val Glu Asp Trp Gln Lys Ile Leu Met
    1625                1630                1635

Val Arg Ser Leu Val Val Ser Pro His Glu Asp Met Arg Thr Trp
    1640                1645                1650

Leu Lys Tyr Ala Ser Leu Cys Gly Lys Ser Gly Arg Leu Ala Leu
    1655                1660                1665

Ala His Lys Thr Leu Val Leu Leu Leu Gly Val Asp Pro Ser Arg
    1670                1675                1680

Gln Leu Asp His Pro Leu Pro Thr Val His Pro Gln Val Thr Tyr
    1685                1690                1695

Ala Tyr Met Lys Asn Met Trp Lys Ser Ala Arg Lys Ile Asp Ala
    1700                1705                1710

Phe Gln His Met Gln His Phe Val Gln Thr Met Gln Gln Gln Ala
    1715                1720                1725

Gln His Ala Ile Ala Thr Glu Asp Gln Gln His Lys Gln Glu Leu
    1730                1735                1740

His Lys Leu Met Ala Arg Cys Phe Leu Lys Leu Gly Glu Trp Gln
    1745                1750                1755

Leu Asn Leu Gln Gly Ile Asn Glu Ser Thr Ile Pro Lys Val Leu
    1760                1765                1770

Gln Tyr Tyr Ser Ala Ala Thr Glu His Asp Arg Ser Trp Tyr Lys
    1775                1780                1785

Ala Trp His Ala Trp Ala Val Met Asn Phe Glu Ala Val Leu His
    1790                1795                1800

Tyr Lys His Gln Asn Gln Ala Arg Asp Glu Lys Lys Lys Leu Arg
    1805                1810                1815

His Ala Ser Gly Ala Asn Ile Thr Asn Ala Thr Thr Ala Ala Thr
    1820                1825                1830

Thr Ala Ala Thr Ala Thr Thr Thr Ala Ser Thr Glu Gly Ser Asn
    1835                1840                1845

Ser Glu Ser Glu Ala Glu Ser Thr Glu Asn Ser Pro Thr Pro Ser
    1850                1855                1860

Pro Leu Gln Lys Lys Val Thr Glu Asp Leu Ser Lys Thr Leu Leu
    1865                1870                1875

Met Tyr Thr Val Pro Ala Val Gln Gly Phe Phe Arg Ser Ile Ser
    1880                1885                1890

Leu Ser Arg Gly Asn Asn Leu Gln Asp Thr Leu Arg Val Leu Thr
    1895                1900                1905
```

```
Leu Trp Phe Asp Tyr Gly His Trp Pro Asp Val Asn Glu Ala Leu
    1910                1915                1920

Val Glu Gly Val Lys Ala Ile Gln Ile Asp Thr Trp Leu Gln Val
    1925                1930                1935

Ile Pro Gln Leu Ile Ala Arg Ile Asp Thr Pro Arg Pro Leu Val
    1940                1945                1950

Gly Arg Leu Ile His Gln Leu Leu Thr Asp Ile Gly Arg Tyr His
    1955                1960                1965

Pro Gln Ala Leu Ile Tyr Pro Leu Thr Val Ala Ser Lys Ser Thr
    1970                1975                1980

Thr Thr Ala Arg His Asn Ala Ala Asn Lys Ile Leu Lys Asn Met
    1985                1990                1995

Cys Glu His Ser Asn Thr Leu Val Gln Gln Ala Met Met Val Ser
    2000                2005                2010

Glu Glu Leu Ile Arg Val Ala Ile Leu Trp His Glu Met Trp His
    2015                2020                2025

Glu Gly Leu Glu Glu Ala Ser Arg Leu Tyr Phe Gly Glu Arg Asn
    2030                2035                2040

Val Lys Gly Met Phe Glu Val Leu Glu Pro Leu His Ala Met Met
    2045                2050                2055

Glu Arg Gly Pro Gln Thr Leu Lys Glu Thr Ser Phe Asn Gln Ala
    2060                2065                2070

Tyr Gly Arg Asp Leu Met Glu Ala Gln Glu Trp Cys Arg Lys Tyr
    2075                2080                2085

Met Lys Ser Gly Asn Val Lys Asp Leu Thr Gln Ala Trp Asp Leu
    2090                2095                2100

Tyr Tyr His Val Phe Arg Arg Ile Ser Lys Gln Leu Pro Gln Leu
    2105                2110                2115

Thr Ser Leu Glu Leu Gln Tyr Val Ser Pro Lys Leu Leu Met Cys
    2120                2125                2130

Arg Asp Leu Glu Leu Ala Val Pro Gly Thr Tyr Asp Pro Asn Gln
    2135                2140                2145

Pro Ile Ile Arg Ile Gln Ser Ile Ala Pro Ser Leu Gln Val Ile
    2150                2155                2160

Thr Ser Lys Gln Arg Pro Arg Lys Leu Thr Leu Met Gly Ser Asn
    2165                2170                2175

Gly His Glu Phe Val Phe Leu Leu Lys Gly His Glu Asp Leu Arg
    2180                2185                2190

Gln Asp Glu Arg Val Met Gln Leu Phe Gly Leu Val Asn Thr Leu
    2195                2200                2205

Leu Ala Asn Asp Pro Thr Ser Leu Arg Lys Asn Leu Ser Ile Gln
    2210                2215                2220

Arg Tyr Ala Val Ile Pro Leu Ser Thr Asn Ser Gly Leu Ile Gly
    2225                2230                2235

Trp Val Pro His Cys Asp Thr Leu His Ala Leu Ile Arg Asp Tyr
    2240                2245                2250

Arg Glu Lys Lys Lys Ile Leu Leu Asn Ile Glu His Arg Ile Met
    2255                2260                2265

Leu Arg Met Ala Pro Asp Tyr Asp His Leu Thr Leu Met Gln Lys
    2270                2275                2280

Val Glu Val Phe Glu His Ala Val Asn Asn Thr Ala Gly Asp Asp
    2285                2290                2295

Leu Ala Lys Leu Leu Trp Leu Lys Ser Pro Ser Ser Glu Val Trp
    2300                2305                2310
```

Phe Asp Arg Arg Thr Asn Tyr Thr Arg Ser Leu Ala Val Met Ser
    2315                2320                2325

Met Val Gly Tyr Ile Leu Gly Leu Gly Asp Arg His Pro Ser Asn
    2330                2335                2340

Leu Met Leu Asp Arg Leu Ser Gly Lys Ile Leu His Ile Asp Phe
    2345                2350                2355

Gly Asp Cys Phe Glu Val Ala Met Thr Arg Glu Lys Phe Pro Glu
    2360                2365                2370

Lys Ile Pro Phe Arg Leu Thr Arg Met Leu Thr Asn Ala Met Glu
    2375                2380                2385

Val Thr Gly Leu Asp Gly Asn Tyr Arg Ile Thr Cys His Thr Val
    2390                2395                2400

Met Glu Val Leu Arg Glu His Lys Asp Ser Val Met Ala Val Leu
    2405                2410                2415

Glu Ala Phe Val Tyr Asp Pro Leu Leu Asn Trp Arg Leu Met Asp
    2420                2425                2430

Thr Asn Thr Lys Gly Asn Lys Arg Ser Arg Thr Arg Thr Asp Ser
    2435                2440                2445

Tyr Ser Ala Gly Gln Ser Val Glu Ile Leu Asp Gly Val Glu Leu
    2450                2455                2460

Gly Glu Pro Ala His Lys Lys Thr Gly Thr Thr Val Pro Glu Ser
    2465                2470                2475

Ile His Ser Phe Ile Gly Asp Gly Leu Val Lys Pro Glu Ala Leu
    2480                2485                2490

Asn Lys Lys Ala Ile Gln Ile Ile Asn Arg Val Arg Asp Lys Leu
    2495                2500                2505

Thr Gly Arg Asp Phe Ser His Asp Asp Thr Leu Asp Val Pro Thr
    2510                2515                2520

Gln Val Glu Leu Leu Ile Lys Gln Ala Thr Ser His Glu Asn Leu
    2525                2530                2535

Cys Gln Cys Tyr Ile Gly Trp Cys Pro Phe Trp
    2540                2545

<210> SEQ ID NO 21
<211> LENGTH: 403
<212> TYPE: PRT
<213> ORGANISM: Homo sapiens

<400> SEQUENCE: 21

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
                20                  25                  30

Ile Ala Met Gly Phe Pro Ala Glu Arg Leu Glu Gly Val Tyr Arg Asn
            35                  40                  45

Asn Ile Asp Asp Val Val Arg Phe Leu Asp Ser Lys His Lys Asn His
        50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
                100                 105                 110

Ser Glu Asp Asp Asn His Val Ala Ala Ile His Cys Lys Ala Gly Lys
            115                 120                 125

Gly Arg Thr Gly Val Met Ile Cys Ala Tyr Leu Leu His Arg Gly Lys
            130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
            195                 200                 205

Gly Thr Cys Asn Pro Gln Phe Val Val Cys Gln Leu Lys Val Lys Ile
            210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
            275                 280                 285

Lys Val Glu Asn Gly Ser Leu Cys Asp Gln Ile Asp Ser Ile Cys
290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Thr Ser Val Thr Pro Asp
            355                 360                 365

Val Ser Asp Asn Glu Pro Asp His Tyr Arg Tyr Ser Asp Thr Thr Asp
370                 375                 380

Ser Asp Pro Glu Asn Glu Pro Phe Asp Glu Asp Gln His Thr Gln Ile
385                 390                 395                 400

Thr Lys Val

<210> SEQ ID NO 22
<211> LENGTH: 393
<212> TYPE: PRT
<213> ORGANISM: Homo sapiens

<400> SEQUENCE: 22

Met Pro Lys Lys Lys Pro Thr Pro Ile Gln Leu Asn Pro Ala Pro Asp
1               5                   10                  15

Gly Ser Ala Val Asn Gly Thr Ser Ala Glu Thr Asn Leu Glu Ala
            20                  25                  30

Leu Gln Lys Lys Leu Glu Glu Leu Glu Leu Asp Glu Gln Gln Arg Lys
            35                  40                  45

Arg Leu Glu Ala Phe Leu Thr Gln Lys Gln Lys Val Gly Glu Leu Lys
50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

-continued

```
Lys Leu Ile His Leu Glu Ile Lys Pro Ala Ile Arg Asn Gln Ile Ile
                100                 105                 110

Arg Glu Leu Gln Val Leu His Glu Cys Asn Ser Pro Tyr Ile Val Gly
            115                 120                 125

Phe Tyr Gly Ala Phe Tyr Ser Asp Gly Glu Ile Ser Ile Cys Met Glu
130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
            260                 265                 270

Leu Met Phe Gly Cys Gln Val Glu Gly Asp Ala Ala Glu Thr Pro Pro
        275                 280                 285

Arg Pro Arg Thr Pro Gly Arg Pro Leu Ser Ser Tyr Gly Met Asp Ser
290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
        355                 360                 365

Val Asp Phe Ala Gly Trp Leu Cys Ser Thr Ile Gly Leu Asn Gln Pro
370                 375                 380

Ser Thr Pro Thr His Ala Ala Gly Val
385                 390

<210> SEQ ID NO 23
<211> LENGTH: 360
<212> TYPE: PRT
<213> ORGANISM: Homo sapiens

<400> SEQUENCE: 23

Met Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
            20                  25                  30

Glu Gly Ala Tyr Gly Met Val Cys Ser Ala Tyr Asp Asn Val Asn Lys
        35                  40                  45

Val Arg Val Ala Ile Lys Lys Ile Ser Pro Phe Glu His Gln Thr Tyr
    50                  55                  60

Cys Gln Arg Thr Leu Arg Glu Ile Lys Ile Leu Leu Arg Phe Arg His
65                  70                  75                  80
```

```
Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
    130                 135                 140

Val Leu His Arg Asp Leu Lys Pro Ser Asn Leu Leu Leu Asn Thr Thr
145                 150                 155                 160

Cys Asp Leu Lys Ile Cys Asp Phe Gly Leu Ala Arg Val Ala Asp Pro
                165                 170                 175

Asp His Asp His Thr Gly Phe Leu Thr Glu Tyr Val Ala Thr Arg Trp
            180                 185                 190

Tyr Arg Ala Pro Glu Ile Met Leu Asn Ser Lys Gly Tyr Thr Lys Ser
        195                 200                 205

Ile Asp Ile Trp Ser Val Gly Cys Ile Leu Ala Glu Met Leu Ser Asn
    210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
                245                 250                 255

Asn Leu Lys Ala Arg Asn Tyr Leu Leu Ser Leu Pro His Lys Asn Lys
            260                 265                 270

Val Pro Trp Asn Arg Leu Phe Pro Asn Ala Asp Ser Lys Ala Leu Asp
        275                 280                 285

Leu Leu Asp Lys Met Leu Thr Phe Asn Pro His Lys Arg Ile Glu Val
    290                 295                 300

Glu Gln Ala Leu Ala His Pro Tyr Leu Glu Gln Tyr Tyr Asp Pro Ser
305                 310                 315                 320

Asp Glu Pro Ile Ala Glu Ala Pro Phe Lys Phe Asp Met Glu Leu Asp
                325                 330                 335

Asp Leu Pro Lys Glu Lys Leu Lys Glu Leu Ile Phe Glu Glu Thr Ala
            340                 345                 350

Arg Phe Gln Pro Gly Tyr Arg Ser
        355                 360

<210> SEQ ID NO 24
<211> LENGTH: 374
<212> TYPE: PRT
<213> ORGANISM: Homo sapiens

<400> SEQUENCE: 24

Met Trp Phe Leu Thr Thr Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95
```

```
Gln Leu Glu Ile His Arg Gly Trp Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Leu Lys
            340                 345                 350

Cys Gln Glu Gln Lys Glu Gln Leu Gln Gly Val His Arg Lys
        355                 360                 365

Glu Pro Gln Gly Ala Thr
    370

<210> SEQ ID NO 25
<211> LENGTH: 1210
<212> TYPE: PRT
<213> ORGANISM: Homo sapiens

<400> SEQUENCE: 25

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95
```

```
Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
        130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525
```

```
Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
```

```
               945                 950                 955                 960
Phe Arg Glu Leu Ile Ile Glu Phe Ser Lys Met Ala Arg Asp Pro Gln
                    965                 970                 975

Arg Tyr Leu Val Ile Gln Gly Asp Glu Arg Met His Leu Pro Ser Pro
                    980                 985                 990

Thr Asp Ser Asn Phe Tyr Arg Ala Leu Met Asp Glu Glu Asp Met Asp
                    995                1000                1005

Asp Val Val Asp Ala Asp Glu Tyr Leu Ile Pro Gln Gln Gly Phe
        1010                1015                1020

Phe Ser Ser Pro Ser Thr Ser Arg Thr Pro Leu Leu Ser Ser Leu
        1025                1030                1035

Ser Ala Thr Ser Asn Asn Ser Thr Val Ala Cys Ile Asp Arg Asn
        1040                1045                1050

Gly Leu Gln Ser Cys Pro Ile Lys Glu Asp Ser Phe Leu Gln Arg
        1055                1060                1065

Tyr Ser Ser Asp Pro Thr Gly Ala Leu Thr Glu Asp Ser Ile Asp
        1070                1075                1080

Asp Thr Phe Leu Pro Val Pro Glu Tyr Ile Asn Gln Ser Val Pro
        1085                1090                1095

Lys Arg Pro Ala Gly Ser Val Gln Asn Pro Val Tyr His Asn Gln
        1100                1105                1110

Pro Leu Asn Pro Ala Pro Ser Arg Asp Pro His Tyr Gln Asp Pro
        1115                1120                1125

His Ser Thr Ala Val Gly Asn Pro Glu Tyr Leu Asn Thr Val Gln
        1130                1135                1140

Pro Thr Cys Val Asn Ser Thr Phe Asp Ser Pro Ala His Trp Ala
        1145                1150                1155

Gln Lys Gly Ser His Gln Ile Ser Leu Asp Asn Pro Asp Tyr Gln
        1160                1165                1170

Gln Asp Phe Phe Pro Lys Glu Ala Lys Pro Asn Gly Ile Phe Lys
        1175                1180                1185

Gly Ser Thr Ala Glu Asn Ala Glu Tyr Leu Arg Val Ala Pro Gln
        1190                1195                1200

Ser Ser Glu Phe Ile Gly Ala
        1205                1210

<210> SEQ ID NO 26
<211> LENGTH: 1225
<212> TYPE: PRT
<213> ORGANISM: Homo sapiens

<400> SEQUENCE: 26

Met Lys Leu Arg Leu Pro Ala Ser Pro Glu Thr His Leu Asp Met Leu
1               5                  10                  15

Arg His Leu Tyr Gln Gly Cys Gln Val Val Gln Gly Asn Leu Glu Leu
                20                  25                  30

Thr Tyr Leu Pro Thr Asn Ala Ser Leu Ser Phe Leu Gln Asp Ile Gln
        35                  40                  45

Glu Val Gln Gly Tyr Val Leu Ile Ala His Asn Gln Val Arg Gln Val
    50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
```

```
            100                 105                 110
Arg Ser Leu Thr Glu Ile Leu Lys Gly Gly Val Leu Ile Gln Arg Asn
        115                 120                 125

Pro Gln Leu Cys Tyr Gln Asp Thr Ile Leu Trp Lys Asp Ile Phe His
        130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
        195                 200                 205

Gln Cys Ala Ala Gly Cys Thr Gly Pro Lys His Ser Asp Cys Leu Ala
        210                 215                 220

Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
            260                 265                 270

Tyr Leu Ser Thr Asp Val Gly Ser Cys Thr Leu Val Cys Pro Leu His
        275                 280                 285

Asn Gln Glu Val Thr Ala Glu Asp Gly Thr Gln Arg Cys Glu Lys Cys
        290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
            340                 345                 350

Gly Asp Pro Ala Ser Asn Thr Ala Pro Leu Gln Pro Glu Gln Leu Gln
        355                 360                 365

Val Phe Glu Thr Leu Glu Glu Ile Thr Gly Tyr Leu Tyr Ile Ser Ala
        370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415

Gly Leu Gly Ile Ser Trp Leu Gly Leu Arg Ser Leu Arg Glu Leu Gly
            420                 425                 430

Ser Gly Leu Ala Leu Ile His His Asn Thr His Leu Cys Phe Val His
        435                 440                 445

Thr Val Pro Trp Asp Gln Leu Phe Arg Asn Pro His Gln Ala Leu Leu
        450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
            500                 505                 510

Glu Cys Arg Val Leu Gln Gly Leu Pro Arg Glu Tyr Val Asn Ala Arg
        515                 520                 525
```

```
His Cys Leu Pro Cys His Pro Glu Cys Gln Pro Gln Asn Gly Ser Val
    530                 535                 540

Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
                565                 570                 575

Asp Leu Ser Tyr Met Pro Ile Trp Lys Phe Pro Asp Glu Glu Gly Ala
            580                 585                 590

Cys Gln Pro Cys Pro Ile Asn Cys Thr His Ser Cys Val Asp Leu Asp
        595                 600                 605

Asp Lys Gly Cys Pro Ala Glu Gln Arg Ala Ser Pro Leu Thr Ser Ile
610                 615                 620

Ile Ser Ala Val Val Gly Ile Leu Leu Val Val Val Leu Gly Val Val
625                 630                 635                 640

Phe Gly Ile Leu Ile Lys Arg Arg Gln Gln Lys Ile Arg Lys Tyr Thr
                645                 650                 655

Met Arg Arg Leu Leu Gln Glu Thr Glu Leu Val Glu Pro Leu Thr Pro
            660                 665                 670

Ser Gly Ala Met Pro Asn Gln Ala Gln Met Arg Ile Leu Lys Glu Thr
        675                 680                 685

Glu Leu Arg Lys Val Lys Val Leu Gly Ser Gly Ala Phe Gly Thr Val
690                 695                 700

Tyr Lys Gly Ile Trp Ile Pro Asp Gly Glu Asn Val Lys Ile Pro Val
705                 710                 715                 720

Ala Ile Lys Val Leu Arg Glu Asn Thr Ser Pro Lys Ala Asn Lys Glu
                725                 730                 735

Ile Leu Asp Glu Ala Tyr Val Met Ala Gly Val Gly Ser Pro Tyr Val
            740                 745                 750

Ser Arg Leu Leu Gly Ile Cys Leu Thr Ser Thr Val Gln Leu Val Thr
        755                 760                 765

Gln Leu Met Pro Tyr Gly Cys Leu Leu Asp His Val Arg Glu Asn Arg
770                 775                 780

Gly Arg Leu Gly Ser Gln Asp Leu Leu Asn Trp Cys Met Gln Ile Ala
785                 790                 795                 800

Lys Gly Met Ser Tyr Leu Glu Asp Val Arg Leu Val His Arg Asp Leu
                805                 810                 815

Ala Ala Arg Asn Val Leu Val Lys Ser Pro Asn His Val Lys Ile Thr
            820                 825                 830

Asp Phe Gly Leu Ala Arg Leu Leu Asp Ile Asp Glu Thr Glu Tyr His
        835                 840                 845

Ala Asp Gly Gly Lys Val Pro Ile Lys Trp Met Ala Leu Glu Ser Ile
850                 855                 860

Leu Arg Arg Arg Phe Thr His Gln Ser Asp Val Trp Ser Tyr Gly Val
865                 870                 875                 880

Thr Val Trp Glu Leu Met Thr Phe Gly Ala Lys Pro Tyr Asp Gly Ile
                885                 890                 895

Pro Ala Arg Glu Ile Pro Asp Leu Leu Glu Lys Gly Glu Arg Leu Pro
            900                 905                 910

Gln Pro Pro Ile Cys Thr Ile Asp Val Tyr Met Ile Met Val Lys Cys
        915                 920                 925

Trp Met Ile Asp Ser Glu Cys Arg Pro Arg Phe Arg Glu Leu Val Ser
930                 935                 940

Glu Phe Ser Arg Met Ala Arg Asp Pro Gln Arg Phe Val Val Ile Gln
945                 950                 955                 960
```

```
Asn Glu Asp Leu Gly Pro Ala Ser Pro Leu Asp Ser Thr Phe Tyr Arg
            965                 970                 975

Ser Leu Leu Glu Asp Asp Met Gly Asp Leu Val Asp Ala Glu Glu
            980                 985                 990

Tyr Leu Val Pro Gln Gln Gly Phe Phe Cys Pro Asp Pro Ala Pro Gly
            995                 1000                1005

Ala Gly Gly Met Val His His Arg His Arg Ser Ser Ser Thr Arg
            1010                1015                1020

Ser Gly Gly Gly Asp Leu Thr Leu Gly Leu Glu Pro Ser Glu Glu
            1025                1030                1035

Glu Ala Pro Arg Ser Pro Leu Ala Pro Ser Glu Gly Ala Gly Ser
            1040                1045                1050

Asp Val Phe Asp Gly Asp Leu Gly Met Gly Ala Ala Lys Gly Leu
            1055                1060                1065

Gln Ser Leu Pro Thr His Asp Pro Ser Pro Leu Gln Arg Tyr Ser
            1070                1075                1080

Glu Asp Pro Thr Val Pro Leu Pro Ser Glu Thr Asp Gly Tyr Val
            1085                1090                1095

Ala Pro Leu Thr Cys Ser Pro Gln Pro Glu Tyr Val Asn Gln Pro
            1100                1105                1110

Asp Val Arg Pro Gln Pro Pro Ser Pro Arg Glu Gly Pro Leu Pro
            1115                1120                1125

Ala Ala Arg Pro Ala Gly Ala Thr Leu Glu Arg Pro Lys Thr Leu
            1130                1135                1140

Ser Pro Gly Lys Asn Gly Val Val Lys Asp Val Phe Ala Phe Gly
            1145                1150                1155

Gly Ala Val Glu Asn Pro Glu Tyr Leu Thr Pro Gln Gly Gly Ala
            1160                1165                1170

Ala Pro Gln Pro His Pro Pro Ala Phe Ser Pro Ala Phe Asp
            1175                1180                1185

Asn Leu Tyr Tyr Trp Asp Gln Asp Pro Pro Glu Arg Gly Ala Pro
            1190                1195                1200

Pro Ser Thr Phe Lys Gly Thr Pro Thr Ala Glu Asn Pro Glu Tyr
            1205                1210                1215

Leu Gly Leu Asp Val Pro Val
            1220                1225

<210> SEQ ID NO 27
<211> LENGTH: 595
<212> TYPE: PRT
<213> ORGANISM: Homo sapiens

<400> SEQUENCE: 27

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
                20                  25                  30

Ile Pro Leu Glu Arg Pro Leu Gly Glu Val Tyr Leu Asp Ser Ser Lys
            35                  40                  45

Pro Ala Val Tyr Asn Tyr Pro Glu Gly Ala Ala Tyr Glu Phe Asn Ala
        50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95
```

```
Phe Pro Pro Leu Asn Ser Val Ser Pro Ser Leu Met Leu Leu His
            100                 105                 110
Pro Pro Pro Gln Leu Ser Pro Phe Leu Gln Pro His Gly Gln Gln Val
            115                 120                 125
Pro Tyr Tyr Leu Glu Asn Glu Pro Ser Gly Tyr Thr Val Arg Glu Ala
            130                 135                 140
Gly Pro Pro Ala Phe Tyr Arg Pro Asn Ser Asp Asn Arg Arg Gln Gly
145                 150                 155                 160
Gly Arg Glu Arg Leu Ala Ser Thr Asn Asp Lys Gly Ser Met Ala Met
                165                 170                 175
Glu Ser Ala Lys Glu Thr Arg Tyr Cys Ala Val Cys Asn Asp Tyr Ala
                180                 185                 190
Ser Gly Tyr His Tyr Gly Val Trp Ser Cys Glu Gly Cys Lys Ala Phe
            195                 200                 205
Phe Lys Arg Ser Ile Gln Gly His Asn Asp Tyr Met Cys Pro Ala Thr
            210                 215                 220
Asn Gln Cys Thr Ile Asp Lys Asn Arg Arg Lys Ser Cys Gln Ala Cys
225                 230                 235                 240
Arg Leu Arg Lys Cys Tyr Glu Val Gly Met Met Lys Gly Gly Ile Arg
                245                 250                 255
Lys Asp Arg Arg Gly Gly Arg Met Leu Lys His Lys Arg Gln Arg Asp
                260                 265                 270
Asp Gly Glu Gly Arg Gly Glu Val Gly Ser Ala Gly Asp Met Arg Ala
            275                 280                 285
Ala Asn Leu Trp Pro Ser Pro Leu Met Ile Lys Arg Ser Lys Lys Asn
290                 295                 300
Ser Leu Ala Leu Ser Leu Thr Ala Asp Gln Met Val Ser Ala Leu Leu
305                 310                 315                 320
Asp Ala Glu Pro Pro Ile Leu Tyr Ser Glu Tyr Asp Pro Thr Arg Pro
                325                 330                 335
Phe Ser Glu Ala Ser Met Met Gly Leu Leu Thr Asn Leu Ala Asp Arg
            340                 345                 350
Glu Leu Val His Met Ile Asn Trp Ala Lys Arg Val Pro Gly Phe Val
            355                 360                 365
Asp Leu Thr Leu His Asp Gln Val His Leu Leu Glu Cys Ala Trp Leu
            370                 375                 380
Glu Ile Leu Met Ile Gly Leu Val Trp Arg Ser Met Glu His Pro Gly
385                 390                 395                 400
Lys Leu Leu Phe Ala Pro Asn Leu Leu Leu Asp Arg Asn Gln Gly Lys
                405                 410                 415
Cys Val Glu Gly Met Val Glu Ile Phe Asp Met Leu Leu Ala Thr Ser
                420                 425                 430
Ser Arg Phe Arg Met Met Asn Leu Gln Gly Glu Glu Phe Val Cys Leu
            435                 440                 445
Lys Ser Ile Ile Leu Leu Asn Ser Gly Val Tyr Thr Phe Leu Ser Ser
            450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                485                 490                 495
Leu Gln Gln Gln His Gln Arg Leu Ala Gln Leu Leu Leu Ile Leu Ser
            500                 505                 510
His Ile Arg His Met Ser Asn Lys Gly Met Glu His Leu Tyr Ser Met
```

```
               515                 520                 525
Lys Cys Lys Asn Val Val Pro Leu Tyr Asp Leu Leu Leu Glu Met Leu
            530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 28
<211> LENGTH: 920
<212> TYPE: PRT
<213> ORGANISM: Homo sapiens

<400> SEQUENCE: 28

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
                85                  90                  95

Pro Gln Ala His Arg Arg Gly Pro Thr Gly Tyr Leu Val Leu Asp Glu
            100                 105                 110

Glu Gln Gln Pro Ser Gln Pro Gln Ser Ala Leu Glu Cys His Pro Glu
        115                 120                 125

Arg Gly Cys Val Pro Glu Pro Gly Ala Ala Val Ala Ala Ser Lys Gly
    130                 135                 140

Leu Pro Gln Gln Leu Pro Ala Pro Pro Asp Glu Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
            180                 185                 190

Leu Leu Gln Gln Gln Gln Glu Ala Val Ser Glu Gly Ser Ser Ser
        195                 200                 205

Gly Arg Ala Arg Glu Ala Ser Gly Ala Pro Thr Ser Ser Lys Asp Asn
    210                 215                 220

Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
                245                 250                 255

Leu Ser Pro Gly Glu Gln Leu Arg Gly Asp Cys Met Tyr Ala Pro Leu
            260                 265                 270

Leu Gly Val Pro Pro Ala Val Arg Pro Thr Pro Cys Ala Pro Leu Ala
        275                 280                 285

Glu Cys Lys Gly Ser Leu Leu Asp Asp Ser Ala Gly Lys Ser Thr Glu
```

```
            290                 295                 300
Asp Thr Ala Glu Tyr Ser Pro Phe Lys Gly Gly Tyr Thr Lys Gly Leu
305                 310                 315                 320

Glu Gly Glu Ser Leu Gly Cys Ser Gly Ser Ala Ala Gly Ser Ser
                325                 330                 335

Gly Thr Leu Glu Leu Pro Ser Thr Leu Ser Leu Tyr Lys Ser Gly Ala
                340                 345                 350

Leu Asp Glu Ala Ala Ala Tyr Gln Ser Arg Asp Tyr Tyr Asn Phe Pro
                355                 360                 365

Leu Ala Leu Ala Gly Pro Pro Pro Pro Pro Pro His Pro His
            370                 375                 380

Ala Arg Ile Lys Leu Glu Asn Pro Leu Asp Tyr Gly Ser Ala Trp Ala
385                 390                 395                 400

Ala Ala Ala Ala Gln Cys Arg Tyr Gly Asp Leu Ala Ser Leu His Gly
                405                 410                 415

Ala Gly Ala Ala Gly Pro Gly Ser Gly Ser Pro Ser Ala Ala Ala Ser
                420                 425                 430

Ser Ser Trp His Thr Leu Phe Thr Ala Glu Glu Gly Gln Leu Tyr Gly
            435                 440                 445

Pro Cys Gly Gly Gly Gly Gly Gly Gly Gly Gly Gly Gly Gly
450                 455                 460

Gly Gly Gly Gly Gly Gly Gly Gly Glu Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
                500                 505                 510

Pro Tyr Pro Ser Pro Thr Cys Val Lys Ser Glu Met Gly Pro Trp Met
            515                 520                 525

Asp Ser Tyr Ser Gly Pro Tyr Gly Asp Met Arg Leu Glu Thr Ala Arg
530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
                580                 585                 590

Lys Tyr Leu Cys Ala Ser Arg Asn Asp Cys Thr Ile Asp Lys Phe Arg
            595                 600                 605

Arg Lys Asn Cys Pro Ser Cys Arg Leu Arg Lys Cys Tyr Glu Ala Gly
            610                 615                 620

Met Thr Leu Gly Ala Arg Lys Leu Lys Lys Leu Gly Asn Leu Lys Leu
625                 630                 635                 640

Gln Glu Glu Gly Glu Ala Ser Ser Thr Thr Ser Pro Thr Glu Glu Thr
                645                 650                 655

Thr Gln Lys Leu Thr Val Ser His Ile Glu Gly Tyr Glu Cys Gln Pro
            660                 665                 670

Ile Phe Leu Asn Val Leu Glu Ala Ile Glu Pro Gly Val Val Cys Ala
            675                 680                 685

Gly His Asp Asn Asn Gln Pro Asp Ser Phe Ala Ala Leu Leu Ser Ser
            690                 695                 700

Leu Asn Glu Leu Gly Glu Arg Gln Leu Val His Val Val Lys Trp Ala
705                 710                 715                 720
```

```
Lys Ala Leu Pro Gly Phe Arg Asn Leu His Val Asp Asp Gln Met Ala
                725                 730                 735

Val Ile Gln Tyr Ser Trp Met Gly Leu Met Val Phe Ala Met Gly Trp
            740                 745                 750

Arg Ser Phe Thr Asn Val Asn Ser Arg Met Leu Tyr Phe Ala Pro Asp
        755                 760                 765

Leu Val Phe Asn Glu Tyr Arg Met His Lys Ser Arg Met Tyr Ser Gln
    770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
                805                 810                 815

Ile Pro Val Asp Gly Leu Lys Asn Gln Lys Phe Phe Asp Glu Leu Arg
            820                 825                 830

Met Asn Tyr Ile Lys Glu Leu Asp Arg Ile Ile Ala Cys Lys Arg Lys
        835                 840                 845

Asn Pro Thr Ser Cys Ser Arg Arg Phe Tyr Gln Leu Thr Lys Leu Leu
    850                 855                 860

Asp Ser Val Gln Pro Ile Ala Arg Glu Leu His Gln Phe Thr Phe Asp
865                 870                 875                 880

Leu Leu Ile Lys Ser His Met Val Ser Val Asp Phe Pro Glu Met Met
                885                 890                 895

Ala Glu Ile Ile Ser Val Gln Val Pro Lys Ile Leu Ser Gly Lys Val
            900                 905                 910

Lys Pro Ile Tyr Phe His Thr Gln
        915                 920

<210> SEQ ID NO 29
<211> LENGTH: 403
<212> TYPE: PRT
<213> ORGANISM: Homo sapiens

<400> SEQUENCE: 29

Met Asp Arg Ser Lys Glu Asn Cys Ile Ser Gly Pro Val Lys Ala Thr
1               5                   10                  15

Ala Pro Val Gly Gly Pro Lys Arg Val Leu Val Thr Gln Gln Phe Pro
            20                  25                  30

Cys Gln Asn Pro Leu Pro Val Asn Ser Gly Gln Ala Gln Arg Val Leu
        35                  40                  45

Cys Pro Ser Asn Ser Ser Gln Arg Ile Pro Leu Gln Ala Gln Lys Leu
    50                  55                  60

Val Ser Ser His Lys Pro Val Gln Asn Gln Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
            100                 105                 110

Glu Leu Ala Ser Lys Gln Lys Asn Glu Glu Ser Lys Lys Arg Gln Trp
        115                 120                 125

Ala Leu Glu Asp Phe Glu Ile Gly Arg Pro Leu Gly Lys Gly Lys Phe
    130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175
```

-continued

```
Gln Leu Arg Arg Glu Val Glu Ile Gln Ser His Leu Arg His Pro Asn
            180                 185                 190

Ile Leu Arg Leu Tyr Gly Tyr Phe His Asp Ala Thr Arg Val Tyr Leu
        195                 200                 205

Ile Leu Glu Tyr Ala Pro Leu Gly Thr Val Tyr Arg Glu Leu Gln Lys
    210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
                245                 250                 255

Ile Lys Pro Glu Asn Leu Leu Leu Gly Ser Ala Gly Glu Leu Lys Ile
            260                 265                 270

Ala Asp Phe Gly Trp Ser Val His Ala Pro Ser Ser Arg Arg Thr Thr
        275                 280                 285

Leu Cys Gly Thr Leu Asp Tyr Leu Pro Pro Glu Met Ile Glu Gly Arg
    290                 295                 300

Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                325                 330                 335

Thr Tyr Lys Arg Ile Ser Arg Val Glu Phe Thr Phe Pro Asp Phe Val
            340                 345                 350

Thr Glu Gly Ala Arg Asp Leu Ile Ser Arg Leu Leu Lys His Asn Pro
        355                 360                 365

Ser Gln Arg Pro Met Leu Arg Glu Val Leu Glu His Pro Trp Ile Thr
    370                 375                 380

Ala Asn Ser Ser Lys Pro Ser Asn Cys Gln Asn Lys Glu Ser Ala Ser
385                 390                 395                 400

Lys Gln Ser

<210> SEQ ID NO 30
<211> LENGTH: 300
<212> TYPE: PRT
<213> ORGANISM: Homo sapiens

<400> SEQUENCE: 30

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Thr Leu Pro Ser Lys Ser
    50                  55                  60

Asn Glu Ser His Asp His Met Asp Asp Met Asp Glu Asp Asp Asp Asp
65                  70                  75                  80

Asp His Val Asp Ser Gln Asp Ser Ile Asp Ser Asn Asp Ser Asp Asp
                85                  90                  95

Val Asp Asp Thr Asp Asp Ser His Gln Ser Asp Glu Ser His His Ser
            100                 105                 110

Asp Glu Ser Asp Glu Leu Val Thr Asp Phe Pro Thr Asp Leu Pro Ala
        115                 120                 125

Thr Glu Val Phe Thr Pro Val Val Pro Thr Val Asp Thr Tyr Asp Gly
    130                 135                 140
```

-continued

```
Arg Gly Asp Ser Val Val Tyr Gly Leu Arg Ser Lys Ser Lys Phe
145                 150                 155                 160

Arg Arg Pro Asp Ile Gln Tyr Pro Asp Ala Thr Asp Glu Asp Ile Thr
                165                 170                 175

Ser His Met Glu Ser Glu Glu Leu Asn Gly Ala Tyr Lys Ala Ile Pro
            180                 185                 190

Val Ala Gln Asp Leu Asn Ala Pro Ser Asp Trp Asp Ser Arg Gly Lys
        195                 200                 205

Asp Ser Tyr Glu Thr Ser Gln Leu Asp Asp Gln Ser Ala Glu Thr His
    210                 215                 220

Ser His Lys Gln Ser Arg Leu Tyr Lys Arg Lys Ala Asn Asp Glu Ser
225                 230                 235                 240

Asn Glu His Ser Asp Val Ile Asp Ser Gln Glu Leu Ser Lys Val Ser
                245                 250                 255

Arg Glu Phe His Ser His Glu Phe His Ser His Glu Asp Met Leu Val
            260                 265                 270

Val Asp Pro Lys Ser Lys Glu Asp Lys His Leu Lys Phe Arg Ile
        275                 280                 285

Ser His Glu Leu Asp Ser Ala Ser Ser Glu Val Asn
    290                 295                 300

<210> SEQ ID NO 31
<211> LENGTH: 488
<212> TYPE: PRT
<213> ORGANISM: Homo sapiens

<400> SEQUENCE: 31

Met Ala Pro Ala Ala Trp Leu Arg Ser Ala Ala Arg Ala Leu Leu
1               5                   10                  15

Pro Pro Met Leu Leu Leu Leu Gln Pro Pro Pro Leu Leu Ala Arg
                20                  25                  30

Ala Leu Pro Pro Asp Ala His His Leu His Ala Glu Arg Arg Gly Pro
            35                  40                  45

Gln Pro Trp His Ala Ala Leu Pro Ser Ser Pro Ala Pro Ala Pro Ala
        50                  55                  60

Thr Gln Glu Ala Pro Arg Pro Ala Ser Ser Leu Arg Pro Pro Arg Cys
65                  70                  75                  80

Gly Val Pro Asp Pro Ser Asp Gly Leu Ser Ala Arg Asn Arg Gln Lys
                85                  90                  95

Arg Phe Val Leu Ser Gly Gly Arg Trp Glu Lys Thr Asp Ser Leu Thr Tyr
            100                 105                 110

Arg Ile Leu Arg Phe Pro Trp Gln Leu Val Gln Glu Gln Val Arg Gln
        115                 120                 125

Thr Met Ala Glu Ala Leu Lys Val Trp Ser Asp Val Thr Pro Leu Thr
    130                 135                 140

Phe Thr Glu Val His Glu Gly Arg Ala Asp Ile Met Ile Asp Phe Ala
145                 150                 155                 160

Arg Tyr Trp His Gly Asp Asp Leu Pro Phe Asp Gly Pro Gly Gly Ile
                165                 170                 175

Leu Ala His Ala Phe Phe Pro Lys Thr His Arg Glu Gly Asp Val His
            180                 185                 190

Phe Asp Tyr Asp Glu Thr Trp Thr Ile Gly Asp Asp Gln Gly Thr Asp
        195                 200                 205

Leu Leu Gln Val Ala Ala His Glu Phe Gly His Val Leu Gly Leu Gln
    210                 215                 220
```

```
His Thr Thr Ala Ala Lys Ala Leu Met Ser Ala Phe Tyr Thr Phe Arg
225                 230                 235                 240

Tyr Pro Leu Ser Leu Ser Pro Asp Asp Cys Arg Gly Val Gln His Leu
            245                 250                 255

Tyr Gly Gln Pro Trp Pro Thr Val Thr Ser Arg Thr Pro Ala Leu Gly
        260                 265                 270

Pro Gln Ala Gly Ile Asp Thr Asn Glu Ile Ala Pro Leu Glu Pro Asp
    275                 280                 285

Ala Pro Pro Asp Ala Cys Glu Ala Ser Phe Asp Ala Val Ser Thr Ile
290                 295                 300

Arg Gly Glu Leu Phe Phe Phe Lys Ala Gly Phe Val Trp Arg Leu Arg
305                 310                 315                 320

Gly Gly Gln Leu Gln Pro Gly Tyr Pro Ala Leu Ala Ser Arg His Trp
                325                 330                 335

Gln Gly Leu Pro Ser Pro Val Asp Ala Ala Phe Glu Asp Ala Gln Gly
            340                 345                 350

His Ile Trp Phe Phe Gln Ala Gln Tyr Trp Val Tyr Asp Gly Glu
        355                 360                 365

Lys Pro Val Leu Gly Pro Ala Pro Leu Thr Glu Leu Gly Leu Val Arg
370                 375                 380

Phe Pro Val His Ala Ala Leu Val Trp Gly Pro Glu Lys Asn Lys Ile
385                 390                 395                 400

Tyr Phe Phe Arg Gly Arg Asp Tyr Trp Arg Phe His Pro Ser Thr Arg
                405                 410                 415

Arg Val Asp Ser Pro Val Pro Arg Arg Ala Thr Asp Trp Arg Gly Val
            420                 425                 430

Pro Ser Glu Ile Asp Ala Ala Phe Gln Asp Ala Asp Gly Tyr Ala Tyr
        435                 440                 445

Phe Leu Arg Gly Arg Leu Tyr Trp Lys Phe Asp Pro Val Lys Val Lys
    450                 455                 460

Ala Leu Glu Gly Phe Pro Arg Leu Val Gly Pro Asp Phe Phe Gly Cys
465                 470                 475                 480

Ala Glu Pro Ala Asn Thr Phe Leu
                485

<210> SEQ ID NO 32
<211> LENGTH: 432
<212> TYPE: PRT
<213> ORGANISM: Homo sapiens

<400> SEQUENCE: 32

Met Glu Arg Arg Arg Ile Thr Ser Ala Ala Arg Arg Ser Tyr Val Ser
1               5                   10                  15

Ser Gly Glu Met Met Val Gly Gly Leu Ala Pro Gly Arg Arg Leu Gly
            20                  25                  30

Pro Gly Thr Arg Leu Ser Leu Ala Arg Met Pro Pro Pro Leu Pro Thr
        35                  40                  45

Arg Val Asp Phe Ser Leu Ala Gly Ala Leu Asn Ala Gly Phe Lys Glu
    50                  55                  60

Thr Arg Ala Ser Glu Arg Ala Glu Met Met Glu Leu Asn Asp Arg Phe
65                  70                  75                  80

Ala Ser Tyr Ile Glu Lys Val Arg Phe Leu Glu Gln Gln Asn Lys Ala
                85                  90                  95

Leu Ala Ala Glu Leu Asn Gln Leu Arg Ala Lys Glu Pro Thr Lys Leu
            100                 105                 110
```

-continued

```
Ala Asp Val Tyr Gln Ala Glu Leu Arg Glu Leu Arg Leu Arg Leu Asp
            115                 120                 125
Gln Leu Thr Ala Asn Ser Ala Arg Leu Glu Val Glu Arg Asp Asn Leu
    130                 135                 140
Ala Gln Asp Leu Ala Thr Val Arg Gln Lys Leu Gln Asp Glu Thr Asn
145                 150                 155                 160
Leu Arg Leu Glu Ala Glu Asn Asn Leu Ala Ala Tyr Arg Gln Glu Ala
                165                 170                 175
Asp Glu Ala Thr Leu Ala Arg Leu Asp Leu Glu Arg Lys Ile Glu Ser
            180                 185                 190
Leu Glu Glu Glu Ile Arg Phe Leu Arg Lys Ile His Glu Glu Glu Val
            195                 200                 205
Arg Glu Leu Gln Glu Gln Leu Ala Arg Gln Gln Val His Val Glu Leu
    210                 215                 220
Asp Val Ala Lys Pro Asp Leu Thr Ala Ala Leu Lys Glu Ile Arg Thr
225                 230                 235                 240
Gln Tyr Glu Ala Met Ala Ser Ser Asn Met His Glu Ala Glu Glu Trp
                245                 250                 255
Tyr Arg Ser Lys Phe Ala Asp Leu Thr Asp Ala Ala Ala Arg Asn Ala
            260                 265                 270
Glu Leu Leu Arg Gln Ala Lys His Glu Ala Asn Asp Tyr Arg Arg Gln
            275                 280                 285
Leu Gln Ser Leu Thr Cys Asp Leu Glu Ser Leu Arg Gly Thr Asn Glu
    290                 295                 300
Ser Leu Glu Arg Gln Met Arg Glu Gln Glu Arg His Val Arg Glu
305                 310                 315                 320
Ala Ala Ser Tyr Gln Glu Ala Leu Ala Arg Leu Glu Glu Glu Gly Gln
                325                 330                 335
Ser Leu Lys Asp Glu Met Ala Arg His Leu Gln Glu Tyr Gln Asp Leu
            340                 345                 350
Leu Asn Val Lys Leu Ala Leu Asp Ile Glu Ile Ala Thr Tyr Arg Lys
            355                 360                 365
Leu Leu Glu Gly Glu Glu Asn Arg Ile Thr Ile Pro Val Gln Thr Phe
    370                 375                 380
Ser Asn Leu Gln Ile Arg Glu Thr Ser Leu Asp Thr Lys Ser Val Ser
385                 390                 395                 400
Glu Gly His Leu Lys Arg Asn Ile Val Val Lys Thr Val Glu Met Arg
                405                 410                 415
Asp Gly Glu Val Ile Lys Glu Ser Lys Gln Glu His Lys Asp Val Met
            420                 425                 430
```

GENE AND PROTEIN EXPRESSION PROFILES ASSOCIATED WITH THE THERAPEUTIC EFFICACY OF EGFR-TK INHIBITORS

RELATED APPLICATIONS

This application is a continuation of U.S. application Ser. No. 12/072,651, filed Feb. 27, 2008 now abandoned, which in turn claims the benefit under 35 U.S.C. §119(e) to U.S. Provisional Application Ser. No. 60/903,694 filed Feb. 27, 2007, the entirety of which are incorporated herein by reference.

REFERENCE TO SEQUENCES

The instant application contains a Sequence Listing which has been submitted in ASCII format via EFS-Web and is hereby incorporated by reference in its entirety. Said ASCII copy, created on Jun. 8, 2009, is named NUC003SeqList.txt and is 178,374 bytes in size.

BACKGROUND OF THE INVENTION

Patients diagnosed with cancer are faced with costly and often painful treatment options. These treatments may be ineffective in a subpopulation of patients, and as a result, these patients endure these treatments without little or no therapeutic benefit. Some patients may react adversely to certain agents causing additional suffering and possibly death.

Ineffective treatment also is problematic because time is a key variable when treating cancer. A treatment provider has a far greater chance of containing and managing the disease if the cancer is diagnosed at an early stage and treated with a therapeutically effective agent. An agent may provide great therapeutic benefits if administered at an early stage of the disease; however, with the passage of time, the same agent may cease to be effective.

Lung cancer is an example of a condition where early diagnosis is key for effective treatment. Most lung cancers fall into one of two categories: small cell lung cancer and non-small cell lung cancer (NSCLC). NSCLC is the most common type of lung cancer. There are three main subgroups of NSCLC: adenocarcinoma, squamous cell carcinoma and large cell undifferentiated carcinoma.

Chemotherapy often is used for treating NSCLC. Erlotinib (TARCEVA®) is a chemotherapeutic agent indicated for second-line therapy of NSCLC after failure of at least one prior chemotherapy regimen and gefitinib (IRESSA®) is indicated for continued treatment of NSCLC after failure of platinum-based and docetaxel chemotherapies. As with many chemotherapeutic agents, administration of these drugs often causes deleterious side effects for the patient, and some patients do not respond well, or respond at all, to the treatment. Some patients thus undergo treatment with erlotinib or gefitinib and suffer the painful side effects only to later realize that the agent has not been therapeutically beneficial to their condition. In addition to the unnecessary suffering, critical time is lost in determining an alternative treatment.

SUMMARY OF THE INVENTION

The present invention provides gene and protein expression profiles and methods for using them to identify those patients who are likely to respond to treatment with compounds that inhibit the intracellular phosphorylation of tyrosine kinase (TK) associated with epidermal growth factor receptor (EGFR), including erlotinib and gefitinib (these patients are referred to as "responders"), as well as those patients who are not likely to benefit from such treatment (these patients are referred to as "non-responders"). The present invention allows a treatment provider to identify those patients who are responders to treatment with compounds that inhibit the intracellular phosphorylation of EGFR-associated tyrosine kinase, including erlotinib and gefitinib, and those who are non-responders to such treatment, prior to administration of the agent. Compounds such as erlotinib and gefitinib that inhibit the intracellular phosphorylation of EGFR-associated tyrosine kinase are referred to hereinafter as EGFR-TK inhibitors.

The present invention comprises protein expression profiles, as well as the corresponding gene expression profiles (also referred to as "gene signatures") that are indicative of the tendency of a patient afflicted with lung cancer, particularly NSCLC, to respond to treatment with an EGFR-TK inhibitor. The protein expression profile comprises at least one, and preferably a plurality, of proteins selected from the group consisting of p70S6K, phospho-p70S6, phospho-S6, phospho-AKT, phospho-mTOR, phospho-pTEN, phospho MEK, phospho MAPK, phospho-IGFR/, EGFR, phospho-EGFR, phospho-HER2/ErbB2, phospho-ER, phospho-AR, AIK, osteopontin, MMP11 and GFAP. This group of proteins is referred to herein as the "EGFR-TK Inhibitor Responder Proteins". According to the invention, some or all of these proteins are differentially expressed (e.g., up-regulated or down-regulated) in patients who are responders to EGFR-TK inhibitor therapy. Specifically, p70S6K, phospho-S6, phospho-AKT, phospho-mTOR, phospho-pTEN, EGFR, phospho-ER, phospho-AR, AIK, osteopontin, MMP11 and GFAP are up-regulated (over-expressed) and phospho-p70S6, phospho MEK, phospho MAPK, phospho-IGFR/InR, phospho-EGFR and phospho-HER2/ErbB2 are down-regulated (under expressed) in patients who are responders to EGFR-TK inhibitors.

The present invention further comprises gene expression profiles (also referred to as "gene signatures") that are indicative of the tendency of a patient afflicted with NSCLC to respond to treatment with an EGFR-TK inhibitor. The gene expression profile comprises at least one, and preferably a plurality, of genes that encode the proteins selected from the group consisting of p70S6K, phospho-p70S6, phospho-S6, phospho-AKT, phospho-mTOR, phospho-pTEN, phospho MEK, phospho MAPK, phospho-IGFR/InR, EGFR, phospho-EGFR, phospho-HER2/ErbB2, phospho-ER, phospho-AR, AIK, osteopontin, MMP11 and GFAP. This group of genes is referred to herein as the "EGFR-TK Inhibitor Responder Genes". According to the invention, some or all of theses genes are differentially expressed (e.g., up-regulated or down-regulated) in patients who are responders to EGFR-TK inhibitor therapy. Specifically, the genes encoding p70S6K, phospho-S6, phospho-AKT, phospho-mTOR, phospho-pTEN, EGFR, phospho-ER, phospho-AR, AIK, osteopontin, MMP11 and GFAP are up-regulated (over-expressed) and the genes encoding phospho-p70S6, phospho MEK, phospho MAPK, phospho-IGFR/, phospho-EGFR and phospho-HER2/ErbB2 are down-regulated (under expressed) in patients who are responders to EGFR-TK inhibitors.

The present invention further comprises a method of determining if a patient is a responder or non-responder to treatment with an EGFR-TK inhibitor. The method comprises obtaining a tumor sample from the patient, determining the protein and/or gene expression profile of the sample, and determining from the gene expression profile whether at least one protein selected from the to EGFR-TK inhibitor Responder Proteins and/or the EGFR-TK Inhibitor Responder Genes is over- or under-expressed in the sample. From this information, the treatment provider can ascertain whether the patient is likely to benefit from to EGFR-TK inhibitor therapy.

The present invention further comprises an assay for determining the protein and/or gene expression profile in a patient's sample, and instructions for using the assay.

DETAILED DESCRIPTION

The present invention provides gene and protein expression profiles (GPEPs), and their use for predicting a patient's responsiveness to a cancer treatment. More specifically, the present gene and protein expression profiles are indicative of whether a patient afflicted with non small cell lung cancer (NSCLC) is a responder or a non-responder to treatment with a compound which is an EGFR-TK inhibitor, in particular, erlotinib (TARCEVA®) or gefitinib (IRESSA®).

Erlotinib and gefitinib are chemotherapeutic agents which belong to the group of medicines called antineoplastics. These compounds act by inhibiting the intracellular phosphorylation of tyrosine kinase associated with transmembrane cell surface receptors, including EGFR, a receptor expressed on the cell surface of normal cells and cancer cells. These compounds interfere with the growth of cancer cells, which are eventually destroyed.

Significant improvements in the outcomes of NSCLC in some patients treated with erlotinib or gefitinib have been reported. However, the growth of normal cells often is affected by these medicines, causing unwanted and/or unpleasant effects. These other effects may include: diarrhea, rash, acne, dry skin, nausea (feeling sick) and vomiting, loss of appetite and weight loss, asthenia and pruritis and abdominal pain. The present invention provides biomarkers that are associated with those patients that have benefited from treatment with erlotinib and/or gefitinib. The present invention thus enables the treatment provider to determine in advance those NSCLC patients likely to benefit from treatment with erlotinib or gefitinib, and to consider alternative treatment options for non-responders.

In one embodiment, the present invention provides protein expression profiles that are indicative of whether a patient is likely to be a responder or non-responder to EGFR-TK inhibitor therapy. The proteins comprising the expression profile disclosed herein are selected from the group consisting of p70S6K, phospho-p70S6, phospho-S6, phospho-AKT, phospho-mTOR, phospho-pTEN, phospho MEK, phospho MAPK, phospho-IGFR/InR, EGFR, phospho-EGFR, phospho-HER2/ErbB2, phospho-ER, phospho-AR, AIK, osteopontin, MMP11 and GFAP. This group of proteins is referred to herein as the "EGFR-TK Inhibitor Responder Proteins". According to the invention, some or all of these proteins are differentially expressed (e.g., up-regulated or down-regulated) in patients who are responders to EGFR-TK inhibitor therapy. Specifically, p70S6K, phospho-S6, phospho-AKT, phospho-mTOR, phospho-pTEN, EGFR, phospho-ER, phospho-AR, AIK, osteopontin, MMP11 and GFAP are up-regulated (over-expressed) and phospho-p70S6, phospho MEK, phospho MAPK, phospho-IGFR/, phospho-EGFR and phospho-HER2/ErbB2 are down-regulated (under expressed) in patients who are responders to EGFR-TK inhibitors.

Table 1 identifies the EGFR-TK inhibitor Responder Proteins, and indicates whether expression of these proteins is up- or down-regulated in patients that are responders to therapy with an EGFR-TK inhibitor.

TABLE 1

| Protein* Accession No. | Over Expression | Under Expression | SEQ ID No. of Protein |
|---|---|---|---|
| Total p70S6K NP_003152 | Pos | | 17 |
| Phospho-p70S6 Same as above | | Pos | |
| Phospho-S6 NP_001001 | Pos | | 18 |
| Phospho-AKT NP_005154 | Pos | | 19 |
| Phospho-mTOR NP_004949 | Pos | | 20 |
| Phospho-PTEN NP_000305 | Pos | | 21 |
| Phospho MEK NP_002746 | | Pos | 22 |
| Phospho MAPK NP_002736 | | Pos | 23 |
| Phospho-IGFR1/InR NP_000557 | | Pos | 24 |
| Total EGFR NP_005219 | Pos | | 25 |
| Phospho-EGFR Same as above | | Pos | |
| Phospho-HER2(ErbB2) NP_001005862 | | Pos | 26 |
| Phospho-ER NP_000116 | Pos | | 27 |
| Phospho-AR NP_000035 | Pos | | 28 |
| AIK NP_940835 | Pos | | 29 |
| Osteopontin NP_000573 | Pos | | 30 |
| MMP11 NP_005931 | Pos | | 31 |
| GFAP NP_002046 | Pos | | 32 |

*Accession No. refers to non-phosphorylated protein

The present invention further comprises gene expression profiles that are indicative of the tendency of a patient afflicted with NSCLC to respond to treatment with EGFR-TK inhibitors. The gene expression profile comprises at least one, and preferably a plurality, of genes that encode the proteins selected from the group consisting of p70S6K, phospho-p70S6, phospho-S6, phospho-AKT, phospho-mTOR, phospho-pTEN, phospho MEK, phospho MAPK, phospho-IGFR/InR, EGFR, phospho-EGFR, phospho-HER2/ErbB2, phospho-ER, phospho-AR, AIK, osteopontin, MMP11 and GFAP. This group of proteins is referred to herein as the "EGFR-TK Inhibitor Responder Genes". According to the invention, some or all of theses genes are differentially expressed (e.g., up-regulated or down-regulated) in patients who are responders to EGFR-TK inhibitor therapy. Specifically, the genes encoding p70S6K, phospho-S6, phospho-AKT, phospho-mTOR, phospho-pTEN, EGFR, phospho-ER, phospho-AR, AIK, osteopontin, MMP11 and GFAP are up-regulated (over-expressed) and the genes encoding phospho-p70S6, phospho MEK, phospho MAPK, phospho-IGFR/, phospho-EGFR and phospho-HER2/ErbB2 are down-regulated (under expressed) in patients who are responders to EGFR-TK inhibitors. Accordingly, it is possible to determine in advance if a patient is likely to benefit form such therapy by obtaining a gene expression profile from the patient's tissue, and determining whether one or more of the genes in the EGFR-TK inhibitor Responder Genes is up- or down-regulated.

Table 2 identifies the EGFR-TK Inhibitor Responder Genes and indicates whether expression of these genes is up- or down-regulated in patients that are responders to therapy with an EGFR-TK inhibitor. Table 2 also sets forth the NCBI Accession Number of at least one variant of these genes.

TABLE 2

| Gene Accession Number | Encoded Protein | Over Expression | Under Expression | SEQ ID. No. of Genes |
|---|---|---|---|---|
| RPS6KB1 NM_003161 | Total p70S6K | Pos | | 1 |
| Same as above | Phospho-p70S6 | | Pos | |
| RPS6 NM_001010 | Phospho-S6 | Pos | | 2 |
| AKT1 NM_005163 | Phospho-AKT | Pos | | 3 |
| FRAP1 NM_004958 | Phospho-mTOR | Pos | | 4 |
| PTEN NM_000314 | Phospho-PTEN | Pos | | 5 |
| MAP2K1 NM_002755 | Phospho MEK | | Pos | 6 |
| MAPK1 NM_002745 | Phospho MAPK | | Pos | 7 |
| FCGR1A NM_000566 | Phospho-IGFR1/InR | | Pos | 8 |
| EGFR NM_005228 | Total EGFR | Pos | | 9 |
| Same as above | Phospho-EGFR | | Pos | |
| ERBB2 NM_001005862 | Phospho-HER2(ErbB2) | | Pos | 10 |
| ESR1 NM_000125 | Phospho-ER | Pos | | 11 |
| AR NM_000044 | Phospho-AR | Pos | | 12 |
| AURKA NM_198433 | AIK | Pos | | 13 |
| SPP1 NM_000582 | Osteopontin | Pos | | 14 |
| MMP11 NM_005940 | MMP11 | Pos | | 15 |
| GFAP NM_002055 | GFAP | Pos | | 16 |

Other variants of these genes exist (e.g., see the gene databases available through the NCBI Entrez website), and these variants are encompassed by the present invention.

In a preferred aspect of the present invention, the protein expression profiles of the present invention comprise at least about four, preferably between about four and nine, and more preferably between about nine and eighteen of the EGFR-TK Inhibitor Responder Proteins that are up- or down-regulated as applicable. In a currently preferred embodiment, the protein expression profile comprises at least about four, and preferably about six to twelve, of the EGFR-TK Inhibitor Responder Proteins that are up-regulated, and at least about two, and preferably about four to six, of the EGFR-TK Inhibitor Responder Proteins that are down-regulated.

In a preferred aspect of the present invention, the gene expression profiles of the present invention comprise at least about four, preferably between about four and nine, and more preferably between about nine and sixteen of the EGFR-TK Inhibitor Responder Genes that are up- or down-regulated as applicable. In a currently preferred embodiment, the gene expression profile comprises at least about four, and preferably about six to twelve, of the EGFR-TK Inhibitor Responder Genes that are up-regulated, and at least about two, and preferably about four to six, of the EGFR-TK Inhibitor Responder Genes that are down-regulated.

The protein and/or gene expression profiles of the invention can be used to predict the responsiveness of a NSCLC patient to therapy with an EGFR-TK inhibitor, in particular, erlotinib or gefitinib. In one aspect, the present method comprises (a) obtaining a protein or gene expression profile from a tumor sample of a patient afflicted with NSCLC; (b) determining from the protein or gene expression profile whether expression of one or more of the following proteins is up-regulated (over-expressed): p70S6K, phospho-S6, phospho-AKT, phospho-mTOR, phospho-pTEN, EGFR, phospho-ER, phospho-AR, AIK, osteopontin, MMP11 and GFAP; and/or whether expression of at least one of the following proteins is down-regulated (under-expressed): phospho-p70S6, phospho MEK, phospho MAPK, phospho-IGFR/InR, phospho-EGFR and phospho-HER2(ErbB2). The predictive value of the protein or gene profile for determining response to these compounds increases with the number of these proteins or the associated genes that are found to be up- or down-regulated in accordance with the invention. Preferably, at least about four, more preferably between about four and nine, and most preferably between about nine and eighteen of the EGFR-TK Responder Proteins or Genes are differentially expressed.

DEFINITIONS

For convenience, the meaning of certain terms and phrases employed in the specification, examples, and appended claims are provided below. The definitions are not meant to be limiting in nature and serve to provide a clearer understanding of certain aspects of the present invention.

The term "genome" is intended to include the entire DNA complement of an organism, including the nuclear DNA component, chromosomal or extrachromosomal DNA, as well as the cytoplasmic domain (e.g., mitochondrial DNA).

The term "gene" refers to a nucleic acid sequence that comprises control and coding sequences necessary for producing a polypeptide or precursor. The polypeptide may be encoded by a full length coding sequence or by any portion of the coding sequence. The gene may be derived in whole or in part from any source known to the art, including a plant, a fungus, an animal, a bacterial genome or episome, eukaryotic, nuclear or plasmid DNA, cDNA, viral DNA, or chemically synthesized DNA. A gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. The gene may constitute an uninterrupted coding sequence or it may include one or more introns, bound by the appropriate splice junctions. The Term "gene" as used herein includes variants of the genes identified in Table 1.

The term "gene expression" refers to the process by which a nucleic acid sequence undergoes successful transcription and translation such that detectable levels of the nucleotide sequence are expressed.

The terms "gene expression profile" or "gene signature" refer to a group of genes expressed by a particular cell or tissue type wherein presence of the genes taken together or the differential expression of such genes, is indicative/predictive of a certain condition.

The term "nucleic acid" as used herein, refers to a molecule comprised of one or more nucleotides, i.e., ribonucleotides, deoxyribonucleotides, or both. The term includes monomers and polymers of ribonucleotides and deoxyribonucleotides, with the ribonucleotides and/or deoxyribonucleotides being bound together, in the case of the polymers, via 5' to 3' linkages. The ribonucleotide and deoxyribonucleotide polymers may be single or double-stranded. However, linkages may include any of the linkages known in the art including, for example, nucleic acids comprising 5' to 3' linkages. The nucleotides may be naturally occurring or may be synthetically produced analogs that are capable of forming base-pair relationships with naturally occurring base pairs. Examples of non-naturally occurring bases that are capable of forming base-pairing relationships include, but are not limited to, aza and deaza pyrimidine analogs, aza and deaza purine analogs, and other heterocyclic base analogs, wherein one or more of the carbon and nitrogen atoms of the pyrimidine rings have been substituted by heteroatoms, e.g., oxygen, sulfur, selenium, phosphorus, and the like. Furthermore, the term "nucleic acid sequences" contemplates the complementary sequence and specifically includes any nucleic acid sequence that is substantially homologous to the both the nucleic acid sequence and its complement.

The terms "array" and "microarray" refer to the type of genes or proteins represented on an array by oligonucleotides or protein-capture agents, and where the type of genes or proteins represented on the array is dependent on the intended purpose of the array (e.g., to monitor expression of human genes or proteins). The oligonucleotides or protein-capture agents on a given array may correspond to the same type, category, or group of genes or proteins. Genes or proteins may be considered to be of the same type if they share some common characteristics such as species of origin (e.g., human, mouse, rat); disease state (e.g., cancer); functions (e.g., protein kinases, tumor suppressors); or same biological process (e.g., apoptosis, signal transduction, cell cycle regulation, proliferation, differentiation). For example, one array type may be a "cancer array" in which each of the array oligonucleotides or protein-capture agents correspond to a gene or protein associated with a cancer. An "epithelial array" may be an array of oligonucleotides or protein-capture agents corresponding to unique epithelial genes or proteins. Similarly, a "cell cycle array" may be an array type in which the oligonucleotides or protein-capture agents correspond to unique genes or proteins associated with the cell cycle.

The term "cell type" refers to a cell from a given source (e.g., a tissue, organ) or a cell in a given state of differentiation, or a cell associated with a given pathology or genetic makeup.

The term "activation" as used herein refers to any alteration of a signaling pathway or biological response including, for example, increases above basal levels, restoration to basal levels from an inhibited state, and stimulation of the pathway above basal levels.

The term "differential expression" refers to both quantitative as well as qualitative differences in the temporal and tissue expression patterns of a gene or a protein in diseased tissues or cells versus normal adjacent tissue. For example, a differentially expressed gene may have its expression activated or completely inactivated in normal versus disease conditions, or may be up-regulated (over-expressed) or down-regulated (under-expressed) in a disease condition versus a normal condition. Such a qualitatively regulated gene may exhibit an expression pattern within a given tissue or cell type that is detectable in either control or disease conditions, but is not detectable in both. Stated another way, a gene or protein is differentially expressed when expression of the gene or protein occurs at a higher or lower level in the diseased tissues or cells of a patient relative to the level of its expression in the normal (disease-free) tissues or cells of the patient and/or control tissues or cells.

The term "detectable" refers to an RNA expression pattern which is detectable via the standard techniques of polymerase chain reaction (PCR), reverse transcriptase-(RT) PCR, differential display, and Northern analyses, which are well known to those of skill in the art. Similarly, protein expression patterns may be "detected" via standard techniques such as Western blots.

The term "complementary" refers to the topological compatibility or matching together of the interacting surfaces of a probe molecule and its target. The target and its probe can be described as complementary, and furthermore, the contact surface characteristics are complementary to each other. Hybridization or base pairing between nucleotides or nucleic acids, such as, for example, between the two strands of a double-stranded DNA molecule or between an oligonucleotide probe and a target are complementary.

The term "biological sample" refers to a sample obtained from an organism (e.g., a human patient) or from components (e.g., cells) of an organism. The sample may be of any biological tissue or fluid. The sample may be a "clinical sample" which is a sample derived from a patient. Such samples include, but are not limited to, sputum, blood, blood cells (e.g., white cells), amniotic fluid, plasma, semen, bone marrow, and tissue or fine needle biopsy samples, urine, peritoneal fluid, and pleural fluid, or cells therefrom. Biological samples may also include sections of tissues such as frozen sections taken for histological purposes. A biological sample may also be referred to as a "patient sample."

A "protein" means a polymer of amino acid residues linked together by peptide bonds. The term, as used herein, refers to proteins, polypeptides, and peptides of any size, structure, or function. Typically, however, a protein will be at least six amino acids long. If the protein is a short peptide, it will be at least about 10 amino acid residues long. A protein may be naturally occurring, recombinant, or synthetic, or any combination of these. A protein may also comprise a fragment of a naturally occurring protein or peptide. A protein may be a single molecule or may be a multi-molecular complex. The term protein may also apply to amino acid polymers in which one or more amino acid residues is an artificial chemical analogue of a corresponding naturally occurring amino acid.

A "fragment of a protein," as used herein, refers to a protein that is a portion of another protein. For example, fragments of proteins may comprise polypeptides obtained by digesting full-length protein isolated from cultured cells. In one embodiment, a protein fragment comprises at least about six amino acids. In another embodiment, the fragment comprises at least about ten amino acids. In yet another embodiment, the protein fragment comprises at least about sixteen amino acids.

As used herein, an "expression product" is a biomolecule, such as a protein, which is produced when a gene in an organism is expressed. An expression product may comprise post-translational modifications.

The term "protein expression" refers to the process by which a nucleic acid sequence undergoes successful transcription and translation such that detectable levels of the amino acid sequence or protein are expressed.

The terms "protein expression profile" or "protein expression signature" refer to a group of proteins expressed by a particular cell or tissue type (e.g., neuron, coronary artery endothelium, or disease tissue), wherein presence of the proteins taken together or the differential expression of such proteins, is indicative/predictive of a certain condition.

The term "antibody" means an immunoglobulin, whether natural or partially or wholly synthetically produced. All derivatives thereof that maintain specific binding ability are also included in the term. The term also covers any protein having a binding domain that is homologous or largely homologous to an immunoglobulin binding domain. An antibody may be monoclonal or polyclonal. The antibody may be a member of any immunoglobulin class, including any of the human classes: IgG, IgM, IgA, IgD, and IgE.

The term "antibody fragment" refers to any derivative of an antibody that is less than full-length. In one aspect, the antibody fragment retains at least a significant portion of the full-length antibody's specific binding ability, specifically, as a binding partner. Examples of antibody fragments include, but are not limited to, Fab, Fab', F(ab')$_2$, scFv, Fv, dsFv diabody, and Fd fragments. The antibody fragment may be produced by any means. For example, the antibody fragment may be enzymatic ally or chemically produced by fragmentation of an intact antibody or it may be recombinantly produced from a gene encoding the partial antibody sequence. Alternatively, the antibody fragment may be wholly or partially synthetically produced. The antibody fragment may comprise a single chain antibody fragment. In another embodiment, the fragment may comprise multiple chains that are linked together, for example, by disulfide linkages. The fragment may also comprise a multimolecular complex. A functional antibody fragment may typically comprise at least about 50 amino acids and more typically will comprise at least about 200 amino acids.

Determination of Gene Expression Profiles

The following method was used to identify and validate gene expression profiles indicative of whether the patient will respond to treatment with an EGFR-TK inhibitor. Other methods for identifying gene and/or protein expression profiles are known; any of these alternative methods also could be used. See, e.g., Chen et al., *NEJM,* 356(1):11-20 (2007); Lu et al., *PLOS Med.,* 3(12):e467 (2006); Golub et al., *Science,* 286:531-537 (1999).

The present method utilizes parallel testing in which, in one track, those genes which are over-/under-expressed as compared to normal (non-cancerous) tissue samples are identified, and, in a second track, those genes comprising chromosomal insertions or deletions as compared to normal samples are identified, from the same samples. These two tracks of analysis produce two sets of data. The data are analyzed using an algorithm which identifies the genes of the gene expression profile (i.e., those genes that are differentially expressed in cancer tissue). Positive and negative controls may be employed to normalize the results, including eliminating those genes and proteins that also are differentially expressed in normal tissues from the same patients, and confirming that the gene expression profile is unique to the cancer of interest.

In the present instance, as an initial step, biological samples from about two hundred fifty (250) patients afflicted with NSCLC were acquired. Approximately five-hundred (500) tissue samples obtained from NSCLC cancer patients were used, including tumor tissue and adjacent normal (undiseased) lung tissue. The tissue samples were obtained from patients suffering from various stages of NSCLC cancer. The samples included tumor tissue from patients who had been treated with erlotinib or gefitinib; some of the patients were responders to these compounds and others were non-responders. Clinical information associated with each sample, including treatment with erlotinib or gefitinib and the outcome of the treatment (e.g., length of survival), was recorded in a database. Clinical information also includes information such as age, sex, medical history, treatment history, symptoms, family history, recurrence (yes/no), etc. Control samples, including samples of normal (non-cancerous) lung tissue from the same patients, and other types of cancerous tissue from other patients (e.g., from a tissue repository) also were acquired. Samples of normal undiseased lung tissue from a set of healthy individuals were used as positive controls, and tumor samples from NSCLC patients who were non-responders to with erlotinib or gefitinib therapy were used as negative controls.

Gene expression profiles (GEPs) then were generated from the biological samples based on total RNA according to well-established methods. Briefly, a typical method involves isolating total RNA from the biological sample, amplifying the RNA, synthesizing cDNA, labeling the cDNA with a detectable label, hybridizing the cDNA with a genomic array, such as the Affymetrix U133 GeneChip®, and determining binding of the labeled cDNA with the genomic array by measuring the intensity of the signal from the detectable label bound to the array. See, e.g., the methods described in Lu, et al., Chen, et al. and Golub, et al., supra, and the references cited therein, which are incorporated herein by reference. The resulting expression data are input into a database.

MRNAs in the tissue samples can be analyzed using commercially available or customized probes or oligonucleotide arrays, such as cDNA or oligonucleotide arrays. The use of these arrays allows for the measurement of steady-state mRNA levels of thousands of genes simultaneously, thereby presenting a powerful tool for identifying effects such as the onset, arrest or modulation of uncontrolled cell proliferation. Hybridization and/or binding of the probes on the arrays to the nucleic acids of interest from the cells can be determined by detecting and/or measuring the location and intensity of the signal received from the labeled probe or used to detect a DNA/RNA sequence from the sample that hybridizes to a nucleic acid sequence at a known location on the microarray. The intensity of the signal is proportional to the quantity of cDNA or mRNA present in the sample tissue. Numerous arrays and techniques are available and useful. Methods for determining gene and/or protein expression in sample tissues are described, for example, in U.S. Pat. No. 6,271,002; U.S. Pat. No. 6,218,122; U.S. Pat. No. 6,218,114; and U.S. Pat. No. 6,004,755; and in Wang et al., *J. Clin. Oncol.,* 22(9): 1564-1671 (2004); Golub et al, (supra); and Schena et al., *Science,* 270:467-470 (1995); all of which are incorporated herein by reference.

The gene analysis aspect utilized in the present method investigates gene expression as well as insertion/deletion data. As a first step, RNA was isolated from the tissue samples and labeled. Parallel processes were run on the sample to develop two sets of data: (1) over-/under-expression of genes based on mRNA levels; and (2) chromosomal insertion/deletion data. These two sets of data were then correlated by means of an algorithm. Over-/under-expression of the genes in each cancer tissue sample were compared to gene expression in the normal (non-cancerous) samples, and a subset of genes that were differentially expressed in the cancer tissue was identified. Preferably, levels of up- and down-regulation are distinguished based on fold changes of the intensity measurements of hybridized microarray probes. A difference of about 2.0 fold or greater is preferred for making such distinctions, or a p-value of less than about 0.05. That is, before a gene is said to be differentially expressed in diseased versus normal cells, the diseased cell is found to yield at least about 2 times greater or less intensity of expression than the normal cells. Generally, the greater the fold difference (or the lower the p-value), the more preferred is the gene for use as a diagnostic or prognostic tool. Genes selected for the gene signatures of the present invention have expression levels that result in the generation of a signal that is distinguishable from those of the normal or non-modulated genes by an amount that exceeds background using clinical laboratory instrumentation.

Statistical values can be used to confidently distinguish modulated from non-modulated genes and noise. Statistical tests can identify the genes most significantly differentially expressed between diverse groups of samples. The Student's t-test is an example of a robust statistical test that can be used to find significant differences between two groups. The lower the p-value, the more compelling the evidence that the gene is showing a difference between the different groups. Nevertheless, since microarrays allow measurement of more than one gene at a time, tens of thousands of statistical tests may be asked at one time. Because of this, it is unlikely to observe small p-values just by chance, and adjustments using a Sidak correction or similar step as well as a randomization/permutation experiment can be made. A p-value less than about 0.05 by the t-test evidence that the expression level of the gene is significantly different. More compelling evidence is a p-value less then about 0.05 after the Sidak correction is factored in. For a large number of samples in each group, a p-value less than about 0.05 after the randomization/permutation test is the most compelling evidence of a significant difference.

Another parameter that can be used to select genes that generate a signal that is greater than that of the non-modulated gene or noise is the measurement of absolute signal difference. Preferably, the signal generated by the differentially expressed genes differs by at least about 20% from those of the normal or non-modulated gene (on an absolute basis). It is even more preferred that such genes produce expression patterns that are at least about 30% different than those of normal or non-modulated genes.

This differential expression analysis can be performed using commercially available arrays, for example, Affymetrix U133 GeneChip® arrays (Affymetrix, Inc.). These arrays have probe sets for the whole human genome immobilized on the chip, and can be used to determine up- and down-regulation of genes in test samples. Other substrates having affixed thereon human genomic DNA or probes capable of detecting expression products, such as those available from Affymetrix, Agilent Technologies, Inc. or Illumina, Inc., also may be used. Currently preferred gene microarrays for use in the present invention include Affymetrix U133 GeneChip® arrays and Agilent Technologies genomic cDNA microarrays. Instruments and reagents for performing gene expression analysis are commercially available. See, e.g., Affymetrix GeneChip® System The expression data obtained from the analysis then is input into the database.

In the second arm of the present method, chromosomal insertion/deletion data for the genes of each sample as compared to samples of normal tissue was obtained. The insertion/deletion analysis was generated using an array-based comparative genomic hybridization ("CGH"). Array CGH measures copy-number variations at multiple loci simultaneously, providing an important tool for studying cancer and developmental disorders and for developing diagnostic and therapeutic targets. Microchips for performing array CGH are commercially available, e.g., from Agilent Technologies. The Agilent chip is a chromosomal array which shows the location of genes on the chromosomes and provides additional data for the gene signature. The insertion/deletion data from this testing is input into the database.

The analyses are carried out on the same samples from the same patients to generate parallel data. The same chips and sample preparation are used to reduce variability.

The expression of certain genes known as "reference genes" "control genes" or "housekeeping genes" also is determined, preferably at the same time, as a means of ensuring the veracity of the expression profile. Reference genes are genes that are consistently expressed in many tissue types, including cancerous and normal tissues, and thus are useful to normalize gene expression profiles. See, e.g., Silvia et al., *BMC Cancer*, 6:200 (2006); Lee et al., *Genome Research*, 12(2):292-297 (2002); Zhang et al., *BMC Mol. Biol.*, 6:4 (2005). Determining the expression of reference genes in parallel with the genes in the unique gene expression profile provides further assurance that the techniques used for determination of the gene expression profile are working properly. Any reference genes can be used in the present method and assay, including, for example, ACTB, GAPD, GUSB, RPLP0 and/or TRFC.

Data Correlation

The differential expression data and the insertion/deletion data in the database are correlated with the clinical outcomes information associated with each tissue sample also in the database by means of an algorithm to determine a gene expression profile for determining therapeutic efficacy of irinotecan, as well as late recurrence of disease and/or disease-related death associated with irinotecan therapy. Various algorithms are available which are useful for correlating the data and identifying the predictive gene signatures. For example, algorithms such as those identified in Xu et al., A Smooth Response Surface Algorithm For Constructing A Gene Regulatory Network, *Physiol. Genomics* 11:11-20 (2002), the entirety of which is incorporated herein by reference, may be used for the practice of the embodiments disclosed herein.

Another method for identifying gene expression profiles is through the use of optimization algorithms such as the mean variance algorithm widely used in establishing stock portfolios. One such method is described in detail in the patent application US Patent Application Publication No. 2003/0194734. Essentially, the method calls for the establishment of a set of inputs expression as measured by intensity) that will optimize the return (signal that is generated) one receives for using it while minimizing the variability of the return. The algorithm described in Irizarry et al., *Nucleic Acids Res.*, 31:e15 (2003) also may be used. The currently preferred algorithm is the JMP Genomics algorithm available from JMP Software.

The process of selecting gene expression profiles also may include the application of heuristic rules. Such rules are formulated based on biology and an understanding of the technology used to produce clinical results, and are applied to output from the optimization method. For example, the mean variance method of gene signature identification can be applied to microarray data for a number of genes differentially expressed in subjects with cancer. Output from the method would be an optimized set of genes that could include some genes that are expressed in peripheral blood as well as in diseased tissue. If samples used in the testing method are obtained from peripheral blood and certain genes differentially expressed in instances of cancer could also be differentially expressed in peripheral blood, then a heuristic rule can be applied in which a portfolio is selected from the efficient frontier excluding those that are differentially expressed in peripheral blood. Of course, the rule can be applied prior to the formation of the efficient frontier by, for example, applying the rule during data pre-selection.

Other heuristic rules can be applied that are not necessarily related to the biology in question. For example, one can apply a rule that only a certain percentage of the portfolio can be represented by a particular gene or group of genes. Commercially available software such as the Wagner software readily accommodates these types of heuristics (Wagner Associates Mean-Variance Optimization Application). This can be useful, for example, when factors other than accuracy and precision have an impact on the desirability of including one or more genes.

As an example, the algorithm may be used for comparing gene expression profiles for various genes (or portfolios) to ascribe prognoses. The gene expression profiles of each of the genes comprising the portfolio are fixed in a medium such as a computer readable medium. This can take a number of forms. For example, a table can be established into which the range of signals (e.g., intensity measurements) indicative of disease is input. Actual patient data can then be compared to the values in the table to determine whether the patient samples are normal or diseased. In a more sophisticated embodiment, patterns of the expression signals (e.g., fluorescent intensity) are recorded digitally or graphically. The gene expression patterns from the gene portfolios used in conjunction with patient samples are then compared to the expression patterns. Pattern comparison software can then be used to determine whether the patient samples have a pattern indicative of recurrence of the disease. Of course, these comparisons can also be used to determine whether the patient is not likely to experience disease recurrence. The expression profiles of the samples are then compared to the profile of a control cell. If the sample expression patterns are consistent with the expression pattern for recurrence of cancer then (in the absence of countervailing medical considerations) the patient is treated as one would treat a relapse patient. If the sample expression patterns are consistent with the expression pattern from the normal/control cell then the patient is diagnosed negative for the cancer.

A method for analyzing the gene signatures of a patient to determine prognosis of cancer is through the use of a Cox hazard analysis program. The analysis may be conducted using S-Plus software (commercially available from Insightful Corporation). Using such methods, a gene expression profile is compared to that of a profile that confidently represents relapse (i.e., expression levels for the combination of genes in the profile is indicative of relapse). The Cox hazard model with the established threshold is used to compare the similarity of the two profiles (known relapse versus patient) and then determines whether the patient profile exceeds the threshold. If it does, then the patient is classified as one who will relapse and is accorded treatment such as adjuvant therapy. If the patient profile does not exceed the threshold then they are classified as a non-relapsing patient. Other analytical tools can also be used to answer the same question such as, linear discriminate analysis, logistic regression and neural network approaches. See, e.g., software available from JMP statistical software.

Numerous other well-known methods of pattern recognition are available. The following references provide some examples:

Weighted Voting: Golub, T R., Slonim, D K., Tamaya, P., Huard, C., Gaasenbeek, M., Mesirov, J P., Coller, H., Loh, L., Downing, J R., Caligiuri, M A., Bloomfield, C D., Lander, E S. Molecular classification of cancer: class discovery and class prediction by gene expression monitoring. Science 286: 531-537, 1999.

Support Vector Machines: Su, A I., Welsh, J B., Sapinoso, L M., Kern, S G., Dimitrov, P., Lapp, H., Schultz, P G., Powell, S M., Moskaluk, C A., Frierson, H F. Jr., Hampton, G M. Molecular classification of human carcinomas by use of gene expression signatures. Cancer Research 61:7388-93, 2001. Ramaswamy, S., Tamayo, P., Rifkin, R., Mukherjee, S., Yeang, C H., Angelo, M., Ladd, C., Reich, M., Latulippe, E., Mesirov, J P., Poggio, T., Gerald, W., Loda, M., Lander, E S., Gould, T R. Multiclass cancer diagnosis using tumor gene expression signatures Proceedings of the National Academy of Sciences of the USA 98:15149-15154, 2001.

K-nearest Neighbors: Ramaswamy, S., Tamayo, P., Rifkin, R., Mukherjee, S., Yeang, C H., Angelo, M., Ladd, C., Reich, M., Latulippe, E., Mesirov, J P., Poggio, T., Gerald, W., Loda, M., Lander, E S., Gould, T R. Multiclass cancer diagnosis using tumor gene expression signatures Proceedings of the National Academy of Sciences of the USA 98:15149-15154, 2001.

Correlation Coefficients: van't Veer L J, Dai H, van de Vijver M J, He Y D, Hart A, Mao M, Peterse H L, van der Kooy K, Marton M J, Witteveen A T, Schreiber G J, Kerkhoven R M, Roberts C, Linsley P S, Bernards R, Friend S H. Gene expression profiling predicts clinical outcome of breast cancer, Nature. 2002 Jan. 31; 415(6871):530-6.

The gene expression analysis identifies a gene expression profile (GEP) unique to the cancer samples, that is, those genes which are differentially expressed by the cancer cells. This GEP then is validated, for example, using real-time quantitative polymerase chain reaction (RT-qPCR), which may be carried out using commercially available instruments and reagents, such as those available from Applied Biosystems.

In the present instance, the results of the gene expression analysis showed that in NSCLC cancer patients who were responsive to treatment with an EGFR-TK inhibitor, the genes encoding p70S6K, phospho-S6, phospho-AKT, phospho-mTOR, phospho-pTEN, EGFR, phospho-ER, phospho-AR, AIK, osteopontin, MMP11 and GFAP are up-regulated (over-expressed) and the genes encoding phospho-p70S6, phospho MEK, phospho MAPK, phospho-IGFR/, phospho-EGFR and phospho-HER2/ErbB2 are down-regulated (under expressed) in patients who are responders to EGFR-TK inhibitors, compared with expression of these genes in the normal lung tissue samples from these patients, and from the negative control patients, i.e., the tissue samples from patients that had experienced a recurrence of their cancer after treatment with an EGFR-TK inhibitor. The reference genes used in the present invention, ACTB, GAPD, GUSB, RPLP0 and TRFC, all were up-regulated.

Determination of Protein Expression Profiles

Not all genes expressed by a cell are translated into proteins, therefore, once a GEP has been identified, it is desirable to ascertain whether proteins corresponding to some or all of the differentially expressed genes in the GEP also are differentially expressed by the same cells or tissue. Therefore, protein expression profiles (PEPs) are generated from the same cancer and control tissues used to identify the GEPs. PEPs also are used to validate the GEP in other colon cancer patients.

The preferred method for generating PEPs according to the present invention is by immunohistochemistry (IHC) analysis. In this method antibodies specific for the proteins in the PEP are used to interrogate tissue samples from cancer patients. Other methods for identifying PEPs are known, e.g. in situ hybridization (ISH) using protein-specific nucleic acid probes. See, e.g., Hofer et al., *Clin. Can. Res.,* 11(16):5722 (2005); Volm et al., *Clin. Exp. Metas.,* 19(5):385 (2002). Any of these alternative methods also could be used.

In the present instance, samples of tumor tissue and normal tissue were obtained from patients afflicted with NSCLC who had undergone successful treatment with gefitinib or with 5-FU, docetaxel or cisplatin, these are the same samples used for identifying the GEP. The tissue samples were arrayed on tissue microarrays (TMAs) to enable simultaneous analysis.

TMAs consist of substrates, such as glass slides, on which up to about 1000 separate tissue samples are assembled in array fashion to allow simultaneous histological analysis. The tissue samples may comprise tissue obtained from preserved biopsy samples, e.g., paraffin-embedded or frozen tissues. Techniques for making tissue microarrays are well-known in the art. See, e.g., Simon et al., *BioTechniques*, 36(1):98-105 (2004); Kallioniemi et al, WO 99/44062; Kononen et al., *Nat. Med.*, 4:844-847 (1998). In the present instance, a hollow needle was used to remove tissue cores as small as 0.6 mm in diameter from regions of interest in paraffin embedded tissues. The "regions of interest" are those that have been identified by a pathologist as containing the desired diseased or normal tissue. These tissue cores then were inserted in a recipient paraffin block in a precisely spaced array pattern. Sections from this block were cut using a microtome, mounted on a microscope slide and then analyzed by standard histological analysis. Each microarray block can be cut into approximately 100 to approximately 500 sections, which can be subjected to independent tests.

The TMAs were prepared using two tissue samples from each patient: one of NSCLC tumor tissue and one of normal lung tissue. Control arrays also were prepared; in a currently preferred embodiment, the following control TMAs were used: an array containing normal lung tissue samples from healthy, cancer-free individuals; an array of "positive controls" containing tumor tissues from cancer patients afflicted with cancers other than NSCLC, e.g., breast cancer, colon cancer, and prostate cancer; and an array of "negative controls" containing tumor samples from NSCLC cancer patients that had experienced recurrences of the cancer after treatment with an EGFR-TK inhibitor—that is, patients who were "non-responders" to the therapy.

Proteins in the tissue samples may be analyzed by interrogating the TMAs using protein-specific agents, such as antibodies or nucleic acid probes, such as aptamers. Antibodies are preferred for this purpose due to their specificity and availability. The antibodies may be monoclonal or polyclonal antibodies, antibody fragments, and/or various types of synthetic antibodies, including chimeric antibodies, or fragments thereof. Antibodies are commercially available from a number of sources (e.g., Abcam, Cell Signaling Technology, Santa Cruz Biotechnology), or may be generated using techniques well-known to those skilled in the art. The antibodies typically are equipped with detectable labels, such as enzymes, chromogens or quantum dots that permit the antibodies to be detected. The antibodies may be conjugated or tagged directly with a detectable label, or indirectly with one member of a binding pair, of which the other member contains a detectable label. Detection systems for use with are described, for example, in the website of Ventana Medical Systems, Inc. Quantum dots are particularly useful as detectable labels. The use of quantum dots is described, for example, in the following references: Jaiswal et al., *Nat. Biotechnol.*, 21:47-51 (2003); Chan et al., *Curr. Opin. Biotechnol.*, 13:40-46 (2002); Chan et al., *Science*, 281:435-446 (1998).

The use of antibodies to identify proteins of interest in the cells of a tissue, referred to as immunohistochemistry (IHC), is well established. See, e.g., Simon et al., *BioTechniques*, 36(1):98 (2004); Haedicke et al., *BioTechniques*, 35(1):164 (2003), which are hereby incorporated by reference. The IHC assay can be automated using commercially available instruments, such as the Benchmark instruments available from Ventana Medical Systems, Inc.

In the present instance, the TMAs were contacted with antibodies specific for the proteins encoded by the genes identified in the gene expression study as being up- or down-regulated in NSCLC cancer patients who were responders to therapy with an EGFR-Tk inhibitor in order to determine expression of these proteins in each type of tissue. The results of the immunohistochemical assay showed the following:

In NSCLC patients that were responsive to treatment with an EGFR-TK inhibitor, the following proteins were up-regulated: p70S6K, phospho-S6, phospho-AKT, phospho-mTOR, phospho-pTEN, EGFR, phospho-ER, phospho-AR. AIK, osteopontin, MMP11 and GFAP; and the following proteins were down-regulated: phospho-p70S6, phospho-MEK, phospho-MAPK, phospho-IGFR1/InR, phospho-EGFR and phospho-HER2, compared with an expression of these proteins in normal lung tissue from these patients and the normal lung tissue from other patients;

A majority of the EGFR-TK Inhibitor Responder Proteins were not up- or down-regulated in the positive control tissue samples; and The EGFR-TK Inhibitor Responder Proteins were not up- or down-regulated in the negative control tissue, i.e., in the tissue samples from NSCLC patients that had experienced a recurrence of their cancer after treatment with an EGFR-TK inhibitor, specifically gefitinib (IRESSA®).

These results demonstrate that the present protein expression profiles are indicative of therapeutic efficacy of erlotinib or gefitinib in those NSCLC patients having tumors consistent with the expression profile.

Using the techniques described above, protein and gene expression profiles were generated from NSCLC patient samples, and expression profiles unique to patients responsive to therapy with erlotinib or gefitinib were identified. Fifteen proteins identified as being associated with therapeutic efficacy of these compounds are listed in Table 1 above.

Assays

The present invention further comprises methods and assays for determining whether an NSCLC patient is likely to respond to treatment with an EGFR-TK inhibitor, including erlotinib or gefitinib. According to one aspect, a formatted IHC assay can be used for determining if a tumor of an NSCLC patient cancer tumor exhibits the present GPEP. The assays may be formulated into kits that include all or some of the materials needed to conduct the analysis, including reagents (antibodies, detectable labels, etc.) and instructions.

The assay method of the invention comprises contacting a tumor sample from an NSCLC patient with a group of antibodies specific for some or all of the genes or proteins in the present GPEP, and determining the occurrence of up- or down-regulation of these genes or proteins in the samples. The use of TMAs allows numerous samples, including control samples, to be assayed simultaneously.

In a preferred embodiment, the method comprises contacting a tumor sample from an NSCLC patient with a group of antibodies specific for some or all of the proteins in the present GPEP, and determining the occurrence of up- or down-regulation of these proteins. Up-regulation of one or more of the following proteins: p70S6K, phospho-S6, phospho-AKT, phospho-mTOR, phospho-pTEN, EGFR, phospho-ER, phospho-AR, AIK, osteopontin, MMP11 and GFAP; and down-regulation of one or more of the following proteins: phospho-p70S6, phospho-MEK, phospho-MAPK, phospho-IGFR1/InR, phospho-EGFR and phospho-HER2, is indicative of the patient's responsiveness to an EGFR-TK inhibitor, such as erlotinib or gefitinib. Preferably, at least four, preferably between four and nine, and most preferably between nine and eighteen antibodies are used in the present method.

The method preferably also includes detecting and/or quantitating control or "reference proteins". Detecting and/or quantitating the reference proteins in the samples normalizes the results and thus provides further assurance that the assay is working properly. In a currently preferred embodiment, antibodies specific for one or more of the following reference proteins are included: ACTB, GAPD, GUSB, RPLP0 and/or TRFC.

The present invention further comprises a kit containing reagents for conducting an IHC analysis of tissue samples or cells from colon cancer patients, including antibodies specific for at least four of the proteins in the GPEP and for any reference proteins. The antibodies are preferably tagged with means for detecting the binding of the antibodies to the proteins of interest, e.g., detectable labels. Preferred detectable labels include fluorescent compounds or quantum dots, however other types of detectable labels may be used. Detectable labels for antibodies are commercially available, e.g. from Ventana Medical Systems, Inc.

Immunohistochemical methods for detecting and quantitating protein expression in tissue samples are well known. Any method that permits the determination of expression of several different proteins can be used. See. e.g., Signoretti et al., "Her-2-neu Expression and Progression Toward Androgen Independence in Human Prostate Cancer," *J. Natl. Cancer Instit.*, 92(23):1918-25 (2000); Gu et al., "Prostate stem cell antigen (PSCA) expression increases with high gleason score, advanced stage and bone metastasis in prostate cancer," *Oncogene*, 19:1288-96 (2000). Such methods can be efficiently carried out using automated instruments designed for immunohistochemical (IHC) analysis. Instruments for rapidly performing such assays are commercially available, e.g., from Ventana Molecular Discovery Systems or Lab Vision Corporation. Methods according to the present invention using such instruments are carried out according to the manufacturer's instructions.

Protein-specific antibodies for use in such methods or assays are readily available or can be prepared using well-established techniques. Antibodies specific for the proteins in the GPEP disclosed herein can be obtained, for example, from Cell Signaling Technology, Inc. Santa Cruz Biotechnology, Inc. or Abcam.

The present invention is illustrated further by the following non-limiting Example.

Example

Clinical Studies

A multicenter clinical trial in the United States evaluated the tumor response rate of gefitinib (IRESSA®) at dosages of 250 and 500 mg/day in patients with advanced non-small cell lung cancer (NSCLC) whose disease had progressed after at least two prior chemotherapy regimens including a platinum drug and docetaxel. IRESSA® was taken once daily at approximately the same time each day.

Two hundred and sixteen patients received IRESSA®; 102 (47%) received a 250 mg dose and 114 (53%) received a 500 mg daily dose. Study patient demographics and disease characteristics are summarized in Table A.

TABLE A

| Scope of study | |
|---|---|
| Patient Sample Numbers | Treatment |
| 102 Patients (47%) | 250 mg Iressa |
| 114 Patients (53%) | 500 mg Iressa |
| 142 Patients | Platinum and docetaxel therapies |
| 142 Patients | Positive disease progression |

Forty-one percent of the patients had received two prior treatment regimens, 33% had received three prior treatment regimens, and 25% had received four or more prior treatment regimens. Effectiveness of IRESSA® as third line therapy was determined in the 142 evaluable patients with documented disease progression on platinum and docetaxel therapies or who had had unacceptable toxicity on these agents.

Tissue MicroArrays

Tissue samples obtained from the NSCLC patients in the clinical study were obtained and used to prepare tissue micro arrays (TMAs); other TMAs were prepared as controls. The TMAs used in this study are described in Table B:

TABLE B

| Tissue Micro Arrays | |
|---|---|
| Normal Screening Array | This array contained samples of normal (non-cancerous) lung tissue from 200 patients (2 samples per patient) |
| Lung Treatment EGFR | This array contained 500 patient samples obtained from the NSCLC patients who had been treated with IRESSA ®): 250 tumor samples and 250 normal lung tissue samples from the same patients. |
| Cancer screening survey array | Positive control array. This array contained 200 tumor samples for cancers other than lung cancer: 50 breast cancer, 50 colon cancer, 50 prostate cancer and 50 lung cancer. |
| Lung Progression | Negative control array. This array contained samples from the NSCLC patients who progressed to the next stage of lung cancer or experience a recurrence of NSCLC after treatment with gefitinib (IRESSA ®). |

The TMAs were constructed according to the following procedure:

Tissue cores from donor block containing the patient tissue samples were inserted into a recipient paraffin block. These tissue cores are punched with a thin walled, sharpened borer. An X-Y precision guide allowed the orderly placement of these tissue samples in an array format.

Presentation: TMA sections were cut at 4 microns and are mounted on positively charged glass microslides. Individual elements were 0.6 mm in diameter, spaced 0.2 mm apart.

Elements: In addition to TMAs containing the NSCLC samples, screening arrays were produced made up of pancreatic cancers, lymphoma, head and neck cancer, breast cancers and colon cancers tissue samples, 2 each from a different patient. Additional normal tissue samples were included for quality control purposes.

Specificity: The TMAs were designed for use with the specialty staining and immunohistochemical methods described below for gene expression screening purposes, by using monoclonal and polyclonal antibodies over a wide range of characterized tissue types.

Accompanying each array was an array locator map and spreadsheet containing patient diagnostic, histologic and demographic data for each element.

Immunohistochemical Staining

Immunohistochemical staining techniques were used for the visualization of tissue (cell) proteins present in the tissue samples. These techniques were based on the immunoreactivity of antibodies and the chemical properties of enzymes or enzyme complexes, which react with colorless substrate-chromogens to produce a colored end product. Initial immunoenzymatic stains utilized the direct method, which conjugated directly to an antibody with known antigenic specificity (primary antibody).

A modified labeled avidin-biotin technique was employed in which a biotinylated secondary antibody formed a complex with peroxidase-conjugated streptavidin molecules. Endogenous peroxidase activity was quenched by the addition of 3% hydrogen peroxide. The specimens then were incubated with the primary antibodies followed by sequential incubations with the biotinylated secondary link antibody (containing anti-rabbit or anti-mouse immunoglobulins) and peroxidase labeled streptavidin. The primary antibody, secondary antibody, and avidin enzyme complex is then visualized utilizing a substrate-chromogen that produces a brown pigment at the antigen site that is visible by light microscopy. Table C lists the antibodies used in this example.

TABLE C

| Antibody | CST # |
| --- | --- |
| Phospho-p70S6 | CST #9206 |
| Total p70S6 Kinase | CST #9202 |
| Phospho-S6 | CST #2211 |
| Phospho-AKT | CST #3787 |
| Phospho-mTOR | CST #2971 |
| Phospho-pTEN | CST #9554 |
| Phospho MEK | CST #9121 |
| Phospho MAPK | CST #9106 |
| Phospho-IGFR/InR | CST #3021 |
| Total EGFR | CST #2232 |
| Phospho-EGFR | CST #2234 |
| Phospho-HER2(ErbB2) | CST #2241 |
| Phospho-AR | SC #26406-R |
| AIK | CST #4718 |
| Phospho-ER | CST #2511 |

CST refers to Cell Signaling Technology, Inc.
SC refers to Santa Cruz Biotechnology, Inc.

Automated Immunohistochemistry Staining Procedure (IHC):
1. Heat-induced epitope retrieval (HIER) using 10 mM Citrate buffer solution, pH 6.0, was performed as follows:
   a. Deparaffinized and rehydrated sections were placed in a slide staining rack.
   b. The rack was placed in a microwaveable pressure cooker; 750 ml of 10 mM Citrate buffer pH 6.0 was added to cover the slides.
   c. The covered pressure cooker was placed in the microwave on high power for 15 minutes.
   d. The pressure cooker was removed from the microwave and cooled until the pressure indicator dropped and the cover could be safely removed.
   e. The slides were allowed to cool to room temperature, and immunohistochemical staining was carried out.
2. Slides were treated with 3% $H_2O_2$ for 10 min. at RT to quench endogenous peroxidase activity.
3. Slides were rinsed gently with phosphate buffered saline (PBS).
4. The primary antibodies were applied at the predetermined dilution (according to Cell Signaling Technology's Specifications) for 30 min at room temperature. Normal mouse or rabbit serum 1:750 dilution was applied to negative control slides.
5. Slides were rinsed with phosphate buffered saline (PBS).
6. Secondary biotinylated link antibodies* were applied for 30 min at room temperature.
7. Slides were rinsed with phosphate buffered saline (PBS).
8. The slides were treated with streptavidin-HRP (streptavidin conjugated to horseradish peroxidase)** for 30 min at room temperature.
9. Slides were rinsed with phosphate buffered saline (PBS).
10. The slides were treated with substrate/chromogen*** for 10 min at room temperature.
11. Slides were raised with distilled water.
12. Counterstain in Hematoxylin was applied for 1 min.
13. Slides were washed in running water for 2 min.
14. The slides were then dehydrated, cleared and the coverglass was mounted
   *Secondary antibody: biotinylated anti-chicken and anti-mouse immunoglobulins in phosphate buffered saline (PBS), containing carrier protein and 15 mM sodium azide.
   **Streptavidin-HRP in PBS containing carrier protein and anti-microbial agents from Ventana,
   ***Substrate-Chromogen is substrate-imidazole-HCl buffer pH 7.5 containing $H_2O_2$ and anti-microbial agents, DAB-3,3'-diaminobenzidine in chromogen solution from Ventana.

Experiment Notes:

All primary antibodies were titrated to dilutions according to manufacturer's specifications. Staining of TE30 Test Array slides (described below) was performed with and without epitope retrieval (HIER). The slides were screened by a pathologist to determine the optimal working dilution. Pretreatment with HIER provided strong specific staining with little to no background. The above immunohistochemical staining was carried out using a Benchmark instrument from Ventana Medical Systems, Inc.

Scoring Criteria:

Staining was scored on a 0-3+ scale, with 0=no staining, and trace (tr) being less than 1+ but greater than 0. The scoring procedures are described in Signoretti et al., *J. Nat. Cancer Inst.*, Vol. 92, No. 23, p. 1918 (December 2000) and Gu et al., *Oncogene*, 19, 1288-1296 (2000). Grades of 1+ to 3+ represent increased intensity of staining with 3+ being strong, dark brown staining. Scoring criteria was also based on total percentage of staining 0=0%, 1=less than 25%, 2=25-50% and 3=greater than 50%. The percent positivity and the intensity of staining for both Nuclear and Cytoplasmic as well as sub-cellular components were analyzed. Both the intensity and percentage positive scores were multiplied to produce one number 0-9. 3+ staining was determined from known expression of the antigen from the positive controls either Breast Adenocarcinoma and/or LNCAP cells.

Positive, Negative and Isotype Matched Controls and Reproducibility:

Positive tissue controls were defined via western blot analysis using the antibodies listed in Table C. This experiment was performed to confirm the level of protein expression in each given control. Negative controls were also defined by the same. The positive controls consisted of Breast, Prostate, Colon and Lung cancer samples.

Positive expression was also confirmed using a Xenograft array. To make this array, SCID mice were injected with tumor cells derived from NSCLC tumors of patients shown to be responsive to gefitinib (IRESSA®), and tumors were allowed to grow. The mice then were injected with 200 mg/kg of IRESSA®, and the mice were monitored to observe responsiveness to the drug.

As a result of treatment with IRESSA®, the tumors formed in the SCID mice were reduced or eliminated. The tumors were found to have the same gene expression profile as that identified in human patients who were responders to gefitinib therapy.

Reproducibility:

All runs were grouped by antibody and tissue arrays which ensured that the runs were normalized, meaning that all of the tissue arrays were stained under the same conditions with the same antibody on the same run. A test array containing thirty negative control samples (TE 30) comprising non-cancerous tissues derived from different (non-lung) organs also was provided. This TE 30 was compared to the previous antibody run and scored accordingly. The reproducibility was compared and validated.

Results:

In tumor samples obtained from those NSCLC patients that were responsive to treatment with an EGFR-TK inhibitor, gefitinib, the following proteins were up-regulated: p70S6K, phospho-S6, phospho-AKT, phospho-mTOR, phospho-pTEN, EGFR, phospho-ER, phospho-AR and AIK; and the following proteins were down-regulated: phospho-p70S6, phospho-MEK, phospho-MAPK, phospho-IGFR1/InR, phospho-EGFR and phospho-HER2, compared with an expression of these proteins in normal lung tissue from these patients and the normal lung tissue from other patients. In contrast, most of these proteins were not up- or down-regulated in the positive control tissue samples. These proteins also were not up- or down-regulated in the negative control tissue, i.e., in the tissue samples from NSCLC patients that had experienced a recurrence of their cancer after treatment with gefitinib. NSCLC patients with tumors exhibiting the present gene and/or protein expression profiles had survived for a longer period of time after treatment with gefitinib compared with NSCLC patients whose tumors did not exhibit the present gene and/or protein expression profiles.

These results show that the present protein expression profile is indicative of therapeutic efficacy of erlotinib or gefitinib in those NSCLC patients having tumors consistent with the expression profile. These data support a potential role for this signature as a determinant of EGFR activity in NSCLC tumor cells and expression as a novel biomarkers for predicting clinical activity of the EGFR inhibitors erlotinib and gefitinib in NSCLC patients.

What is claimed is:

1. An assay for determining if a patient diagnosed with lung cancer is likely to respond to therapeutic treatment with an EGFR-TK inhibitor selected from gefitinib or erlotinib, comprising (a) obtaining a biological sample of tumor tissue or tumor cells from said patient;

(b) determining expression levels in said biological sample of the following proteins: p70S6K, comprising the amino acid sequence of SEQ ID NO. 17, phospho-S6 comprising the amino acid sequence of SEQ ID NO. 18, phospho-AKT comprising the amino acid sequence of SEQ ID NO. 19, phospho-mTOR comprising the amino acid sequence of SEQ ID NO. 20, phospho-pTEN comprising the amino acid sequence of SEQ ID NO. 21, EGFR comprising the amino acid sequence of SEQ ID NO. 25, phospho-ER comprising the amino acid sequence of SEQ ID NO. 27, phospho-AR comprising the amino acid sequence of SEQ ID NO. 28, AIK comprising the amino acid sequence of SEQ ID NO. 29, osteopontin comprising the amino acid sequence of SEQ ID NO. 30, MMP11 comprising the amino acid sequence SEQ ID NO. 31 and GFAP comprising the amino acid sequence of SEQ ID NO. 32; and (c) comparing the expression levels in step (b) to expression levels of the same proteins in normal tissue or cells, wherein the patient is a responder to treatment with an EGFR-TK inhibitor if the level of the p70S6K, phospho-S6, phospho-AKT, phospho-mTOR, phospho-pTEN, EGFR, phospho-ER, phospho-AR, AIK, osteopontin, MMP11 and GFAP is up-regulated in the tissue or cells from said biological sample as compared to said normal tissue or cells.

* * * * *